(12) United States Patent
Petry et al.

(10) Patent No.: US 8,933,024 B2
(45) Date of Patent: Jan. 13, 2015

(54) AZOLOPYRIDIN-3-ONE DERIVATIVES AS INHIBITORS OF LIPASES AND PHOSPHOLIPASES

(75) Inventors: Stefan Petry, Frankfurt (DE); Norbert Tennagels, Frankfurt (DE); Karl-Heinz Baringhaus, Frankfurt (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/805,289

(22) PCT Filed: Jun. 17, 2011

(86) PCT No.: PCT/EP2011/060122
§ 371 (c)(1),
(2), (4) Date: Mar. 1, 2013

(87) PCT Pub. No.: WO2011/157827
PCT Pub. Date: Dec. 22, 2011

(65) Prior Publication Data
US 2013/0157941 A1 Jun. 20, 2013

(30) Foreign Application Priority Data
Jun. 18, 2010 (EP) ..................................... 10305655

(51) Int. Cl.
*A61K 38/28* (2006.01)
*A61P 5/50* (2006.01)
*C07D 513/04* (2006.01)
*A61K 31/437* (2006.01)
*A61K 31/444* (2006.01)
*A61K 31/4545* (2006.01)
*A61K 31/496* (2006.01)
*A61K 31/5377* (2006.01)
*A61K 31/5383* (2006.01)

(52) U.S. Cl.
CPC ............ *C07D 513/04* (2013.01); *A61K 31/437* (2013.01); *A61K 31/444* (2013.01); *A61K 31/4545* (2013.01); *A61K 31/496* (2013.01); *A61K 31/5377* (2013.01); *A61K 31/5383* (2013.01); *A61K 46/06* (2013.01)
USPC ......................................................... 514/6.5

(58) Field of Classification Search
CPC . C07D 213/81; A61K 31/437; A61K 31/444; A61K 31/4184
See application file for complete search history.

(56) References Cited

U.S. PATENT DOCUMENTS 4,512,985 A * 4/1985 Maignan et al. .............. 514/301

FOREIGN PATENT DOCUMENTS

WO   WO 2004/094394 A1   11/2004
WO   WO 2007110216 A1 * 10/2007

OTHER PUBLICATIONS

Hiroshi Okada, et al., "Synthesis and Antitumor Activities of Prodrugs of Benzoylphenylureas", Chem. Pharm. Bull., (Jan. 1994), vol. 42, No. 1, pp. 57-61.
Delia A. Haynes, et al., "Occurrence of Pharmaceutically Acceptable Anions and Cations in the Cambridge Structural Database", Journal of Pharmaceutical Sciences, (Oct. 2005), vol. 94, No. 10, pp. 2111-2120.
International Preliminary Report on Patentablility dated Dec. 19, 2012 issued in PCT/EP2011/060122.
International Search Report dated Sep. 21, 2011 issued in PCT/EP2011/060122.

* cited by examiner

*Primary Examiner* — Marcela M Cordero Garcia
*Assistant Examiner* — Kaipeen Yang
(74) *Attorney, Agent, or Firm* — Scully, Scott, Murphy & Presser, P.C.

(57) ABSTRACT

The present invention relates to azolopyridin-3-one derivatives of the general formula (I) with the meanings specified in the description, to their pharmaceutically usable salts and to their use as drug substances.

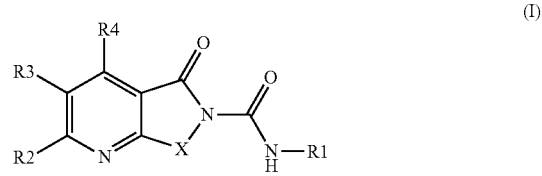

16 Claims, No Drawings

AZOLOPYRIDIN-3-ONE DERIVATIVES AS INHIBITORS OF LIPASES AND PHOSPHOLIPASES

The present invention relates to azolopyridin-3-one derivatives of the formula I, to the pharmaceutically usable salts thereof and to the use thereof as medicaments.

Structurally similar indazole compounds with pharmaceutical action are known from WO 2004/093872. Structurally similar benzisoxazole compounds with pharmaceutical action are known from WO 2004/094393. U.S. Pat. No. 4,512,985 describes isothiazolopyridin-3-one compounds for acne treatment.

Structurally similar azolopyridine compounds with inhibiting action on endothelial lipase are known from WO 2007/110216. WO 2004/094394, WO 2004/094393, WO 2004/093872, WO 2007/045393, WO 2007/110215, WO 208/122352 and WO 2008/122357 describe compounds with inhibiting action on endothelial lipase.

It is an object of the present invention to provide alternative compounds which bring about inhibition of endothelial lipase.

The invention provides azolopyridin-3-one derivatives of the formula I

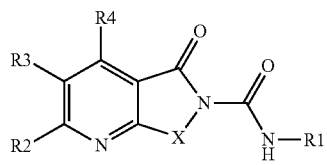
(I)

where:
X is S or $SO_2$;
R1 is $(C_5\text{-}C_{16})$-alkyl,
a radical of the formula Ia

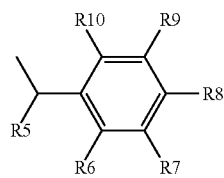

in which
R5 is hydrogen, $(C_1\text{-}C_3)$-alkyl;
R6, R7, R8, R9, R10
are each independently hydrogen, F, Cl, Br, I, OH, $CF_3$, $NO_2$, CN, $OCF_3$, $OCHF_2$, O—$(C_1\text{-}C_6)$-alkyl, O—$(C_1\text{-}C_4)$-alkoxy-$(C_1\text{-}C_4)$-alkyl, S—$(C_1\text{-}C_6)$-alkyl, $(C_1\text{-}C_6)$-alkyl, $(C_2\text{-}C_4)$-haloalkyl, O—$(C_2\text{-}C_4)$-haloalkyl, $(C_2\text{-}C_6)$-alkenyl, $(C_2\text{-}C_6)$-alkynyl, N(R11)(R12), $SO_2$—$CH_3$, $SO_2$—N(R13)(R14), $SF_5$, $SCF_3$, COOH, COO—$(C_1\text{-}C_6)$-alkyl, CON(R15)(R16), N(R17)CO(R18), N(R19)$SO_2$(R20), CO(R21), $(CR22R23)_x$-O(R24), $(CR22R23)_x$-CO—O(R24), O—$(CR22R23)_x$-CO—O(R24), $(CR22R23)_x$-N(R25)(R26), O—$(CR22R23)_x$-N(R25)(R26), $(CR22R23)_x$-CON(R25)(R26), O—$(CR22R23)_x$-CON(R25)(R26), O—CO—N(R25)(R26), O—CO—$(C_1\text{-}C_6)$-alkylene-CO—O—$(C_1\text{-}C_6)$-alkyl, O—CO—$(C_1\text{-}C_6)$-alkylene-CO—OH, O—CO—$(C_1\text{-}C_6)$-alkylene-CO—N(R27)(R28);
is independently 0, 1, 2, 3, 4, 5, 6;
or
R7 or R8 is
$(O)_y$—$(CH_2)_{y'}$—$(O)_{y''}$—$(CH_2)_{y'''}$—R100;
y, y″ are each independently 0, 1;
y′, y‴ are each independently 1, 2, 3, 4, 5, 6;
R100 is a 4- to 10-membered mono- or bicyclic saturated, partly unsaturated or aromatic ring which may contain 1 to 4 heteroatoms selected from the group of oxygen, nitrogen and sulfur, where the ring system may additionally be mono- or polysubstituted by F, Cl, Br, I, OH, $CF_3$, $NO_2$, CN, $OCF_3$, O—$(C_1\text{-}C_6)$-alkyl, O—$(C_1\text{-}C_4)$-alkoxy-$(C_1\text{-}C_4)$-alkyl, S—$(C_1\text{-}C_6)$-alkyl, $(C_1\text{-}C_6)$-alkyl, $(C_2\text{-}C_4)$-haloalkyl, $(C_2\text{-}C_6)$-alkenyl, $(C_3\text{-}C_8)$-cycloalkyl, O—$(C_3\text{-}C_8)$-cycloalkyl, $(C_2\text{-}C_6)$-alkynyl, N(R29)(R30), $SO_2$—$CH_3$, $SF_5$, COOH, COO—$(C_1\text{-}C_6)$-alkyl, CON(R31)(R32), N(R33)CO(R34), N(R35)$SO_2$(R36), CO(R37), $(CR38R39)_x$-O(R40), $(CR38R39)_x$-CO—O(R40), O—$(CR22R23)_x$-CO—O(R40), $(CR22R23)_x$-N(R41)(R42), O—$(CR38R39)_x$-N(R41)(R42), $(CR38R39)_x$-CON(R41)(R42), O—$(CR38R39)_x$-N(R41)(R42), —O—CO—N(R41)(R42), O—CO—$(C_1\text{-}C_6)$-alkylene-CO—O—$(C_1\text{-}C_6)$-alkyl, O—CO—$(C_1\text{-}C_6)$-alkylene-CO—OH, O—CO—$(C_1\text{-}C_6)$-alkylene-CO—N(R43)(R44);
x′ is 0, 1, 2, 3, 4, 5, 6;
or
R7 and R8 or R8 and R9 or R9 and R10
together with the carbon atom which bears them form a monocyclic, 5- to 7-membered saturated, partly unsaturated or aromatic ring system whose individual members may be substituted by —CHR45-, —CR46R47-, =(C—R46)-, O, N or S, with the proviso that no two units from the group of —O—, N and —S— may be adjacent;
R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44
are each independently hydrogen, $(C_1\text{-}C_6)$-alkyl;
or
R11 and R12, R13 and R14, R15 and R16, R25 and 26, R27 and R28, R29 and R30, R31 and R32, R41 and 42, R43 and 44
each independently form, optionally together with the nitrogen atom to which they are bonded, a 5-6-membered ring which, apart from the nitrogen atom, may also include 0-1 further heteroatom from the group of NH, N—$(C_1\text{-}C_6)$-alkyl, oxygen and sulfur;
R45, R46, R47 are the same or different and are each F, Cl, Br, I, OH, $CF_3$, $NO_2$, CN, $OCHF_2$, $OCF_3$, $SF_5$, O—$(C_1\text{-}C_6)$-alkyl, O—$(C_1\text{-}C_4)$-alkoxy-$(C_1\text{-}C_4)$-alkyl, S—$(C_1\text{-}C_6)$-alkyl, $(C_1\text{-}C_6)$-alkyl, $(C_2\text{-}C_4)$-haloalkyl, O—$(C_2\text{-}C_4)$-haloalkyl, $(C_2\text{-}C_6)$-alkenyl, $(C_3\text{-}C_8)$-cycloalkyl, O—$(C_3\text{-}C_8)$-cycloalkyl, $(C_2\text{-}C_6)$-alkynyl, N(R134)(R135), $SO_2$—$CH_3$, COOH, COO—$(C_1\text{-}C_6)$-alkyl, CON(R136)(R137), N(R138)CO(R139), N(R140)$SO_2$(R141), CO(R142), $(CR143R144)_{x''}$-O(R145), $(CR143R144)_{x''}$-CO—O(R145), O—$(CR143R144)_{x''}$-CO—O(R145), $(CR143R144)_{x''}$-N(R146)(R147), O—$(CR143R144)_{x''}$-N(R146)(R147), $(CR143R144)_{x''}$-CON(R146)(R147), O—$(CR143R144)_{x''}$-CON(R146)(R147), O—CO—N(R146)(R147), O—CO—$(C_1\text{-}C_6)$-alkylene-CO—O—$(C_1\text{-}C_6)$-alkyl, O—CO—$(C_1\text{-}C_6)$-alkylene-CO—OH, O—CO—$(C_1\text{-}C_6)$-alkylene-CO—N(R148)(R149);
x″ is independently 1, 2, 3, 4, 5, 6;

R134, R135, R136, R137, R138, R139, R140, R141, R142, R143, R144, R145, R146, R147, R148, R149
are the same or different and are each hydrogen, $(C_1-C_6)$-alkyl;
a radical of the formula Ib

in which
R5 is hydrogen, $(C_1-C_3)$-alkyl;
Het is a 4- to 10-membered mono- or bicyclic aromatic ring containing 1 to 4 heteroatoms selected from the group of oxygen, nitrogen and sulfur, where the ring system may additionally be mono- or polysubstituted independently by F, Cl, Br, I, OH, $CF_3$, $NO_2$, CN, $OCF_3$, $OCHF_2$, O—$(C_1-C_6)$-alkyl, O—$(C_1-C_4)$-alkoxy-$(C_1-C_4)$-alkyl, S—$(C_2-C_4)$-haloalkyl, O—$(C_2-C_4)$-haloalkyl, $(C_2-C_6)$-alkenyl, $(C_2-C_6)$-alkynyl, N(R48)(R49), $SO_2$—$CH_3$, $SO_2$—N(R50)(R51), $SF_5$, $SCF_3$, COOH, COO—$(C_1-C_6)$-alkyl, CON(R52)(R53), N(R54)CO(R55), N(R56)$SO_2$(R57), CO(R58), $(CR59R60)_{x'''}$-O(R61), $(CR59R60)_{x'''}$-CO—O(R61), O—$(CR59R60)_{x'''}$-CO—O(R61), $(CR59R60)_{x'''}$-N(R62)(R63), O—$(CR59R60)_{x'''}$-N(R62)(R63), $(CR59R60)_{x'''}$-CON(R62)(R63), O—$(CR59R60)_{x'''}$-CON(R62)(R63), O—CO—N(R62)(R63), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R64)(R65); or $(O)_{y'}$—$(CH_2)_{y''}$—$(O)_{y'''}$—$(CH_2)_{y''''}$—R101,
x''' is independently 1, 2, 3, 4, 5, 6;
y, y'' are each independently 0, 1;
y', y''' are each independently 0, 1, 2, 3, 4, 5, 6;
R101 is a 4- to 10-membered mono- or bicyclic saturated, partly unsaturated or aromatic ring which may contain 1 to 4 heteroatoms selected from the group of oxygen, nitrogen and sulfur, where the ring system may additionally be mono- or polysubstituted by F, Cl, Br, I, OH, $CF_3$, $NO_2$, CN, $OCHF_2$, $OCF_3$, O—$(C_1-C_6)$-alkyl, O—$(C_1-C_4)$-alkoxy-$(C_1-C_4)$-alkyl, S—$(C_1-C_6)$-alkyl, $(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, N(R66)(R67), $SO_2$—$CH_3$, $SF_5$, COOH, COO—$(C_1-C_6)$-alkyl, CON(R68)(R69), (C), N(R70)CO(R71), N(R72)$SO_2$(R73), CO(R74), $(CR75R76)_{x''''}$-O(R77R75R76)$_{x''''}$-CO—O(R77), O—$(CR75R76)_{x''''}$-CO—O(R77), $(CR75R76)_{x''''}$-N(R78)(R79), O—$(CR75R76)_{x''''}$-N(R78)(R79), $(CR75R76)_{x''''}$-CON(R78)(R79), O—$(CR75R76)_{x''''}$-CON(R78)(R79), O—CO—N(R78)(R79), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R80)(R81);
x'''' is independently 1, 2, 3, 4, 5, 6;
R48, R49, R50, R51, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81
are each independently hydrogen, $(C_1-C_6)$-alkyl;
or
R48 and R49, R50 and R51, R52 and R53, R62 and R63, R64 and R65, R66 and R67, R68 and R69, R78 and R79, R80 and R81 each independently form, optionally together with the nitrogen atom to which they are bonded, a 5-6-membered ring which, apart from the nitrogen atom, may also include 0-1 further heteroatom from the group of NH, N—$(C_1-C_6)$-alkyl, oxygen and sulfur;
a radical of the formula Ic

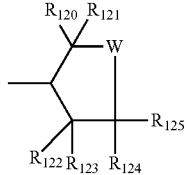

in which
W is —C(R126)(R127)-, —C(R126)(R127)-C(R128)(R129)-, —C(R126)(R127)-O—;
R120, R121, R122, R123, R124, R125, R126, R127, R128, R129 are the same or different and are each hydrogen, F, Cl, Br, I, OH, $CF_3$, $NO_2$, CN, $OCHF_2$, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkenyl, $(C_2-C_6)$-alkynyl, N(R90)(R91), $SO_2$—$CH_3$, COOH, COO—$(C_1-C_6)$-alkyl, CON(R92)(R93), N(R94)CO(R95), N(R96)$SO_2$(R97), CO(R98), $(CR99R102)_z$-O(R103), $(CR99R76)_z$-CO—O(R103), O—$(CR99R102)_z$-CO—O(R103), $(CR99R102)_z$-N(R104)(R105), O—$(CR99R102)_z$-N(R104)(R105), $(CR99R102)_z$-CON(R104)(R105), O—$(CR99R102)_z$-CON(R104)(R105), O—CO—N(R104)(R105), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R106)(R107);
z is independently 1, 2, 3, 4, 5, 6;
R90, R91, R92, R93, R94, R95, R96, R97, R98, R99, R102, R103, R104, R105, R106, R107
are the same or different and are each hydrogen, $(C_1-C_6)$-alkyl;
or
R120 and R126 or R121 and R127 together with the carbon atom which bears them form a monocyclic, 5- or 6-membered saturated, partly unsaturated or aromatic ring system whose individual members may be substituted by —CHR130-, —CR131R132-, =(C—R133)-;
or
R122 and R124, or R123 and R125 together with the carbon atom which bears them form a monocyclic, 5- or 6-membered saturated, partly unsaturated or aromatic ring system whose individual members may be substituted by —CHR130-, —CR131R132-, =(C—R133)-;
R130, R131, R132, R133 are the same or different and are each F, Cl, Br, I, OH, $CF_3$, $NO_2$, CN, $OCHF_2$, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R160)(R161), $SO_2$—$CH_3$, COOH, COO—$(C_1-C_6)$-alkyl, CON(R162)(R163), N(R164)CO(R165), N(R166)$SO_2$(R167), CO(R168), $(CR169R170)_z$-O(R171), $(CR169R170)_z$-CO—O(R77), O—$(CR169R170)_z$-CO—O(R171), $(CR169R170)_z$-N(R172)(R173), O—$(CR169R170)_z$-N(R172)(R173), $(CR169R170)_z$-CON(R172)(R173), O—$(CR169R170)_z$-CON(R172)(R173), O—CO—N (R172)(R173), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R172)(R173);

z' is independently 1, 2, 3, 4, 5, 6;

R160, R161, R162, R163, R164, R165, R166, R167, R168, R169, R170, R171, R172, R173
are the same or different and are each hydrogen, ($C_1$-$C_6$)-alkyl;
or
R160 and R161, R162 and R163, R172 and R173 each independently form, optionally together with the nitrogen atom to which they are bonded, a 5-6-membered ring which, apart from the nitrogen atom, may also include 0-1 further heteroatom from the group of NH, N—($C_1$-$C_6$)-alkyl, oxygen and sulfur;

R2, R3, R4 are the same or different and are each hydrogen, F, Cl, Br, I, OH, $CF_3$, $NO_2$, CN, $OCHF_2$, $OCF_3$, $SF_5$, O—($C_1$-$C_6$)-alkyl, O—($C_1$-$C_4$)-alkoxy-($C_1$-$C_4$)-alkyl, 5-($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, aryl, ($C_2$-$C_6$)-alkynyl, N(R200)(R201), $SO_2$—$CH_3$, COOH, COO—($C_1$-$C_6$)-alkyl, CON(R202)(R203), N(R204)CO(R205), N(R206)$SO_2$(R207), CO(R208), $(CR209R210)_{z''}$-O(R211), $(CR209R210)_{z''}$-CO—O(R211), O—$(CR209R210)_{z''}$-CO—O(R211), $(CR209R210)_{z''}$-N(R212)(R213), O—$(CR209R210)_{z''}$-N(R212)(R213), $(CR209R210)_{z''}$-CON(R212)(R213), O—$(CR209R210)_{z''}$-CON(R212)(R213), O—CO—N(R212)(R213), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R212)(R213);

z'' is independently 1, 2, 3, 4, 5, 6;

R200, R201, R202, R203, R204 R205, R206, R207, R208, R209, R210, R211, R212, R213
are the same or different and are each hydrogen, ($C_1$-$C_6$)-alkyl,
or
R200 and R201, R202 and R203, R212 and R213
each independently form, optionally together with the nitrogen atom to which they are bonded, a 5-6-membered ring which, apart from the nitrogen atom, may also include 0-1 further heteroatom from the group of NH, N—($C_1$-$C_6$)-alkyl, oxygen and sulfur;

the tautomeric forms of the compounds and the physiologically compatible salts and N-oxides thereof;

with the proviso that the compounds where R2, R3, R4=hydrogen, X=S and R1=heptyl, nonyl or cyclohexyl are excluded.

The compounds of the formula I are notable in that they have an improved solubility in aqueous media as compared with structurally similar compounds with inhibiting action on endothelial lipase (especially in physiologically relevant buffer systems) combined with simultaneous high activity. Furthermore, preferred inventive compounds have an improved metabolic stability as compared with prior art compounds. Chemical stability in blood plasma has also been improved significantly.

The alkyl, alkenyl and alkynyl radicals in the substituents R1 to R213 may be straight-chain and/or branched. This is also the case when the alkyl, alkenyl and alkynyl radicals are part of another group, for example part of an alkoxy group (such as ($C_1$-$C_4$)-alkoxy-($C_1$-$C_4$)-alkyl)).

Suitable halogens are fluorine, chlorine, bromine and iodine, preferably fluorine, chlorine and bromine, more preferably fluorine.

Examples of alkyl groups are: methyl, ethyl, propyl, butyl, pentyl, hexyl, heptyl and octyl. This includes both the n-isomers of these radicals and branched isomers such as isopropyl, isobutyl, isopentyl, sec-butyl, tert-butyl, neopentyl, 3,3-dimethylbutyl etc. Haloalkyl is an alkyl singly, multiply or fully substituted by halogen. Preferred halogens are fluorine and chlorine.

Examples of alkyl groups substituted by halogen are fluorinated alkyl groups such as $CF_3$, $CHF_2$, $CH_2F$, 3-fluoroprop-1-yl, 2,2,1,1-tetrafluoroethyl. The additional substituents may occur in any position in the alkyl radical. Unless defined otherwise, the alkyl radicals are preferably unsubstituted.

In the context of the present application, cycloalkyl is understood to mean cycloalkyl and cycloalkylalkyl (alkyl substituted in turn by cycloalkyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Polycyclic ring systems may also be possible, such as decalinyl, norbornanyl, bornanyl or adamantanyl. The cycloalkyl radicals may be unsubstituted or optionally substituted by one or more further radicals as listed by way of example above for the alkyl radicals. Unless defined otherwise, the cycloalkyl radicals are preferably unsubstituted.

Examples of alkenyl and alkynyl groups are: vinyl, 1-propenyl, 2-propenyl(allyl), 2-butenyl, 2-methyl-2-propenyl, 3-methyl-2-butenyl, ethynyl, 2-propynyl(propargyl), 2-butynyl or 3-butynyl.

In the context of the present application, cycloalkenyl is understood to mean cycloalkenyl radicals and cycloalkenylalkyl radicals (alkyl substituted by cycloalkenyl) containing at least three carbon atoms. Examples of cycloalkenyl are: cyclopentenyl, cyclohexenyl, cycloheptenyl and cyclooctenyl.

The alkenyl radicals and cycloalkenyl radicals may have one to three conjugated or non-conjugated double bonds (i.e. also alkadienyl and alkatrienyl radicals), preferably one double bond in a linear or branched chain. The same applies to the triple bonds for alkynyl radicals. The alkenyl and alkynyl radicals may be unsubstituted or optionally substituted by one or more further radicals as listed by way of example above for the alkyl radicals. Unless defined otherwise, the alkenyl and alkynyl radicals are preferably unsubstituted.

An aryl radical is understood to mean a phenyl or naphthyl radical.

In the context of the present application, a polycyclic group (bi-, tri- or spirocyclic ring skeleton) is understood to mean a group derived from spirans, fused ring systems or bridged ring systems. The spirans are notable for two rings having only one carbon atom in common and the ring planes of the two rings being perpendicular to one another. In the fused ring systems, two rings are joined to one another in such a way that they have two atoms in common. This method of joining involves an "ortho fusion".

Bridged ring systems are ring systems having a bridge of carbon atoms and/or heteroatoms between two nonadjacent atoms of a ring. Illustrative "ring systems with heteroatoms", "heterocyclic rings" and "heterocyclic radicals" are azocinyl, benzimidazolyl, benzofuryl, benzothienyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl represents 2-, 3- and 4-pyridyl. Thienyl represents 2- and 3-thienyl. Furyl represents 2- and 3-furyl.

Also covered are the corresponding N-oxides of these compounds, i.e., for example, 1-oxy-2-, -3- or -4-pyridyl.

In the context of the present invention, a "chemically viable radical" is understood to mean a radical which is stable at room temperature and standard pressure. In the context of the present invention, a "chemically viable radical" in the definition of group A in the compounds of the formula I is preferably understood to mean groups having no heteroatom-heteroatom bonds between the individual members of the groups.

In the context of the present application, a "nonaromatic" ring is preferably understood to mean a ring which is saturated or partly unsaturated. A partly unsaturated ring according to the present application has one or possibly more than one double bond, but the partly unsaturated ring is not aromatic. The expression "nonaromatic" in the context of the present application also includes "nonheteroaromatic" rings.

The compounds of the formula I may have one or more centers of asymmetry. The compounds of the formula I may therefore be in the form of their racemates, enantiomerically enriched mixtures, pure enantiomers, diastereomers and diastereomer mixtures. The present invention encompasses all these isomeric forms of the compounds of the formula I. These isomeric forms can be obtained by known methods, even though some are not expressly described.

Owing to their higher water solubility compared to the starting or base compounds, pharmaceutically acceptable salts are particularly suitable for medical applications. These salts must have a pharmaceutically acceptable anion or cation. Suitable pharmaceutically acceptable acid addition salts of the inventive compounds are, for example, salts of inorganic acids and organic acids. Such pharmaceutically acceptable anions or cations are described in J. Pharm. Sci., Vol. 94, No. 10, 2111-2120, 2005.

Salts with a pharmaceutically unacceptable anion likewise form part of the scope of the invention as useful intermediates for the preparation or purification of pharmaceutically acceptable salts and/or for use in nontherapeutic, for example in vitro, applications.

The term "physiologically functional derivative" used here refers to any physiologically tolerated derivative of an inventive compound of the formula I, for example an ester, which on administration to a mammal, for example a human, is able to form (directly or indirectly) a compound of the formula I or an active metabolite thereof.

Physiologically functional derivatives also include prodrugs of the inventive compounds, as described, for example, in H. Okada et al., Chem. Pharm. Bull. 1994, 42, 57-61. Such prodrugs can be metabolized in vivo to an inventive compound. These prodrugs may or may not be active themselves.

The inventive compounds may also be in various polymorphous forms, for example as amorphous and crystalline polymorphous forms. All polymorphous forms of the inventive compounds are within the scope of the invention and are a further aspect of the invention.

Hereinafter, all references to "compound(s) of the formula I" relate to compound(s) of the formula I as described above, and the salts, racemates, racemic mixtures and pure enantiomers thereof, and to the diastereomers and mixtures thereof, and to solvates and physiologically functional derivatives thereof, as described herein.

If radicals or substituents can occur more than once in the compounds of the formula I, they may each independently be defined as specified and be the same or different.

The symbols in the formula I are preferably each independently defined as follows:

X is preferably S.
In one embodiment,
R1 is $(C_5-C_{16})$-alkyl.
In a further embodiment,
R1 is a radical of the formula Ia

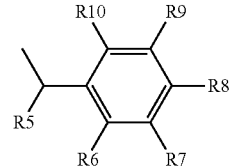

in which
R5 is hydrogen, $(C_1-C_3)$-alkyl;
R6, R7, R8, R9, R10
are each independently hydrogen, F, Cl, Br, I, OH, $CF_3$, $NO_2$, CN, $OCF_3$, $OCHF_2$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R11)(R12), $SO_2$—$CH_3$, $SO_2$—N(R13)(R14), $SF_5$, $SCF_3$, COOH, COO—$(C_1-C_6)$-alkyl, CON(R15)(R16), N(R17)CO(R18), N(R19)$SO_2$(R20), CO(R21), $(CR22R23)_x$-O(R24), $(CR22R23)_x$-CO—O(R24), O—$(CR22R23)_x$-CO—O(R24), $(CR22R23)_x$-N(R25)(R26), O—$(CR22R23)_x$-N(R25)(R26), $(CR22R23)_x$-CON(R25)(R26), O—$(CR22R23)_x$-CON(R25)(R26), O—CO—N(R25)(R26), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R27)(R28);
with the proviso that at least one R6, R7, R8, R9, R10 radical is not hydrogen;
x is independently 0, 1, 2, 3, 4, 5, 6;
or
R7 or R8 is
$(O)_{y}$—$(CH_2)_{y'}$—$(O)_{y''}$—$(CH_2)_{y'''}$—$R^{100}$;
y, y" are each independently 0, 1;
y', y''' are each independently 1, 2, 3, 4, 5, 6;
R100 is a 4- to 10-membered mono- or bicyclic saturated, partly unsaturated or aromatic ring which may contain 1 to 4 heteroatoms selected from the group of oxygen, nitrogen and sulfur, where the ring system may additionally be mono- or polysubstituted by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, N(R29)(R30), $SO_2$—$CH_3$, $SF_5$, COOH, COO—$(C_1$-

$C_6$)-alkyl, CON(R31)(R32), N(R33)CO(R34), N(R35)SO$_2$(R36), CO(R37), (CR38R39)$_{x'}$-O(R40), (CR38R39)$_{x'}$-CO—O(R40), O—(CR22R23)$_{x'}$-CO—O(R40), (CR22R23)$_{x'}$-N(R41)(R42), O—(CR38R39)$_{x'}$-N(R41)(R42), (CR38R39)$_{x'}$-CON(R41)(R42), O—(CR38R39)$_{x'}$-CON(R41)(R42), O—CO—N(R41)(R42), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R43)(R44);

x' is 0, 1, 2, 3, 4, 5, 6;

or

R7 and R8 or R8 and R9 or R9 and R10 together with the carbon atom which bears them form a monocyclic, 5- to 7-membered saturated, partly unsaturated or aromatic ring system whose individual members may be substituted by —CHR45-, —CR46R47-, =(C—R46)-, O, N or S; with the proviso that no two units from the group of —O—, N and —S— may be adjacent;

R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44 are each independently hydrogen, (C$_1$-C$_6$)-alkyl;

or

R11 and R12, R13 and R14, R15 and R16, R25 and 26, R27 and R28, R29 and R30, R31 and R32, R41 and 42, R43 and 44 each independently form, optionally together with the nitrogen atom to which they are bonded, a 5-6-membered ring which, apart from the nitrogen atom, may also include 0-1 further heteroatom from the group of NH, N—(C$_1$-C$_6$)-alkyl, oxygen and sulfur;

R45, R46, R47 are the same or different and are each F, Cl, Br, I, OH, CF$_3$, NO$_2$, CN, OCHF$_2$, OCF$_3$, SF$_5$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, O—(C$_2$-C$_4$)-haloalkyl, (C$_2$-C$_6$)-alkenyl, (C$_3$-C$_8$)-cycloalkyl, O—(C$_3$-C$_8$)-cycloalkyl, (C$_2$-C$_6$)-alkynyl, N(R134)(R135), SO$_2$—CH$_3$, COOH, COO—(C$_1$-C$_6$)-alkyl, CON(R136)(R137), N(R138)CO(R139), N(R140)SO$_2$(R141), CO(R142), (CR143R144)$_{x''}$-O(R145), (CR143R144)$_{x''}$-CO—O(R145), O—(CR143R144)$_{x''}$-CO—O(R145), (CR143R144)$_{x''}$-N(R146)(R147), O—(CR143R144)$_{x''}$-N(R146)(R147), (CR143R144)$_{x''}$-CON(R146)(R147), O—(CR143R144)$_{x''}$-CON(R146)(R147), O—CO—N(R146)(R147), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R148)(R149);

x" is independently 1, 2, 3, 4, 5, 6;

R134, R135, R136, R137, R138, R139, R140, R141, R142, R143, R144, R145, R146, R147, R148, R149 are the same or different and are each hydrogen, (C$_1$-C$_6$)-alkyl;

or R1 is preferably a radical of the formula Ia

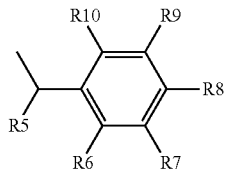

in which

R5 is hydrogen, CH$_3$, CH$_2$CH$_3$;

R6, R7, R8, R9, R10 are each independently hydrogen, F, Cl, Br, I, OH, CF$_3$, NO$_2$, CN, OCF$_3$, SCF$_3$, OCHF$_2$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, N(R11)(R12), SO$_2$—CH$_3$, SO$_2$—N(R13)(R14), COOH, COO—(C$_1$-C$_6$)-alkyl, CO(R21), (CR22R23)$_x$-O(R24), (CR22R23)$_x$-CO—O(R24), O—(CR22R23)$_x$-CO—O(R24), (CR22R23)$_x$-N(R25)(R26), O—(CR22R23)$_x$-N(R25)(R26), (CR22R23)$_x$-CON(R25)(R26);

x is independently 0, 1, 2, 3, 4;

or

R7 or R8 is (O)$_y$—(CH$_2$—)$_{y'}$—(O)$_{y''}$—(CH$_2$)$_{y'''}$-R100;

y, y" are each independently 0, 1;

y', y''' are each independently 1, 2, 3, 4, 5, 6;

R100 is a 4- to 10-membered mono- or bicyclic saturated, partly unsaturated or aromatic ring which may contain 1 to 4 heteroatoms selected from the group of oxygen, nitrogen and sulfur, where the ring system may additionally be mono- or polysubstituted by F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, (C$_2$-C$_6$)-alkenyl, (C$_2$-C$_6$)-alkynyl, N(R29)(R30), SO$_2$—CH$_3$, SF$_5$, COOH, COO—(C$_1$-C$_6$)-alkyl, CON(R31)(R32), N(R33)CO(R34), N(R35)SO$_2$(R36), CO(R37), (CR38R39)$_{x''}$-O(R40), (CR38R39)$_{x''}$-CO—O(R40), O—(CR22R23)$_{x''}$-CO—O(R40), (CR22R23)$_{x''}$-N(R41)(R42), O—(CR38R39)$_{x''}$-N(R41)(R42), (CR38R39)$_{x''}$-CON(R41)(R42), O—(CR38R39)$_{x''}$-CON(R41)(R42), O—CO—N(R41)(R42), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R43)(R44);

x" is independently 1, 2, 3, 4, 5, 6;

or

R7 and R8 or R8 and R9 or R9 and R10 together with the carbon atom which bears them form a monocyclic, 5- to 7-membered saturated, partly unsaturated or aromatic ring system whose individual members may be substituted by —CHR45-, —CR46R47-, =(C—R46)-, O, N or S; with the proviso that no two units from the group of —O—, N and —S— may be adjacent;

R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44 are each independently hydrogen, (C$_1$-C$_6$)-alkyl;

or

R11 and R12, R13 and R14, R15 and R16, R25 and 26, R27 and R28, R29 and R30, R31 and R32, R41 and 42, R43 and 44 each independently form, optionally together with the nitrogen atom to which they are bonded, a 5-6-membered ring which, apart from the nitrogen atom, may also include 0-1 further heteroatom from the group of NH, N—(C$_1$-C$_6$)-alkyl, oxygen and sulfur;

R45, R46, R47 are the same or different and are each F, Cl, Br, I, OH, CF$_3$, OCHF$_2$, OCF$_3$, SF$_5$, O—(C$_1$-C$_4$)-alkoxy-(C$_1$-C$_4$)-alkyl, S—(C$_1$-C$_6$)-alkyl, (C$_1$-C$_6$)-alkyl, SO$_2$—CH$_3$, COOH, COO—(C$_1$-C$_6$)-alkyl, CO(R142), (CR143R144)$_{x''}$-O(R145), (CR143R144)$_{x''}$-CO—O(R145), O—(CR143R144)$_{x''}$-CO—O(R145), (CR143R144)$_{x''}$-N(R146)(R147), O—(CR143R144)$_{x''}$-N(R146)(R147), (CR143R144)$_{x''}$-CON(R146)(R147), O—(CR143R144)$_{x''}$-CON(R146)(R147);

x" is independently 1, 2, 3, 4;

R134, R135, R136, R137, R138, R139, R140, R141, R142, R143, R144, R145, R146, R147, R148, R149
are the same or different and are each hydrogen, $(C_1-C_6)$-alkyl;

particular preference is given to a radical of the formula Ia

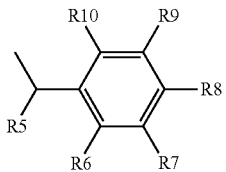

in which

R5 is hydrogen, $CH_3$;

R6, R7, R8, R9, R10
are each independently hydrogen, F, Cl, Br, $CF_3$, $OCF_3$, $SCF_3$, $OCHF_2$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $SO_2$—$CH_3$, $SO_2$—N(R13)(R14), COOH, COO—$(C_1-C_6)$-alkyl, $(CR22R23)_x$-O(R24), $(CR22R23)_x$-CO—O(R24), O—$(CR22R23)_x$-CO—O(R24), $(CR22R23)_x$-N(R25)(R26), O—$(CR22R23)_x$-N(R25)(R26), $(CR22R23)_x$-CON(R25)(R26);

x is independently 0, 1, 2, 3, 4;

or

R7 or R8 is

R100, —$CH_2$—R100, —$OCH_2$—R100, —$CH_2$—O—R100, —$CH_2$—O—$CH_2$—R100 or —O—$CH_2CH_2$—R100;

R100 is a 4- to 7-membered monocyclic saturated, partly unsaturated or aromatic ring which may contain 1 to 3 heteroatoms selected from the group of oxygen, nitrogen and sulfur, where the ring system may additionally be mono- or polysubstituted by F, Cl, Br, OH, $CF_3$, $OCF_3$, O—$(C_1-C_6)$-alkoxy-$(C_1-C_4)$-alkyl, S—$(C_1-C_6)$-alkyl, $(C_1-C_6)$-alkyl, $SO_2$—$CH_3$, COOH, COO—$(C_1-C_6)$-alkyl, N(R35)$SO_2$(R36), CO(R37), $(CR38R39)_{x'}$-O(R40), $(CR38R39)_{x'}$-CO—O(R40), O—$(CR22R23)_{x'}$-CO—O(R40), $(CR22R23)_{x'}$-N(R41)(R42), O—$(CR38R39)_{x'}$-N(R41)(R42), $(CR38R39)_{x'}$-CON(R41)(R42), O—$(CR38R39)_{x'}$-CON(R41)(R42);

x' is independently 1, 2, 3, 4;

or

R7 and R8 or R8 and R9 or R9 and R10 together with the carbon atom which bears them form
—O—$CH_2$—O—, —O—$CH_2$—$CH_2$—O—, —O—$CH_2$—$CH_2$—$CH_2$—O—, —O—$CF_2$—O— or —N($CH_3$)—N=N—;

R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42
are each independently hydrogen, $(C_1-C_6)$-alkyl;

or

R11 and R12, R13 and R14, R15 and R16, R25 and 26, R27 and R28, R29 and R30, R31 and R32, R41 and 42, R43 and 44
each independently form, optionally together with the nitrogen atom to which they are bonded, a 5-6-membered ring which, apart from the nitrogen atom, may also include 0-1 further heteroatom from the group of NH, N—$(C_1-C_6)$-alkyl, oxygen and sulfur.

In a further embodiment,

R1 is more preferably a radical of the formula Ia

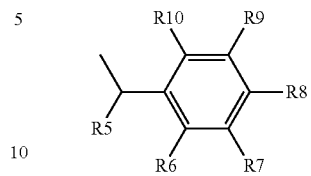

in which

R5 is hydrogen, $CH_3$, $CH_2CH_3$;

R6, R7, R8, R9, R10
are each independently hydrogen, F, Cl, Br, I, OH, $CF_3$, $NO_2$, CN, $OCF_3$, $SCF_3$, $OCHF_2$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, N(R11)(R12), $SO_2$—$CH_3$, $SO_2$—N(R13)(R14), COOH, COO—$(C_1-C_6)$-alkyl, CO(R21), $(CR22R23)_x$—O(R24), $(CR22R23)_x$—CO—O(R24), O—$(CR22R23)_x$-CO—O(R24), $(CR22R23)_x$-N(R25)(R26), O—$(CR22R23)_x$-N(R25)(R26), $(CR22R23)_x$-CON(R25)(R26);

with the proviso that at least one R6, R7, R8, R9, R10 radical is not hydrogen;

x is independently 0, 1, 2, 3, 4;

or

R7 or R8 is $(O)_{y''}$—$(CH_2$—$)_{y'}$—$(O)_{y'''}$—$(CH_2)_{y'''}$—R100;

y" are each independently 0, 1;

y', y''' are each independently 1, 2, 3, 4, 5, 6;

R100 is a 4- to 10-membered mono- or bicyclic saturated, partly unsaturated or aromatic ring which may contain 1 to 4 heteroatoms selected from the group of oxygen, nitrogen and sulfur, where the ring system may additionally be mono- or polysubstituted by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, $(C_2-C_6)$-alkenyl, $(C_2-C_6)$-alkynyl, N(R29)(R30), $SO_2$—$CH_3$, $SF_5$, COOH, COO—$(C_1-C_6)$-alkyl, CON(R31)(R32), N(R33)CO(R34), N(R35)$SO_2$(R36), CO(R37), $(CR38R39)_{x'}$-O(R40), $(CR38R39)_{x'}$-CO—O(R40), O—$(CR22R23)_{x'}$-CO—O(R40), $(CR22R23)_{x'}$-N(R41)(R42), O—$(CR38R39)_{x'}$-N(R41)(R42), $(CR38R39)_{x'}$-CON(R41)(R42), O—$(CR38R39)_{x'}$-CON(R41)(R42), O—CO—N(R41)(R42), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R43)(R44);

x' is independently 1, 2, 3, 4, 5, 6;

or

R7 and R8 or R8 and R9 or R9 and R10
together with the carbon atom which bears them form a monocyclic, 5- to 7-membered saturated, partly unsaturated or aromatic ring system whose individual members may be substituted by —CHR45-, —CR46R47-, =(C—R46)-, O, N or S; with the proviso that no two units from the group of —O—, N and —S— may be adjacent;

R11, R12, R13, R14, R15, R16, R17, R18, R19, R20, R21, R22, R23, R24, R25, R26, R27, R28, R29, R30, R31,

R32, R33, R34, R35, R36, R37, R38, R39, R40, R41, R42, R43, R44
are each independently hydrogen, $(C_1\text{-}C_6)$-alkyl;
or
R11 and R12, R13 and R14, R15 and R16, R25 and 26, R27 and R28, R29 and R30, R31 and R32, R41 and 42, R43 and 44
each independently form, optionally together with the nitrogen atom to which they are bonded, a 5-6-membered ring which, apart from the nitrogen atom, may also include 0-1 further heteroatom from the group of NH, N—$(C_1\text{-}C_6)$-alkyl, oxygen and sulfur;
R45, R46, R47 are the same or different and are each F, Cl, Br, I, OH, $CF_3$, $OCHF_2$, $OCF_3$, $SF_5$, O—$(C_1\text{-}C_6)$-alkyl, O—$(C_1\text{-}C_4)$-alkoxy-$(C_1\text{-}C_4)$-alkyl, S—$(C_1\text{-}C_6)$-alkyl, $SO_2$—$CH_3$, COOH, COO—$(C_1\text{-}C_6)$-alkyl, CO(R142), $(CR143R144)_{x''}$-O(R145), $(CR143R144)_{x''}$-CO—O(R145), O—$(CR143R144)_{x''}$-CO—O(R145), $(CR143R144)_{x''}$-N(R146)(R147), O—$(CR143R144)_{x''}$-N(R146)(R147), $(CR143R144)_{x''}$-CON(R146)(R147), O—$(CR143R144)_{x''}$-CON(R146)(R147);
x'' is independently 1, 2, 3, 4;
R134, R135, R136, R137, R138, R139, R140, R141, R142, R143, R144, R145, R146, R147, R148, R149
are the same or different and are each hydrogen, $(C_1\text{-}C_6)$-alkyl;
very particular preference is given to a radical of the formula Ia

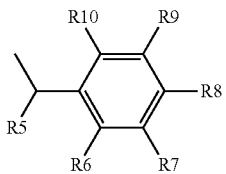

in which
R5 is hydrogen, $CH_3$;
R6, R7, R8, R9, R10
are each independently hydrogen, F, Cl, Br, $CF_3$, $OCF_3$, $SCF_3$, $OCHF_2$, O—$(C_1\text{-}C_6)$-alkyl, O—$(C_1\text{-}C_4)$-alkoxy-$(C_1\text{-}C_4)$-alkyl, S—$(C_1\text{-}C_6)$-alkyl, $(C_1\text{-}C_6)$-alkyl, $SO_2$—$CH_3$, $SO_2$—N(R13)(R14), COOH, COO—$(C_1\text{-}C_6)$-alkyl, $(CR22R23)_x$-O(R24), $(CR22R23)_x$-CO—O(R24), O—$(CR22R23)_x$-CO—O(R24), $(CR22R23)_x$-N(R25)(R26), O—$(CR22R23)_x$-N(R25)(R26), $(CR22R23)_x$-CON(R25)(R26);
with the proviso that at least one R6, R7, R8, R9, R10 radical is not hydrogen;
x is independently 0, 1, 2, 3, 4;
or
R7 or R8 is
R100, —$CH_2$—R100, —$OCH_2$—R100, —$CH_2$—O—R100, —$CH_2$—O—$CH_2$—R100 or —O—$CH_2CH_2$—R100;
R100 is a 4- to 7-membered monocyclic saturated, partly unsaturated or aromatic ring which may contain 1 to 3 heteroatoms selected from the group of oxygen, nitrogen and sulfur, where the ring system may additionally be mono- or polysubstituted by F, Cl, Br, OH, $CF_3$, $OCF_3$, O—$(C_1\text{-}C_6)$-alkyl, O—$(C_1\text{-}C_4)$-alkoxy-$(C_1\text{-}C_4)$-alkyl, S—$(C_1\text{-}C_6)$-alkyl, $(C_1\text{-}C_6)$-alkyl, $SO_2$—$CH_3$, COOH, COO—$(C_1\text{-}C_6)$-alkyl, $N(R35)SO_2(R36)$, CO(R37), $(CR38R39)_{x'}$-O(R40), $(CR38R39)_{x'}$-CO—O(R40), O—$(CR22R23)_x$-CO—O(R40), $(CR22R23)_{x'}$-N(R41)(R42), O—$(CR38R39)_{x'}$-N(R41)(R42), $(CR38R39)_{x'}$-CON(R41)(R42), O—$(CR38R39)_{x'}$-CON(R41)(R42);
x' is independently 1, 2, 3, 4;
or
R7 and R8 or R8 and R9 or R9 and R10
together with the carbon atom which bears them form —O—$CH_2$—O—, —O—$CH_2$—$CH_2$—O—, —O—$CH_2$—$CH_2$—$CH_2$—O—, —O—$CF_2$—O— or —N($CH_3$)—N=N—;
R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42
are each independently hydrogen, $(C_1\text{-}C_6)$-alkyl;
or
R11 and R12, R13 and R14, R15 and R16, R25 and 26, R27 and R28, R29 and R30, R31 and R32, R41 and 42, R43 and 44
each independently form, optionally together with the nitrogen atom to which they are bonded, a 5-6-membered ring which, apart from the nitrogen atom, may also include 0-1 further heteroatom from the group of NH, N—$(C_1\text{-}C_6)$-alkyl, oxygen and sulfur.
In a further embodiment,
R1 is preferably a radical of the formula Ib

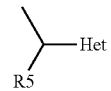

in which:
R5 is hydrogen, $CH_3$, $CH_2CH_3$;
Het is a 4- to 10-membered mono- or bicyclic aromatic ring containing 1 to 4 heteroatoms selected from the group of oxygen, nitrogen and sulfur, where the ring system may additionally be mono- or polysubstituted independently by F, Cl, Br, I, OH, $CF_3$, $NO_2$, CN, $OCF_3$, $OCHF_2$, O—$(C_1\text{-}C_6)$-alkyl, O—$(C_1\text{-}C_4)$-alkoxy-$(C_1\text{-}C_4)$-alkyl, S—$(C_1\text{-}C_6)$-alkyl, $(C_1\text{-}C_6)$-alkyl, $(C_2\text{-}C_6)$-alkenyl, N(R48)(R49), $SO_2$—$CH_3$, $SO_2$—N(R50)(R51), $SCF_3$, COOH, COO—$(C_1\text{-}C_6)$-alkyl, N(R54)CO(R55), N(R56)$SO_2$(R57), CO(R58), $(CR59R60)_{x'''}$-O(R61), $(CR59R60)_{x'''}$-CO—O(R61), O—$(CR59R60)_{x'''}$-CO—O(R61), $(CR59R60)_{x'''}$-N(R62)(R63), O—$(CR59R60)_{x'''}$-N(R62)(R63), $(CR59R60)_{x'''}$-CON(R62)(R63), O—$(CR59R60)_{x'''}$-CON(R62)(R63), O—CO—N(R62)(R63), O—CO—$(C_1\text{-}C_6)$-alkylene-CO—O—$(C_1\text{-}C_6)$-alkyl, O—CO—$(C_1\text{-}C_6)$-alkylene-CO—OH, O—CO—$(C_1\text{-}C_6)$-alkylene-CO—N(R64)(R65),
or $(O)_y$—$(CH_2)_{y'}$—$(O)_{y''}$—$(CH_2)_{y'''}$-R101,
x''' is independently 1, 2, 3, 4;
y, y'' are each independently 0, 1;
y', y''' are each independently 0, 1, 2, 3, 4;
R101 is a 4- to 10-membered mono- or bicyclic saturated, partly unsaturated or aromatic ring which may contain 1 to 4 heteroatoms selected from the group of oxygen, nitrogen and sulfur, where the ring system may additionally be mono- or polysubstituted by F, Cl, Br, I, OH, $CF_3$, $NO_2$, CN, $OCHF_2$, $OCF_3$, O—$(C_1\text{-}C_6)$-alkyl, O—$(C_1\text{-}C_4)$-alkoxy-$(C_1\text{-}C_4)$-alkyl, S—$(C_1\text{-}C_6)$-alkyl, $(C_1\text{-}C_6)$-alkyl, $(C_2\text{-}C_4)$-haloalkyl, $(C_2\text{-}C_6)$-alkenyl, $(C_3\text{-}C_8)$-cycloalkyl, O—$(C_3\text{-}C_8)$-cycloalkyl, $(C_2\text{-}C_6)$-alkynyl, N(R66)(R67), SO$_2$—CH$_3$, SF$_5$, COOH, COO—(C$_1$-C$_6$)-alkyl, CON(R68)(R69), (C), N(R70)CO(R71), N(R72)SO$_2$(R73), CO(R74), (CR75R76)$_{x''''}$—O (R77R75R76)$_{x''''}$—CO—O(R77), O—(CR75R76)$_{x''''}$—CO—O(R77), (CR75R76)$_{x''''}$—N(R78)(R79), O—(CR75R76)$_{x''''}$-N(R78)(R79), (CR75R76)$_{x''''}$—CON(R78)(R79), O—(CR75R76)$_{x''''}$-CON(R78)(R79), O—CO—N(R78)(R79), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R80)(R81);

x'''' is independently 1, 2, 3, 4, 5, 6;

R48, R49, R50, R51, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81 are each independently hydrogen, (C$_1$-C$_6$)-alkyl;

or

R48 and R49, R50 and R51, R52 and R53, R62 and R63, R64 and R65, R66 and R67, R68 and R69, R78 and R79, R80 and R81 each independently form, optionally together with the nitrogen atom to which they are bonded, a 5-6-membered ring which, apart from the nitrogen atom, may also include 0-1 further heteroatom from the group of NH, N—(C$_1$-C$_6$)-alkyl, oxygen and sulfur;

particular preference is given to a radical of the formula Ib

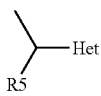

Ib in which:

R5 is hydrogen, CH$_3$;

Het is selected from the group of pyridine, pyrazole, imidazole, oxazole, oxadiazole, benzothiophene, imidazo[2,1-b]thiazole, where Het may additionally be mono- or polysubstituted independently by F, Cl, Br, CF$_3$, OCF$_3$, OCHF$_2$, O—(O$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, SO$_2$—CH$_3$, SO$_2$—N(R50)(R51), COOH, COO—(C$_1$-C$_6$)-alkyl, N(R56)SO$_2$(R57), CO(R58), (CR59R60)$_{x'''}$-O(R61), (CR59R60)$_{x'''}$-CO—O(R61), O—(CR59R60)$_{x'''}$-CO—O(R61), (CR59R60)$_{x'''}$-N(R62)(R63), O—(CR59R60)$_{x'''}$-N(R62)(R63), (CR59R60)$_{x'''}$-CON(R62)(R63), O—(CR59R60)$_{x'''}$-CON(R62)(R63), O—CO—N(R62)(R63), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R64)(R65); or (O)$_{y'}$—(CH$_2$—)$_{y'}$—(O)$_{y''}$—(CH$_2$)$_{y'''}$—R101, x''' is independently 1, 2, 3, 4;

y, y'' are each independently 0, 1;

y', y''' are each independently 0, 1, 2;

R101 is a 4- to 10-membered mono- or bicyclic saturated, partly unsaturated or aromatic ring which may contain 1 to 4 heteroatoms selected from the group of oxygen, nitrogen and sulfur, where the ring system may additionally be mono- or polysubstituted by F, Cl, Br, I, OH, CF$_3$, NO$_2$, CN, OCHF$_2$, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, (C$_2$-C$_6$)-alkenyl, (C$_3$-C$_8$)-cycloalkyl, O—(C$_3$-C$_8$)-cycloalkyl, (C$_2$-C$_6$)-alkynyl, N(R66)(R67), SO$_2$—CH$_3$, SF$_5$, COOH, COO—(C$_1$-C$_6$)-alkyl, CON(R68)(R69), (C), N(R70)CO(R71), N(R72)SO$_2$(R73), CO(R74), (CR75R76)$_{x''''}$-O (R77R75R76)$_{x''''}$—CO—O(R77), O—(CR75R76)$_{x''''}$-CO—O(R77), (CR75R76)$_{x''''}$-N(R78)(R79), O—(CR75R76)$_{x''''}$-N(R78)(R79), (CR75R76)$_{x''''}$-CON(R78)(R79), O—(CR75R76)$_{x''''}$-CON(R78)(R79), O—CO—N(R78)(R79), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R80)(R81);

x'''' is independently 1, 2, 3, 4, 5, 6;

R48, R49, R50, R51, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81 are each independently hydrogen, (C$_1$-C$_6$)-alkyl;

or

R48 and R49, R50 and R51, R52 and R53, R62 and R63, R64 and R65, R66 and R67, R68 and R69, R78 and R79, R80 and R81 each independently form, optionally together with the nitrogen atom to which they are bonded, a 5-6-membered ring which, apart from the nitrogen atom, may also include 0-1 further heteroatom from the group of NH, N—(C$_1$-C$_6$)-alkyl, oxygen and sulfur.

In a further embodiment,

R1 is preferably a radical of the formula Ic

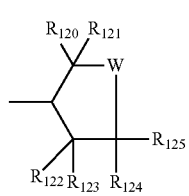

Ic in which

W is —C(R126)(R127)-, —C(R126)(R127)-C(R128)(R129)-, —C(R126)(R127)-O—;

R120, R121, R122, R123, R124, R125, R126, R127, R128, R129 are the same or different and are each hydrogen, F, Cl, Br, I, OH, CF$_3$, NO$_2$, CN, OCHF$_2$, OCF$_3$, SF$_5$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, O—(C$_2$-C$_4$)-haloalkyl, (C$_2$-C$_6$)-alkenyl, (C$_3$-C$_8$)-cycloalkenyl, (C$_2$-C$_6$)-alkynyl, N(R90)(R91), SO$_2$—CH$_3$, COOH, COO—(C$_1$-C$_6$)-alkyl, CON(R92)(R93), N(R94)CO(R95), N(R96)SO$_2$(R97), CO(R98), (CR99R102)$_z$-O(R103), (CR99R76)$_z$-CO—O(R103), O—(CR99R102)$_z$-CO—O(R103), (CR99R102)$_z$-N(R104)(R105), O—(CR99R102)$_z$-N(R104)(R105), (CR99R102)$_z$-CON(R104)(R105), O—(CR99R102)$_z$-CON(R104)(R105), O—CO—N(R104)(R105), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R106)(R107);

z is independently 1, 2, 3, 4, 5, 6;

R90, R91, R92, R93, R94, R95, R96, R97, R98, R99, R102, R103, R104, R105, R106, R107 are the same or different and are each hydrogen, (C$_1$-C$_6$)-alkyl;

or

R120 and R126 or R121 and R127 together with the carbon atom which bears them form a monocyclic, 5- or 6-membered saturated, partly unsaturated or aromatic ring system whose individual members may be substituted by —CHR130-, —CR131R132-, =(C—R133)-;
or
R122 and R124, or R123 and R125 together with the carbon atom which bears them form a monocyclic, 5- or 6-membered saturated, partly unsaturated or aromatic ring system whose individual members may be substituted by —CHR130-, —CR131R132-, =(C—R133)-;
R130, R131, R132, R133 are the same or different and are each F, Cl, Br, I, OH, $CF_3$, $NO_2$, CN, $OCHF_2$, $OCF_3$, $SF_5$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_2$-$C_6$)-alkynyl, N(R160)(R161), $SO_2$—$CH_3$, COOH, COO—($C_1$-$C_6$)-alkyl, CON(R162)(R163), N(R164)CO(R165), N(R166)$SO_2$(R167), CO(R168), (CR169R170)$_z$-O(R171), (CR169R170)$_z$-CO—O(R77), O—(CR169R170)$_z$-CO—O(R171), (CR169R170)$_z$-N(R172)(R173), O—(CR169R170)$_z$-N(R172)(R173), (CR169R170)$_z$-CON(R172)(R173), O—(CR169R170)$_z$-CON(R172)(R173), O—CO—N(R172)(R173), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R172)(R173);
z' is independently 1, 2, 3, 4, 5, 6;
R160, R161, R162, R163, R164, R165, R166, R167, R168, R169, R170, R171, R172, R173
are the same or different and are each hydrogen, ($C_1$-$C_6$)-alkyl;
or
R160 and R161, R162 and R163, R172 and R173 each independently form, optionally together with the nitrogen atom to which they are bonded, a 5-6-membered ring which, apart from the nitrogen atom, may also include 0-1 further heteroatom from the group of NH, N—($C_1$-$C_6$)-alkyl, oxygen and sulfur;
more preferably a radical of the formula Ic:

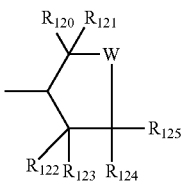

in which
W is —C(R126)(R127)-, —C(R126)(R127)-C(R128)(R129)-, —C(R126)(R127)-O—;
R120, R121, R122, R123, R124, R125, R126, R127, R128, R129 R120, R121, R126, R127, R128, R129 are the same or different and are each hydrogen, $CH_3$, oxo;
are the same or different and are each hydrogen, F, Cl, Br, I, OH, $CF_3$, $NO_2$, CN, $OCHF_2$, $OCF_3$, $SF_5$, O—($C_1$-$C_6$)-alkyl, O—($C_1$-$C_4$)-alkoxy-($C_1$-$C_4$)-alkyl, S—($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkenyl, ($C_2$-$C_6$)-alkynyl, N(R90)(R91), $SO_2$—$CH_3$, COOH, CON(R92)(R93), N(R94)CO(R95), N(R96)$SO_2$(R97), CO(R98), (CR99R102)$_z$-O(R103), (CR99R76)$_z$-CO—O(R103), O—(CR99R102)$_z$-CO—O(R103), (CR99R102)$_z$-N(R104)(R105), O—(CR99R102)$_z$-N(R104)(R105), (CR99R102)$_z$-CON(R104)(R105), O—(CR99R102)$_z$-CON(R104)(R105), O—CO—N(R104)(R105), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R106)(R107);
z is independently 1, 2, 3, 4, 5, 6;
R90, R91, R92, R93, R94, R95, R96, R97, R98, R99, R102, R103, R104, R105, R106, R107
are the same or different and are each hydrogen, ($C_1$-$C_6$)-alkyl;
or
R120 and R126 or R121 and R127 together with the carbon atom which bears them form a monocyclic, 5- or 6-membered saturated, partly unsaturated or aromatic ring system whose individual members may be substituted by —CHR130-, —CR131R132-, =(C—R133)-;
or
R122 and R124 together with the carbon atom which bears them form a monocyclic, 6-membered aromatic ring system whose individual members may be substituted by =(C—R133)-;
R133 are the same or different and are each F, Cl, Br, I, OH, $CF_3$, $NO_2$, CN, $OCHF_2$, $OCF_3$, $SF_5$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_2$-$C_6$)-alkynyl, N(R160)(R161), $SO_2$—$CH_3$, COOH, COO—($C_1$-$C_6$)-alkyl, CON(R162)(R163), N(R164)CO(R165), N(R166)$SO_2$(R167), CO(R168), (CR169R170)$_z$-O(R171), (CR169R170)$_z$-CO—O(R77), O—(CR169R170)$_z$-CO—O(R171), (CR169R170)$_z$-N(R172)(R173), O—(CR169R170)$_z$-N(R172)(R173), (CR169R170)$_z$-CON(R172)(R173), O—(CR169R170)$_z$-CON(R172)(R173), O—CO—N(R172)(R173), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R172)(R173);
z" is independently 1, 2, 3, 4, 5, 6;
R160, R161, R162, R163, R164, R165, R166, R167, R168, R169, R170, R171, R172, R173
are the same or different and are each hydrogen, ($C_1$-$C_6$)-alkyl;
or
R160 and R161, R162 and R163, R172 and R173 each independently form, optionally together with the nitrogen atom to which they are bonded, a 5-6-membered ring which, apart from the nitrogen atom, may also include 0-1 further heteroatom from the group of NH, N—($C_1$-$C_6$)-alkyl, oxygen and sulfur;
most preferably a radical of the formula Ic:

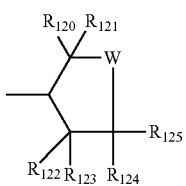

in which
W is —C(R126)(R127)-, —C(R126)(R127)-C(R128)(R129)-, —C(R126)(R127)-O—;
R120, R121, R122, R123, R124, R125, R126, R127, R128, R129 R120, R121, R126, R127, R128, R129 are the same or different and are each hydrogen, $(C_1-C_6)$-alkyl, oxo, COO—$(C_1-C_6)$-alkyl;

or

R122 and R124 together with the carbon atom which bears them form a monocyclic, 6-membered aromatic ring system whose individual members may be substituted by =(C—R133)-;

R133 are the same or different and are each F, Cl, Br, I, OH, $CF_3$, $NO_2$, CN, $OCHF_2$, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R160)(R161), $SO_2$—$CH_3$, COOH, COO—$(C_1-C_6)$-alkyl, CON(R162)(R163), N(R164)CO(R165), N(R166)$SO_2$(R167), CO(R168), $(CR169R170)_{z'}$-O(R171), $(CR169R170)_{z'}$-CO—O(R77), O—$(CR169R170)_{z'}$-CO—O(R171), $(CR169R170)_{z'}$-N(R172)(R173), O—$(CR169R170)_{z'}$-N(R172)(R173), $(CR169R170)_{z'}$-CON(R172)(R173), O—$(CR169R170)_{z'}$-CON(R172)(R173), O—CO—N(R172)(R173), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R172)(R173);

z' is independently 1, 2, 3, 4, 5, 6;

R160, R161, R162, R163, R164, R165, R166, R167, R168, R169, R170, R171, R172, R173 are the same or different and are each hydrogen, $(C_1-C_6)$-alkyl;

or

R160 and R161, R162 and R163, R172 and R173 each independently form, optionally together with the nitrogen atom to which they are bonded, a 5-6-membered ring which, apart from the nitrogen atom, may also include 0-1 further heteroatom from the group of NH, N—$(C_1-C_6)$-alkyl, oxygen and sulfur.

In a further preferred embodiment,

R2, R3, R4 are the same or different and are each hydrogen, F, Cl, $CF_3$, $OCHF_2$, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_3-C_8)$-cycloalkyl, O—$(C_3-C_8)$-cycloalkyl, phenyl, N(R200)(R201), $SO_2$—$CH_3$, COO—$(C_1-C_6)$-alkyl, CON(R202)(R203), N(R204)CO(R205), N(R206)$SO_2$(R207), CO(R208), $(CR209R210)_{z''}$-O(R211), $(CR209R210)_{z''}$-CO—O(R211), O—$(CR209R210)_{z''}$-CO—O(R211), $(CR209R210)_{z''}$-N(R212)(R213), O—$(CR209R210)_{z''}$-N(R212)(R213), $(CR209R210)_{z''}$-CON(R212)(R213), O—CO—$(C_1-C_6)$-alkylene-CO—O—$(C_1-C_6)$-alkyl;

z'' is independently 1, 2, 3;

R200, R201, R202, R203, R204 R205, R206, R207, R208, R209, R210, R211, R212, R213 are the same or different and are each hydrogen, $(C_1-C_6)$-alkyl;

or

R200 and R201, R202 and R203, R212 and R213 each independently form, optionally together with the nitrogen atom to which they are bonded, a 5-6-membered ring which, apart from the nitrogen atom, may also include 0-1 further heteroatom from the group of NH, N—$(C_1-C_6)$-alkyl, oxygen and sulfur;

more preferably,

R2, R3, R4 are the same or different and are each hydrogen, F, Cl, $CF_3$, $OCHF_2$, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_3-C_8)$-cycloalkyl, O—$(C_3-C_8)$-cycloalkyl, phenyl, $SO_2$—$CH_3$, COO—$(C_1-C_6)$-alkyl, $(CR209R210)_{z''}$-O(R211), $(CR209R210)_{z''}$-CO—O(R211), O—$(CR209R210)_{z''}$-CO—O(R211), $(CR209R210)_{z''}$-N(R212)(R213);

z'' is independently 1, 2, 3;

R209, R210, R211, R212, R213 are the same or different and are each hydrogen, $(C_1-C_6)$-alkyl;

most preferably,

R2 is hydrogen, —$(C_1-C_6)$-alkyl, $(C_3-C_8)$-cycloalkyl or phenyl;

R3 is hydrogen;

R4 is hydrogen or —$(C_1-C_6)$-alkyl.

Very especially preferably,

R2 is hydrogen, methyl or phenyl;

R3 is hydrogen;

R4 is hydrogen or methyl.

The inventive compounds of the formula I have a surprising inhibiting effect on endothelial lipase (EL). HDL, which has antiatherosclerotic action, is the preferred substrate for EL. Lowering of the HDL level leads to progression of atherosclerosis and sequelae thereof, such as coronary cardiac disorders, and additionally promotes the occurrence of metabolic syndrome and diabetes, a sequela thereof. Inhibition of EL should thus generally lead to prevention of atherosclerotic disorders and, in patients at increased risk of diabetes, indirectly reduce the probability of illness.

It has also been found that the inhibiting action of the inventive compounds of the formula I is selective compared to other lipases.

Compared to prior art compounds, the inventive compounds have improved properties. More particularly, chemical stability in solution and in blood plasma and with respect to liver enzymes has been significantly improved, which further improves the suitability of the inventive compounds as medicaments. Such compounds are particularly suitable for treatment and/or prevention of 1. Dyslipidemias and sequelae thereof, for example atherosclerosis, coronary heart disease, cerebrovascular disorders etc., especially (but not limited to) those characterized by one or more of the following factors:
   high plasma triglyceride concentrations, high postprandial plasma triglyceride concentrations
   low HDL cholesterol concentration
   low ApoA lipoprotein concentrations
   high LDL cholesterol concentrations
   small dense LDL cholesterol particles
   high ApoB lipoprotein concentrations
2. Various other conditions which may be associated with metabolic syndrome, such as:
   adiposity (obesity), including abdominal adiposity
   thromboses, hypercoagulable and prothrombotic stages (arterial and venous)
   high blood pressure
   heart failure, for example (but not limited to) the state following myocardial infarction, hypertensive heart disease or cardiomyopathy
   diabetes mellitus, especially type 2 diabetes including the prevention of the sequelae associated therewith (hyperglycemia, glucose intolerance, loss of pancreatic β cells, macro- and microvascular disorders
3. Further disorders or conditions involving, for example, inflammation reactions or cell differentiation:
   atherosclerosis, for example (but not limited to) coronary sclerosis including angina pectoris or myocardial infarction, stroke
   vascular restenosis or reocclusion
   chronic inflammatory bowel disorders, for example Crohn's disease and ulcerative colitis
   pancreatitis
   other inflammatory conditions retinopathy
adipose cell tumors
lipomatous carcinomas, for example liposarcoma
solid tumors and neoplasias, for example (but not limited to) carcinomas of the gastrointestinal tract, of the liver, of the biliary tract and of the pancreas, endocrine tumors, carcinomas of the lung, of the kidney and urinary tract, of the genital tract, prostate carcinomas etc.
acute and chronic myeloproliferative disorders and lymphoma
angiogenesis
neurodegenerative disorders
Alzheimer's disease
multiple sclerosis
Parkinson's disease
erythematosquamous dermatoses, for example psoriasis
acne vulgaris
other skin disorders and dermatological conditions modulated by PPAR
eczema and neurodermitis
dermatitis, for example seborrhoic dermatitis or photodermatitis
keratitis and keratoses, for example seborrhoic keratoses, senile keratoses, actinic keratosis, photoinduced keratoses or keratosis follicularis
keloids and keloid prophylaxis
warts, including condylomata or condylomata acuminata
human papilloma viral (HPV) infections, for example venereal papillomata, viral warts, for example molluscum contagiosum, leukoplakia
papular dermatoses, for example lichen planus
skin cancer, for example basal cell carcinomas, melanomas or cutaneous T cell lymphomas
localized, benign epidermal tumors, for example keratoderma, epidermal naevi
chillblains
high blood pressure
syndrome X
polycystic ovary syndrome (PCOS)
asthma
osteoarthritis
lupus erythematodes (LE) or inflammatory rheumatic disorders, for example rheumatoid arthritis
vasculitis
wasting (cachexia)
gout
ischemia/reperfusion syndrome
acute respiratory distress syndrome (ARDS) ("shock lung")

Formulations

The amount of an inventive compound required to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, 0.1 ng to 10 mg, typically 1 ng to 10 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 0.05 to 1000 mg, typically from 0.5 to 600 mg. For treatment of the abovementioned conditions, the compounds of the formula I themselves may be used as the compound, but they are preferably present with a compatible carrier in the form of a pharmaceutical composition. The carrier must of course be acceptable in the sense that it is compatible with the other constituents of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including further inventive compounds. The inventive pharmaceutical compositions can be produced by one of the known pharmaceutical methods, which essentially involve mixing the ingredients with pharmacologically acceptable carriers and/or excipients.

Inventive pharmaceutical compositions are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations are also within the scope of the invention. Preference is given to acid- and gastric juice-resistant formulations. Suitable gastric juice-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical formulations for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. For example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the pulverulent compound moistened with an inert liquid diluent in a suitable machine.

Pharmaceutical compositions suitable for peroral (sublingual) administration include lozenges which contain a compound of formula I with a flavoring, typically sucrose, and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable inventive compositions generally contain from 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

The compounds of the formula I are notable for favorable effects on lipid metabolism disorders. They have a positive influence on the ratio of HDL to LDL and increase particularly the HDL level, and are suitable for prevention and treatment of dyslipidemias and metabolic syndrome and the various sequelae thereof, such as atherosclerosis, coronary heart disorders, heart failure, adiposity and diabetes.

Combinations with Other Medicaments

The inventive compounds can be administered alone or in combination with one or more further pharmacologically active substances which have, for example, beneficial effects on metabolic disturbances or disorders frequently associated therewith.

They can be combined with the inventive compounds of the formula I, in particular for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Further suitable active ingredients for the combination products are:

All antidiabetics mentioned in the Rote Liste 2007, chapter 12; all weight-reducing agents/appetite suppressants mentioned in the Rote Liste 2007, chapter 1; all diuretics mentioned in the Rote Liste 2007, chapter 36; all lipid-lowering agents mentioned in the Rote Liste 2007, chapter 58. Most of the active ingredients mentioned hereinafter are disclosed in the USP Dictionary of USAN and International Drug Names, US Pharmacopeia, Rockville 2006.

Antidiabetics include insulin and insulin derivatives, for example Lantus® (see www.lantus.com) or HMR 1964 or Levemir® (insulin detemir), Humalog® (Insulin Lispro), Humulin®, VIAject™, SuliXen®, or those as described in WO2005005477 (Novo Nordisk), fast-acting insulins (see U.S. Pat. No. 6,221,633), inhalable insulins, for example Exubera®, Nasulin™, or oral insulins, for example IN-105 (Nobex) or Oral-lyn™ (Generex Biotechnology), or Technosphere® insulin (MannKind) or Cobalamin™ oral insulin or insulins as described in WO2007128815, WO2007128817, WO2008034881, WO2008049711 or insulins which can be administered transdermally;

GLP-1 derivatives and GLP-1 agonists, for example exenatide or specific formulations thereof, as described, for example, in WO2008061355, liraglutide, taspoglutide (R-1583), albiglutide, lixisenatide or those which have been disclosed in WO 98/08871, WO2005027978, WO2006037811, WO2006037810 by Novo Nordisk A/S, in WO 01/04156 by Zealand or in WO 00/34331 by Beaufour-Ipsen, pramlintide acetate (Symlin; Amylin Pharmaceuticals), AVE-0010, BIM-51077 (R-1583, ITM-077), PC-DAC:Exendin-4 (an exendin-4 analog which is bonded covalently to recombinant human albumin), CVX-73, CVX-98 and CVx-96 (GLP-1 analogs which are bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists, as described, for example, in D. Chen et al., Proc. Natl. Acad. Sci. USA 104 (2007) 943, those as described in WO2006124529, WO2007124461, WO2008062457, WO2008082274, WO2008101017, WO2008081418, WO2008112939, WO2008112941, WO2008113601, WO2008116294, WO2008116648, WO2008119238, peptides, for example obinepitide (TM-30338), amylin receptor agonists, as described, for example, in WO2007104789, analogs of the human GLP-1, as described in WO2007120899, WO2008022015, WO2008056726, and orally active hypoglycemic ingredients.

Antidiabetics also include agonists of the glucose-dependent insulinotropic polypeptide (GIP) receptor, as described, for example, in WO2006121860.

Antidiabetics also include the glucose-dependent insulinotropic polypeptide (GIP), and also analogous compounds, as described, for example, in WO2008021560.

Antidiabetics also include analogs and derivatives of fibroblast growth factor 21 (FGF-21).

The orally active hypoglycemic ingredients preferably include
sulfonylureas,
biguanidines,
meglitinides,
oxadiazolidinediones,
thiazolidinediones,
PPAR and RXR modulators,
glucosidase inhibitors,
inhibitors of glycogen phosphorylase,
glucagon receptor antagonists,
glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists,
potassium channel openers, for example pinacidil, cromakalim, diazoxide, or those as described in R. D. Carr et al., Diabetes 52, 2003, 2513.2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 by Novo Nordisk A/S, active ingredients which act on the ATP-dependent potassium channel of the beta cells,
  inhibitors of dipeptidyl peptidase-IV (DPP-IV),
  insulin sensitizers,
  inhibitors of liver enzymes involved in stimulating gluconeogenesis and/or glycogenolysis,
  modulators of glucose uptake, of glucose transport and of glucose reabsorption,
  modulators of sodium-dependent glucose transporter 1 or 2 (SGLT1, SGLT2),
  inhibitors of 11-beta-hydroxysteroid dehydrogenase-1 (11β-HSD1),
  inhibitors of protein tyrosine phosphatase-1B (PTP-1B),
  nicotinic acid receptor agonists,
  inhibitors of hormone-sensitive or endothelial lipases,
  inhibitors of acetyl-CoA carboxylase (ACC1 and/or ACC2) or
  inhibitors of GSK-3 beta.

Also included are compounds which modify the lipid metabolism, such as active antihyperlipidemic ingredients and active antilipidemic ingredients, HMG-CoA reductase inhibitors,
  farnesoid X receptor (FXR) modulators,
  fibrates,
  cholesterol absorption inhibitors,
  CETP inhibitors,
  bile acid absorption inhibitors,
  MTP inhibitors,
  estrogen receptor gamma agonists (ERRγ agonists),
  sigma-1 receptor antagonists,
  antagonists of the somatostatin 5 receptor (SST5 receptor);
  compounds which reduce food intake, and
  compounds which increase thermogenesis.

In one embodiment of the invention, the compound of the formula I is administered in combination with insulin.

In one embodiment, the compound of the formula I is administered in combination with an active ingredient which acts on the ATP-dependent potassium channel of the beta cells, for example sulfonylureas, for example tolbutamide, glibenclamide, glipizide, gliclazide or glimepiride.

In one embodiment, the compound of the formula I is administered in combination with a tablet which comprises both glimepiride, which is released rapidly, and metformin, which is released over a longer period (as described, for example, in US2007264331, WO2008050987, WO2008062273).

In one embodiment, the compound of the formula I is administered in combination with a biguanide, for example metformin.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In a further embodiment, the compound of the formula I is administered in combination with antidiabetic compounds, as described in WO2007095462, WO2007101060, WO2007105650.

In a further embodiment, the compound of the formula I is administered in combination with antihypoglycemic compounds, as described in WO2007137008, WO2008020607.

In one embodiment, the compound of the formula I is administered in combination with a thiazolidinedione, for example troglitazone, ciglitazone, pioglitazone, rosiglitazone or the compounds disclosed in WO 97/41097 by Dr. Reddy's Research Foundation, especially 5-[[4-[(3,4-dihydro-3-methyl-4-oxo-2-quinazolinylmethoxy]phenyl]methyl]-2,4-thiazolidinedione.

In one embodiment of the invention, the compound of the formula I is administered in combination with a PPAR gamma agonist, for example rosiglitazone, pioglitazone, JTT-501, GI 262570, R-483, CS-011 (rivoglitazone), DRL-17564, DRF-2593 (balaglitazone), INT-131, T-2384, or those as described in WO2005086904, WO2007060992, WO2007100027, WO2007103252, WO2007122970, WO2007138485, WO2008006319, WO2008006969, WO2008010238, WO2008017398, WO2008028188, WO2008066356, WO2008084303, WO2008089461-WO2008089464, WO2008093639, WO2008096769, WO2008096820, WO2008096829, US2008194617, WO2008099944, WO2008108602, WO2008109334, WO2008126731, WO2008126732.

In one embodiment of the invention, the compound of the formula I is administered in combination with Competact™, a solid combination of pioglitazone hydrochloride with metformin hydrochloride.

In one embodiment of the invention, the compound of the formula I is administered in combination with Tandemact™, a solid combination of pioglitazone with glimepiride.

In a further embodiment of the invention, the compound of the formula I is administered in combination with a solid combination of pioglitazone hydrochloride with an angiotensin II agonist, for example TAK-536.

In one embodiment of the invention, the compound of the formula I is administered in combination with a PPAR alpha agonist or mixed PPAR alpha/PPAR delta agonist, for example GW9578, GW-590735, K-111, LY-674, KRP-101, DRF-10945, LY-518674, CP-900691, BMS-687453, BMS-711939, or those as described in WO2001040207, WO2002096894, WO2005097076, WO2007056771, WO2007087448, WO2007089667, WO2007089557, WO2007102515, WO2007103252, JP2007246474, WO2007118963, WO2007118964, WO2007126043, WO2008006043, WO2008006044, WO2008012470, WO2008035359, WO2008087365, WO2008087366, WO2008087367, WO2008117982.

In one embodiment of the invention, the compound of the formula I is administered in combination with a mixed PPAR alpha/gamma agonist, for example naveglitazar, LY-510929, ONO-5129, E-3030, AVE 8042, AVE 8134, AVE 0847, CKD-501 (lobeglitazone sulfate), MBX-213, KY-201, or as described in WO 00/64888, WO 00/64876, WO03/020269, WO2004024726, WO2007099553, US2007276041, WO2007085135, WO2007085136, WO2007141423, WO2008016175, WO2008053331, WO2008109697, WO2008109700, WO2008108735, or in J. P. Berger et al., TRENDS in Pharmacological Sciences 28(5), 244-251, 2005.

In one embodiment of the invention, the compound of the formula I is administered in combination with a PPAR delta agonist, for example GW-501516, or as described in WO2006059744, WO2006084176, WO2006029699, WO2007039172-WO2007039178, WO2007071766, WO2007101864, US2007244094, WO2007119887, WO2007141423, US2008004281, WO2008016175, WO2008066356, WO2008071311, WO2008084962, US2008176861.

In one embodiment of the invention, the compound of the formula I is administered in combination with a pan-SP- PARM (selective PPAR modulator alpha, gamma, delta), for example GFT-505, or those as described in WO2008035359.

In one embodiment, the compound of the formula I is administered in combination with metaglidasen or with MBX-2044 or other partial PPAR gamma agonists/antagonists.

In one embodiment, the compound of the formula I is administered in combination with an α-glucosidase inhibitor, for example miglitol or acarbose, or those as described, for example, in WO2007114532, WO2007140230, US2007287674, US2008103201, WO2008065796, WO2008082017.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932, WO2008062739, WO2008099000, WO2008113760.

In one embodiment, the compound of the formula I is administered in combination with glucagon receptor antagonists, for example A-770077 or NNC-25-2504 or as described in WO2004100875, WO2005065680, WO2006086488, WO2007047177, WO2007106181, WO2007111864, WO2007120270, WO2007120284, WO2007123581, WO2007136577, WO2008042223, WO2008098244.

In a further embodiment, the compound of the formula I is administered in combination with an antisense compound, e.g. ISIS-325568, which inhibits the production of the glucagon receptor.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847, WO2007061923, WO2007075847, WO2007089512, WO2007104034, WO2007117381, WO2007122482, WO2007125103, WO2007125105, US2007281942, WO2008005914, WO2008005964, WO2008043701, WO2008044777, WO2008047821, US2008096877, WO2008050117, WO2008050101, WO2008059625, US2008146625, WO2008078674, WO2008079787, WO2008084043, WO2008084044, WO2008084872, WO2008089892, WO2008091770, WO2008075073, WO2008084043, WO2008084044, WO2008084872, WO2008084873, WO2008089892, WO2008091770, JP2008189659, WO2008104994, WO2008111473, WO2008116107, WO2008118718, WO2008120754.

In one embodiment, the compound of the formula I is administered in combination with an inhibitor of gluconeogenesis, as described, for example, in FR-225654, WO2008053446.

In one embodiment, the compound of the formula I is administered in combination with inhibitors of fructose 1,6-bisphosphatase (FBPase), for example MB-07729, CS-917 (MB-06322) or MB-07803, or those as described in WO2006023515, WO2006104030, WO2007014619, WO2007137962, WO2008019309, WO2008037628.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidyl peptidase-IV (DPP-IV), for example vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200 (melogliptin), GW-825964X, KRP-104, DP-893, ABT-341, ABT-279 or another salt thereof, S-40010, S-40755, PF-00734200, BI-1356, PHX-1149, alogliptin benzoate, linagliptin, melogliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006101752, WO2006065826, WO2006078676, WO2006073167, WO2006068163, WO2006085685, WO2006090915, WO2006104356, WO2006127530, WO2006111261, US2006890898, US2006803357, US2006303661, WO2007015767 (LY-2463665), WO2007024993, WO2007029086, WO2007063928, WO2007070434, WO2007071738, WO2007071576, WO2007077508, WO2007087231, WO2007097931, WO2007099385, WO2007100374, WO2007112347, WO2007112669, WO2007113226, WO2007113634, WO2007115821, WO2007116092, US2007259900, EP1852108, US2007270492, WO2007126745, WO2007136603, WO2007142253, WO2007148185, WO2008017670, US2008051452, WO2008027273, WO2008028662, WO2008029217, JP2008031064, JP2008063256, WO2008033851, WO2008040974, WO2008040995, WO2008060488, WO2008064107, WO2008066070, WO2008077597, JP2008156318, WO2008087560, WO2008089636, WO2008093960, WO2008096841, WO2008101953, WO2008118848, WO2008119005, WO2008119208, WO2008120813, WO2008121506.

In one embodiment, the compound of the formula I is administered in combination with Janumet™, a solid combination of sitagliptin phosphate with metformin hydrochloride.

In one embodiment, the compound of the formula I is administered in combination with Eucreas®, a solid combination of vildagliptin with metformin hydrochloride.

In a further embodiment, the compound of the formula I is administered in combination with a solid combination of alogliptin benzoate with pioglitazone.

In one embodiment, the compound of the formula I is administered in combination with a solid combination of a salt of sitagliptin with metformin hydrochloride.

In one embodiment, the compound of the formula I is administered in combination with a combination of a DPP-IV inhibitor with omega-3 fatty acids or omega-3 fatty acid esters, as described, for example, in WO2007128801.

In one embodiment, the compound of the formula I is administered in combination with a solid combination of a salt of sitagliptin with metformin hydrochloride.

In one embodiment, the compound of the formula I is administered in combination with a substance which enhances insulin secretion, for example KCP-265

(WO2003097064), or those as described in WO2007026761, WO2008045484, US2008194617.

In one embodiment, the compound of the formula I is administered in combination with agonists of the glucose-dependent insulinotropic receptor (GDIR), for example APD-668.

In one embodiment of the invention, the compound of the formula I is administered in combination with an ATP citrate lyase inhibitor, for example SB-204990.

In one embodiment, the compound of the formula I is administered in combination with modulators of the sodium-dependent glucose transporter 1 or 2 (SGLT1, SGLT2), for example KGA-2727, T-1095, SGL-0010, AVE 2268, SAR 7226, SGL-5083, SGL-5085, SGL-5094, ISIS-388626, sergliflozin or dapagliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170, WO2007093610, WO2007126117, WO2007128480, WO2007129668, US2007275907, WO2007136116, WO2007143316, WO2007147478, WO2008001864, WO2008002824, WO2008013277, WO2008013280, WO2008013321, WO2008013322, WO2008016132, WO2008020011, JP2008031161, WO2008034859, WO2008042688, WO2008044762, WO2008046497, WO2008049923, WO2008055870, WO2008055940, WO2008069327, WO2008070609, WO2008071288, WO2008072726, WO2008083200, WO2008090209, WO2008090210, WO2008101586, WO2008101939, WO2008116179, WO2008116195, US2008242596, or by A. L. Handlon in Expert Opin. Ther. Patents (2005) 15(11), 1531-1540.

In one embodiment, the compound of the formula I is administered in combination with inhibitors of 11-beta-hydroxysteroid dehydrogenase 1 (11β-HSD1), for example BVT-2733, JNJ-25918646, INCB-13739, INCB-20817, DIO-92 ((−)-ketoconazole) or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005063247, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138508, WO2006138695, WO2006133926, WO2007003521, WO2007007688, US2007066584, WO2007029021, WO2007047625, WO2007051811, WO2007051810, WO2007057768, WO2007058346, WO2007061661, WO2007068330, WO2007070506, WO2007087150, WO2007092435, WO2007089683, WO2007101270, WO2007105753, WO2007107470, WO2007107550, WO2007111921, US2007207985, US2007208001, WO2007115935, WO2007118185, WO2007122411, WO2007124329, WO2007124337, WO2007124254, WO2007127688, WO2007127693, WO2007127704, WO2007127726, WO2007127763, WO2007127765, WO2007127901, US2007270424, JP2007291075, WO2007130898, WO2007135427, WO2007139992, WO2007144394, WO2007145834, WO2007145835, WO2007146761, WO2008000950, WO2008000951, WO2008003611, WO2008005910, WO2008006702, WO2008006703, WO2008011453, WO2008012532, WO2008024497, WO2008024892, WO2008032164, WO2008034032, WO2008043544, WO2008044656, WO2008046758, WO2008052638, WO2008053194, WO2008071169, WO2008074384, WO2008076336, WO2008076862, WO2008078725, WO2008087654, WO2008088540, WO2008099145, WO2008101885, WO2008101886, WO2008101907, WO2008101914, WO2008106128, WO2008110196, WO2008119017, WO2008120655, WO2008127924.

In one embodiment, the compound of the formula I is administered in combination with inhibitors of protein tyrosine phosphatase 1B (PTP-1B), as described, for example, in WO200119830-31, WO200117516, WO2004506446, WO2005012295, WO2005116003, WO2005116003, WO2006007959, DE 10 2004 060542.4, WO2007009911, WO2007028145, WO2007067612-615, WO2007081755, WO2007115058, US2008004325, WO2008033455, WO2008033931, WO2008033932, WO2008033934, WO2008089581.

In one embodiment of the invention, the compound of the formula I is administered in combination with an agonist of GPR109A (HM74A receptor agonists; NAR agonists (nicotinic acid receptor agonists)), for example nicotinic acid or extended release niacin in conjunction with MK-0524A (laropiprant) or MK-0524, or those compounds as described in WO2004041274, WO2006045565, WO2006045564, WO2006069242, WO2006085108, WO2006085112, WO2006085113, WO2006124490, WO2006113150, WO2007017261, WO2007017262, WO2007017265, WO2007015744, WO2007027532, WO2007092364, WO2007120575, WO2007134986, WO2007150025, WO2007150026, WO2008016968, WO2008051403, WO2008086949, WO2008091338, WO2008097535, WO2008099448, US2008234277, WO2008127591.

In another embodiment of the invention, the compound of the formula I is administered in combination with a solid combination of niacin with simvastatin.

In another embodiment of the invention, the compound of the formula I is administered in combination with nicotinic acid or extended release niacin in conjunction with MK-0524A (laropiprant).

In a further embodiment of the invention, the compound of the formula I is administered in combination with nicotinic acid or extended release niacin in conjunction with MK-0524A (laropiprant) and with simvastatin.

In one embodiment of the invention, the compound of the formula I is administered in combination with nicotinic acid or another nicotinic acid receptor agonist and a prostaglandin DP receptor antagonist, for example those as described in WO2008039882.

In another embodiment of the invention, the compound of the formula I is administered in combination with an agonist of GPR116, as described, for example, in WO2006067531, WO2006067532.

In one embodiment, the compound of the formula I is administered in combination with modulators of GPR40, as described, for example, in WO2007013689, WO2007033002, WO2007106469, US2007265332, WO2007123225, WO2007131619, WO2007131620, WO2007131621, US2007265332, WO2007131622, WO2007136572, WO2008001931, WO2008030520, WO2008030618, WO2008054674, WO2008054675, WO2008066097, US2008176912.

In one embodiment, the compound of the formula I is administered in combination with modulators of GPR119 (G-protein-coupled glucose-dependent insulinotropic receptor), for example PSN-119-1, PSN-821, PSN-119-2, MBX-2982, or those as described, for example, in WO2004065380, WO2005061489 (PSN-632408), WO2006083491, WO2007003960-62 and WO2007003964, WO2007035355, WO2007116229, WO2007116230, WO2008005569, WO2008005576, WO2008008887, WO2008008895, WO2008025798, WO2008025799, WO2008025800, WO2008070692, WO2008076243, WO200807692, WO2008081204, WO2008081205, WO2008081206, WO2008081207, WO2008081208, WO2008083238, WO2008085316, WO2008109702.

In a further embodiment, the compound of the formula I is administered in combination with modulators of GPR120, as described, for example, in EP1688138, WO2008066131, WO2008066131, WO2008103500, WO2008103501.

In one embodiment, the compound of the formula I is administered in combination with inhibitors of hormone-sensitive lipase (HSL) and/or phospholipases, as described, for example, in WO2005073199, WO2006074957, WO2006087309, WO2006111321, WO2007042178, WO2007119837, WO2008122352, WO2008122357.

In one embodiment, the compound of the formula I is administered in combination with inhibitors of endothelial lipase, as described, for example, in WO2006111321, WO2006131233, WO2006131232, WO2006131231, WO2007042178, WO2007045392, WO2007045393, WO2007110216, WO2007110215, WO2008122357, WO2008122352.

In one embodiment, the compound of the formula I is administered in combination with a phospholipase A2 inhibitor, for example darapladib or A-002, or those as described in WO2008048866, WO20080488867.

In one embodiment, the compound of the formula I is administered in combination with myricitrin, a lipase inhibitor (WO2007119827).

In one embodiment, the compound of the formula I is administered in combination with an inhibitor of glycogen synthase kinase-3 beta (GSK-3 beta), as described, for example, in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117, WO2007073117, WO2007083978, WO2007120102, WO2007122634, WO2007125109, WO2007125110, US2007281949, WO2008002244, WO2008002245, WO2008016123, WO2008023239, WO2008044700, WO2008056266, WO2008057940, WO2008077138, EP1939191, EP1939192, WO2008078196, WO2008094992, WO2008112642, WO2008112651, WO2008113469, WO2008121063, WO2008121064.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of phosphoinositide kinase-3 (PI3K), for example those as described in WO2008027584, WO2008070150, WO2008125833, WO2008125835, WO2008125839.

In one embodiment, the compound of the formula I is administered in combination with an inhibitor of serum/glucocorticoid-regulated kinase (SGK), as described, for example, in WO2006072354, WO2007093264, WO2008009335, WO2008086854.

In one embodiment, the compound of the formula I is administered in combination with a modulator of the glucocorticoid receptor, as described, for example, in WO2008057855, WO2008057856, WO2008057857, WO2008057859, WO2008057862, WO2008059867, WO2008059866, WO2008059865, WO2008070507, WO2008124665, WO2008124745.

In one embodiment, the compound of the formula I is administered in combination with a modulator of the mineralocorticoid receptor (MR), for example drospirenone, or those as described in WO2008104306, WO2008119918.

In one embodiment, the compound of the formula I is administered in combination with an inhibitor of protein kinase C beta (PKC beta), for example ruboxistaurin, or those as described in WO2008096260, WO2008125945.

In one embodiment, the compound of the formula I is administered in combination with an inhibitor of protein kinase D, for example doxazosin (WO2008088006).

In a further embodiment, the compound of the formula I is administered in combination with an activator of the AMP-activated protein kinase (AMPK), as described, for example, in WO2007062568, WO2008006432, WO2008016278, WO2008016730, WO2008083124.

In one embodiment, the compound of the formula I is administered in combination with an inhibitor of ceramide kinase, as described, for example, in WO2007112914, WO2007149865.

In a further embodiment, the compound of the formula I is administered in combination with an inhibitor of MAPK-interacting kinase 1 or 2 (MNK1 or 2), as described, for example, in WO2007104053, WO2007115822, WO2008008547, WO2008075741.

In one embodiment, the compound of the formula I is administered in combination with inhibitors of "I-kappaB kinase" (IKK inhibitors), as described, for example, in WO2001000610, WO2001030774, WO2004022057, WO2004022553, WO2005097129, WO2005113544, US2007244140, WO2008099072, WO2008099073, WO2008099073, WO2008099074, WO2008099075.

In another embodiment, the compound of the formula I is administered in combination with inhibitors of NF-kappaB (NFKB) activation, for example salsalate.

In a further embodiment, the compound of the formula I is administered in combination with inhibitors of ASK-1 (apoptosis signal-regulating kinase 1), as described, for example, in WO2008016131.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, pitavastatin, L-659699, BMS-644950, or those as described in US2007249583, WO2008083551.

In a further embodiment of the invention, the compound of the formula I is administered in combination with a farnesoid X receptor (FXR) modulator, for example WAY-362450 or those as described in WO2003099821, WO2005056554, WO2007052843, WO2007070796, WO2007092751, JP2007230909, WO2007095174, WO2007140174, WO2007140183, WO2008000643, WO2008002573, WO2008025539, WO2008025540, JP2008214222.

In another embodiment of the invention, the compound of the formula I is administered in combination with a ligand of the liver X receptor (LXR), as described, for example, in WO2007092965, WO2008041003, WO2008049047, WO2008065754, WO2008073825, US2008242677.

In one embodiment of the invention, the compound of the formula I is administered in combination with a fibrate, for example fenofibrate, clofibrate, bezafibrate, or those as described in WO2008093655.

In one embodiment of the invention, the compound of the formula I is administered in combination with fibrates, for example the choline salt of fenofibrate (SLV-348).

In one embodiment of the invention, the compound of the formula I is administered in combination with fibrates, for example the choline salt of fenofibrate and an HMG-CoA reductase inhibitor, for example rosuvastatin.

In a further embodiment of the invention, the compound of the formula I is administered in combination with bezafibrate and diflunisal.

In a further embodiment of the invention, the compound of the formula I is administered in combination with a solid combination of fenofibrate or a salt thereof with simvastatin, rosuvastatin, fluvastatin, lovastatin, cerivastatin, pravastatin, pitavastatin or atorvastatin.

In a further embodiment of the invention, the compound of the formula I is administered in combination with Synordia (R), a solid combination of fenofibrate with metformin.

In one embodiment of the invention, the compound of the formula I is administered in combination with a cholesterol absorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG), or as described in WO2002050060, WO2002050068, WO2004000803, WO2004000804, WO2004000805, WO2004087655, WO2004097655, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163, WO2007059871, US2007232688, WO2007126358, WO2008033431, WO2008033465, WO2008052658, WO2008057336, WO2008085300.

In one embodiment of the invention, the compound of the formula I is administered in combination with an NPC1L1 antagonist, for example those as described in WO2008033464, WO2008033465.

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with atorvastatin.

In one embodiment of the invention, the compound of the formula I is administered in combination with a solid combination of ezetimibe with fenofibrate.

In one embodiment of the invention, the further active ingredient is a diphenylazetidinone derivative, as described, for example, in U.S. Pat. No. 6,992,067 or U.S. Pat. No. 7,205,290.

In a further embodiment of the invention, the further active ingredient is a diphenylazetidinone derivative, as described, for example, in U.S. Pat. No. 6,992,067 or U.S. Pat. No. 7,205,290, combined with a statin, for example simvastatin, fluvastatin, pravastatin, lovastatin, cerivastatin, atorvastatin, pitavastatin or rosuvastatin.

In one embodiment of the invention, the compound of the formula I is administered in combination with a solid combination of lapaquistat, a squalene synthase inhibitor, with atorvastatin.

In one embodiment of the invention, the compound of the formula I is administered in combination with a CETP inhibitor, for example torcetrapib, anacetrapib or JTT-705 (dalcetrapib), or those as described in WO2006002342, WO2006010422, WO2006012093, WO2006073973, WO2006072362, WO2007088996, WO2007088999, US2007185058, US2007185113, US2007185154, US2007185182, WO2006097169, WO2007041494, WO2007090752, WO2007107243, WO2007120621, US2007265252, US2007265304, WO2007128568, WO2007132906, WO2008006257, WO2008009435, WO2008018529, WO2008058961, WO2008058967, WO2008059513, WO2008070496, WO2008115442, WO2008111604.

In one embodiment of the invention, the compound of the formula I is administered in combination with bile acid absorption inhibitors (inhibitors of the intestinal bile acid transporter (IBAT)) (see, for example, U.S. Pat. No. 6,245,744, U.S. Pat. No. 6,221,897 or WO00/61568), for example HMR 1741, or those as described in DE 10 2005 033099.1 and DE 10 2005 033100.9, DE 10 2006 053635, DE 10 2006 053637, WO2007009655-56, WO2008058628, WO2008058629, WO2008058630, WO2008058631.

In one embodiment, the compound of the formula I is administered in combination with agonists of GPBAR1(G-protein-coupled bile acid receptor-1; TGR5), as described, for example, in US20060199795, WO2007110237, WO2007127505, WO2008009407, WO2008067219, WO2008067222, FR2908310, WO2008091540, WO2008097976.

In one embodiment, the compound of the formula I is administered in combination with inhibitors of the TRPM5 channel (TRP cation channel M5), as described, for example, in WO2008097504.

In one embodiment of the invention, the compound of the formula I is administered in combination with a polymeric bile acid adsorber, for example cholestyramine, colesevelam hydrochloride.

In one embodiment of the invention, the compound of the formula I is administered in combination with colesevelam hydrochloride and metformin or a sulfonylurea or insulin.

In one embodiment of the invention, the compound of the formula I is administered in combination with a chewing gum comprising phytosterols (Reductol™).

In one embodiment of the invention, the compound of the formula I is administered in combination with an inhibitor of the microsomal triglyceride transfer protein (MTP inhibitor), for example implitapide, BMS-201038, R-103757, AS-1552133, SLx-4090, AEGR-733, or those as described in WO2005085226, WO2005121091, WO2006010423, WO2006113910, WO2007143164, WO2008049806, WO2008049808, WO2008090198, WO2008100423.

In a further embodiment of the invention, the compound of the formula I is administered in combination with a combination of a cholesterol absorption inhibitor, for example ezetimibe, and an inhibitor of the triglyceride transfer protein (MTP inhibitor), for example implitapide, as described in WO2008030382 or in WO2008079398.

In one embodiment of the invention, the compound of the formula I is administered in combination with an active antihypertriglyceridemic ingredient, for example those as described in WO2008032980.

In another embodiment of the invention, the compound of the formula I is administered in combination with an antagonist of the somatostatin 5 receptor (SST5 receptor), for example those as described in WO2006094682.

In one embodiment of the invention, the compound of the formula I is administered in combination with an ACAT inhibitor, for example avasimibe, SMP-797 or KY-382, or those as described in WO2008087029, WO2008087030, WO2008095189.

In a further embodiment of the invention, the compound of the formula I is administered in combination with an inhibitor of liver carnitine palmitoyltransferase 1 (L-CPT1), as described, for example, in WO2007063012, WO2007096251 (ST-3473), WO2008015081, US2008103182, WO2008074692.

In a further embodiment of the invention, the compound of the formula I is administered in combination with a modulator of serine palmitoyltransferase (SPT), as described, for example, in WO2008031032, WO2008046071, WO2008083280, WO2008084300.

In one embodiment of the invention, the compound of the formula I is administered in combination with a squalene synthetase inhibitor, for example BMS-188494, TAK-475 (lapaquistat acetate), or as described in WO2005077907, JP2007022943, WO2008003424.

In one embodiment of the invention, the compound of the formula I is administered in combination with ISIS-301012 (mipomersen), an antisense oligonucleotide which is capable of regulating the apolipoprotein B gene.

In one embodiment of the invention, the compound of the formula I is administered in combination with a stimulator of the ApoA-1 gene, as described, for example, in WO2008092231.

In one embodiment of the invention, the compound of the formula I is administered in combination with an LDL receptor inducer (see U.S. Pat. No. 6,342,512), for example HMR1171, HMR1586, or those as described in WO2005097738, WO2008020607.

In another embodiment of the invention, the compound of the formula I is administered in combination with an HDL cholesterol-elevating agent, for example those as described in WO2008040651, WO2008099278.

In one embodiment of the invention, the compound of the formula I is administered in combination with an ABCA1 expression enhancer, as described, for example, in WO2006072393, WO2008062830.

In one embodiment of the invention, the compound of the formula I is administered in combination with a lipoprotein lipase modulator, for example ibrolipim (NO-1886).

In one embodiment of the invention, the compound of the formula I is administered in combination with a lipoprotein (a) antagonist, for example gemcabene (CI-1027).

In one embodiment of the invention, the compound of the formula I is administered in combination with a lipase inhibitor, for example orlistat or cetilistat (ATL-962).

In one embodiment of the invention, the compound of the formula I is administered in combination with an adenosine A1 receptor agonist (adenosine A1 R), as described, for example, in EP1258247, EP1375508, WO2008028590, WO2008077050.

In one embodiment of the invention, the compound of the formula I is administered in combination with an adenosine A2B receptor agonist (adenosine A2B R), for example ATL-801.

In another embodiment of the invention, the compound of the formula I is administered in combination with a modulator of adenosine A2A and/or adenosine A3 receptors, as described, for example, in WO2007111954, WO2007121918, WO2007121921, WO2007121923, WO2008070661.

In a further embodiment of the invention, the compound of the formula I is administered in combination with an agonist of the adenosine A1/A2B receptors, as described, for example, in WO2008064788, WO2008064789.

In one embodiment of the invention, the compound of the formula I is administered in combination with an adenosine A2B receptor antagonist (adenosine A2B R), as described in US2007270433, WO2008027585, WO2008080461.

In one embodiment, the compound of the formula I is administered in combination with inhibitors of acetyl-CoA carboxylase (ACC1 and/or ACC2), for example those as described in W0199946262, WO200372197, WO2003072197, WO2005044814, WO2005108370, JP2006131559, WO2007011809, WO2007011811, WO2007013691, WO2007095601-603, WO2007119833, WO2008065508, WO2008069500, WO2008070609, WO2008072850, WO2008079610, WO2008088688, WO2008088689, WO2008088692, US2008171761, WO2008090944, JP2008179621, US2008200461, WO2008102749, WO2008103382, WO2008121592.

In another embodiment, the compound of the formula I is administered in combination with modulators of microsomal acyl-CoA:glycerol-3-phosphate acyltransferase 3 (GPAT3, described in WO2007100789) or with modulators of microsomal acyl-CoA:glycerol-3-phosphate acyltransferase 4 (GPAT4, described in WO2007100833).

In a further embodiment, the compound of the formula I is administered in combination with modulators of xanthine oxidoreductase (XOR).

In another embodiment, the compound of the formula I is administered in combination with inhibitors of soluble epoxide hydrolase (sEH), as described, for example, in WO2008051873, WO2008051875, WO2008073623, WO2008094869, WO2008112022.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylannino)methyl]-cyclohexylmethylnaphthalene-1-sulfonamide hydrochloride (CGP 71683A) or velneperit;

NPY-5 receptor antagonists, such as L-152804 or the compound "NPY-5-BY" from Banyu, or as described, for example, in WO2006001318, WO2007103295, WO2007125952, WO2008026563, WO2008026564, WO2008052769, WO2008092887, WO2008092888, WO2008092891;

NPY-4 receptor antagonists, as described, for example, in WO2007038942;

NPY-2 receptor antagonists, as described, for example, in WO2007038943;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424, WO2006095166, WO2008003947;

derivatives of the peptide obestatin, as described by WO2006096847;

CB1R (cannabinoid receptor 1) antagonists, for example rimonabant, surinabant (SR147778), SLV-319 (ibipinabant), AVE-1625, taranabant (MK-0364) or salts thereof, otenabant (CP-945,598), rosonabant, V-24343 or those compounds as described in, for example, EP 0656354, WO 00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006018662, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007018460, WO2007016460, WO2007020502, WO2007026215, WO2007028849, WO2007031720, WO2007031721, WO2007036945, WO2007038045, WO2007039740, US20070015810, WO2007046548, WO2007047737, WO2007057687, WO2007062193, WO2007064272, WO2007079681, WO2007084319, WO2007084450, WO2007086080, EP1816125, US2007213302, WO2007095513, WO2007096764, US2007254863, WO2007119201, WO2007120454, WO2007121687, WO2007123949, US2007259934, WO2007131219, WO2007133820, WO2007136571, WO2007136607, WO2007136571, US7297710, WO2007138050, WO2007139464, WO2007140385, WO2007140439, WO2007146761, WO2007148061, WO2007148062, US2007293509, WO2008004698, WO2008017381, US2008021031, WO2008024284, WO2008031734, WO2008032164, WO2008034032, WO2008035356, WO2008036021, WO2008036022, WO2008039023, W02998043544, WO2008044111, WO2008048648, EP1921072-A1, WO2008053341, WO2008056377, WO2008059207, WO2008059335, WO2008062424, WO2008068423, WO2008068424, WO2008070305, WO2008070306, WO2008074816, WO2008074982, WO2008075012, WO2008075013, WO2008075019, WO2008075118, WO2008076754, WO2008081009, WO2008084057, EP1944295, US2008090809, US2008090810, WO2008092816, WO2008094473, WO2008094476, WO2008099076, WO2008099139, WO2008101995, US2008207704, WO2008107179, WO2008109027, WO2008112674, WO2008115705, WO2008118414, WO2008119999, WO200812000, WO2008121257, WO2008127585;

cannabinoid receptor 1/cannabinoid receptor 2 (CB1/CB2) modulating compounds, for example delta-9-tetrahydrocannabivarin, or those as described, for example, in WO2007001939, WO2007044215, WO2007047737, WO2007095513, WO2007096764, WO2007112399, WO2007112402, WO2008122618;

modulators of FAAH (fatty acid amide hydrolase), as described, for example, in WO2007140005, WO2008019357, WO2008021625, WO2008023720, WO2008030532;

inhibitors of fatty acid synthase (FAS), as described, for example, in WO2008057585, WO2008059214, WO2008075064, WO2008075070, WO2008075077;

inhibitors of LCE (long chain fatty acid elongase), as described, for example, in WO2008120653;

vanilloid-1 receptor modulators (modulators of TRPV1), as described, for example, in WO2007091948, WO2007129188, WO2007133637, WO2008007780, WO2008010061, WO2008007211, WO2008010061, WO2008015335, WO2008018827, WO2008024433, WO2008024438, WO2008032204, WO2008050199, WO2008059339, WO2008059370, WO2008066664, WO2008075150, WO2008090382, WO2008090434, WO2008093024, WO2008107543, WO2008107544, WO2008110863;

modulators, antagonists or inverse agonists of the opioid receptors, for example GSK-982 or those as described, for example, in WO2007047397, WO2008021849, WO2008021851, WO2008032156, WO2008059335;

modulators of the "orphan opioid (ORL-1) receptor", as described, for example, in US2008249122, WO2008089201;

agonists of the prostaglandin receptor, for example bimatoprost or those compounds as described in WO2007111806;

MC4 receptor agonists (melanocortin-4 receptor agonists, MC4R agonists, for example N-[2-(3a-benzyl-2-methyl-3-oxo-2,3,3a,4,6,7-hexahydropyrazolo[4,3-c]-pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, MK-0493, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052, JP2007131570, EP-1842846, WO2007096186, WO2007096763, WO2007141343, WO2008007930, WO2008017852, WO2008039418, WO2008087186, WO2008087187, WO2008087189, WO2008087186-WO2008087190, WO2008090357;

orexin receptor 1 antagonists (OX1R antagonists), orexin receptor 2 antagonists (OX2R antagonists) or mixed OX1R/OX2R antagonists (e.g. 1-(2-methylbenzoxazol-6-yl)-3-[1,5]naphthyridin-4-ylurea hydrochloride (SB-334867-A), or those as described, for example, in WO200196302, WO200185693, WO2004085403, WO2005075458, WO2006067224, WO2007088276, WO2007116374, WO2007122591, WO2007126934, WO2007126935, WO2008008517, WO2008008518, WO2008008551, WO2008020405, WO2008026149, WO2008038251, US2008132490, WO2008065626, WO2008078291, WO2008087611, WO2008081399, WO2008108991, WO2008107335, US2008249125);

histamine H3 receptor antagonists/inverse agonists (e.g. 3-cyclohexyl-1-(4,4-dimethyl-1,4,6,7-tetrahydroimidazo[4,5-c]pyridin-5-yl)propan-1-one oxalic acid salt (WO 00/63208), or those as described in WO200064884, WO2005082893, US2005171181 (e.g. PF-00389027), WO2006107661, WO2007003804, WO2007016496, WO2007020213, WO2007049798, WO2007055418, WO2007057329, WO2007065820, WO2007068620, WO2007068641, WO2007075629, WO2007080140, WO2007082840, WO2007088450, WO2007088462, WO2007094962, WO2007099423, WO2007100990, WO2007105053, WO2007106349, WO2007110364, WO2007115938, WO2007131907, WO2007133561, US2007270440, WO2007135111, WO2007137955, US2007281923, WO2007137968, WO2007138431, WO2007146122, WO2008005338, WO2008012010, WO2008015125, WO2008045371, EP1757594, WO2008068173, WO2008068174, US20080171753, WO2008072703, WO2008072724, US2008188484, US2008188486, US2008188487, WO2008109333, WO2008109336);

histamine H1/histamine H3 modulators, for example betahistine or its dihydrochloride;

modulators of the histamine H3 transporter or of the histamine H3/serotonin transporter, as described, for example, in WO2008002816, WO2008002817, WO2008002818, WO2008002820;

histamine H4 modulators, as described, for example, in WO2007117399;

CRF antagonists (e.g. [2-methyl-9-(2,4,6-trimethylphenyl)-9H-1,3,9-triazafluoren-4-yl]dipropylamine (WO 00/66585) or those CRF1 antagonists as described in WO2007105113, WO2007133756, WO2008036541, WO2008036579, WO2008083070);

ORE BP antagonists (e.g. urocortin);

urocortin agonists;

modulators of the beta-3 adrenoceptor, for example 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as described in JP2006111553, WO2002038543, WO2002038544, WO2007048840-843, WO2008015558, EP1947103;

MSH (melanocyte-stimulating hormone) agonists;

MCH (melanine-concentrating hormone) receptor antagonists (for example NBI-845, A-761, A-665798, A-798, ATC-0175, T-226296, T-71 (AMG-071, AMG-076), GW-856464, NGD-4715, ATC-0453, ATC-0759, GW-803430, or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649, WO2007092416; WO2007093363-366, WO2007114902, WO2007114916, WO2007141200, WO2007142217, US2007299062, WO2007146758, WO2007146759, WO2008001160, WO2008016811, WO2008020799, WO2008022979, WO2008038692, WO2008041090, WO2008044632, WO2008047544, WO2008061109, WO2008065021, WO2008068265, WO2008071646, WO2008076562, JP2008088120, WO2008086404, WO2008086409);

CCK-A (CCK-1) agonists/modulators (for example {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180), or those as described in WO2005116034, WO2007120655, WO2007120688, WO2007120718, WO2008091631;

serotonin reuptake inhibitors (e.g. dexfenfluramines), or those as described in WO2007148341, WO2008034142, WO2008081477, WO2008120761;

mixed serotonin/dopamine reuptake inhibitors (e.g. bupropion), or those as described in WO2008063673, or solid combinations of bupropion with naltrexone or bupropion with zonisamide;

mixed reuptake inhibitors, for example DOV-21947;

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

mixed dopamine/norepinephrine/acetylcholine reuptake inhibitors (e.g. tesofensine), or those as described, for example, in WO2006085118;

dopamine antagonists, as described, for example, in WO2008079838, WO2008079839, WO2008079847, WO2008079848;

norepinephrine reuptake inhibitors, as described, for example, in US2008076724;

5-HT2A receptor antagonists, as described, for example, in WO2007138343;

5-HT2C receptor agonists (for example lorcaserine hydrochloride (APD-356) or BVT-933, or those as described in WO200077010, WO200077001-02, WO2005019180, WO2003064423, WO200242304, WO2005035533, WO2005082859, WO2006004937, US2006025601, WO2006028961, WO2006077025, WO2006103511, WO2007028132, WO2007084622, US2007249709; WO2007132841, WO2007140213, WO2008007661, WO2008007664, WO2008009125, WO2008010073, WO2008108445);

5-HT6 receptor modulators, for example E-6837, BVT-74316 or PRX-07034, or those as described, for example, in WO2005058858, WO2007054257, WO2007107373, WO2007108569, WO2007108742-744, WO2008003703, WO2008027073, WO2008034815, WO2008054288, EP1947085, WO2008084491, WO2008084492, WO2008092665, WO2008092666, WO2008101247, WO2008110598, WO2008116831, WO2008116833;

agonists of estrogen receptor gamma (ERRγ agonists), as described, for example, in WO2007131005, WO2008052709;

agonists of estrogen receptor alpha (ERRα/ERR1 agonists), as described, for example, in WO2008109727;

sigma-1 receptor antagonists, as described, for example, in WO2007098953, WO2007098961, WO2008015266, WO2008055932, WO2008055933;

muscarin 3 receptor (M3R) antagonists, as described, for example, in WO2007110782, WO2008041184;

bombesin receptor agonists (BRS-3 agonists), as described, for example, in WO2008051404, WO2008051405, WO2008051406, WO2008073311;

galanin receptor antagonists;

growth hormone (e.g. human growth hormone or AOD-9604);

growth hormone-releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734, WO2007127457, WO2008008286;

growth hormone secretagogue receptor modulators (ghrelin modulators), for example JMV-2959, JMV-3002, JMV-2810, JMV-2951, or those as described in WO2006012577 (e.g. YIL-781 or YIL-870), WO2007079239, WO2008092681;

TRH agonists (see, for example, EP 0 462 884);

decoupling protein 2 or 3 modulators;

chemical decouplers (e.g. WO2008059023, WO2008059024, WO2008059025, WO2008059026);

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

DA agonists (bromocriptine, Doprexin);

lipase/amylase inhibitors (e.g. WO 00/40569, WO2008107184); inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538, WO2007060140, JP2007131584, WO2007071966, WO2007126957, WO2007137103, WO2007137107, WO2007138304, WO2007138311, WO2007141502, WO2007141517, WO2007141538, WO2007141545, WO2007144571, WO2008011130, WO2008011131, WO2008039007, WO2008048991, WO2008067257, WO2008099221;

inhibitors of monoacylglycerol acyltransferase (2-acylglycerol O-acyltransferase; MGAT), as described, for example, in WO2008038768;

inhibitors of fatty acid synthase (FAS), for example C75, or those as described in WO2004005277, WO2008006113;

inhibitors of stearoyl-CoA delta9 desaturase (SCD1), as described, for example, in WO2007009236, WO2007044085, WO2007046867, WO2007046868, WO20070501124, WO2007056846, WO2007071023, WO2007130075, WO2007134457, WO2007136746, WO2007143597, WO2007143823, WO2007143824, WO2008003753, WO2008017161, WO2008024390, WO2008029266, WO2008036715, WO2008043087, WO2008044767, WO2008046226, WO2008056687, WO2008062276, WO2008064474, WO2008074824, WO2008074832, WO2008074833, WO2008074834, WO2008074835, WO2008089580, WO2008096746, WO2008104524, WO2008116898, US2008249100, WO2008120744, WO2008120759, WO2008123469, WO2008127349;

inhibitors of fatty acid desaturase 1 (delta5 desaturase), as described, for example, in WO2008089310;

hypoglycemic/hypertriglyceridemic indoline compounds, as described in WO2008039087;

inhibitors of "adipocyte fatty acid-binding protein aP2", for example BMS-309403;

activators of adiponectin secretion, as described, for example, in WO2006082978, WO2008105533;

promoters of adiponectin production, as described, for example, in WO2007125946, WO2008038712;

modified adiponectins, as described, for example, in WO2008121009;

oxyntomodulin or analogs thereof;

oleoyl-estrone;

or agonists or partial agonists of the thyroid hormone receptor (thyroid hormone receptor agonists), for example: KB-2115 (eprotirome), QRX-431 (sobetirome) or DITPA, or those as described in WO20058279, WO200172692, WO200194293, WO2003084915, WO2004018421, WO2005092316, WO2007003419, WO2007009913, WO2007039125, WO2007110225, WO2007110226, WO2007128492, WO2007132475, WO2007134864, WO2008001959, WO2008106213;

or agonists of the thyroid hormone receptor beta (TR-beta), for example MB-07811 or MB-07344, or those as described in WO2008062469.

In one embodiment of the invention, the compound of the formula I is administered in combination with a combination of eprotirome with ezetimibe.

In one embodiment of the invention, the compound of the formula I is administered in combination with an inhibitor of site-1 protease (S1P), for example PF-429242.

In a further embodiment of the invention, the compound of the formula I is administered in combination with a modulator of the "trace amine associated receptor 1" (TAAR1), as described, for example, in US2008146523, WO2008092785.

In one embodiment of the invention, the compound of the formula I is administered in combination with an inhibitor of growth factor receptor bound protein 2 (GRB2), as described, for example, in WO2008067270.

In a further embodiment of the invention, the compound of the formula I is administered in combination with an RNAi (siRNA) therapeutic agent directed against PCSK9 (proprotein convertase subtilisin/kexin type 9).

In one embodiment, the compound of the formula I is administered in combination with Omacor® or Lovaza™ (omega-3 fatty acid ester; highly concentrated ethyl ester of eicosapentaenoic acid and of docosahexaenoic acid).

In one embodiment, the compound of the formula I is administered in combination with lycopene.

In one embodiment of the invention, the compound of the formula I is administered in combination with an antioxidant, for example OPC-14117, AGI-1067 (succinobucol), probucol, tocopherol, ascorbic acid, β-carotene or selenium.

In one embodiment of the invention, the compound of the formula I is administered in combination with a vitamin, for example vitamin B6 or vitamin B12.

In one embodiment, the compound of the formula I is administered in combination with more than one of the aforementioned compounds, for example in combination with a sulfonylurea and metformin, a sulfonylurea and acarbose, repaglinide and metformin (PrandiMet™), insulin and a sulfonylurea, insulin and metformin, insulin and troglitazone, insulin and lovastatin, etc.

In another embodiment, the compound of the formula I is administered in combination with an inhibitor of carboanhydrase type 2 (carbonic anhydrase type 2), for example those as described in WO2007065948.

In another embodiment, the compound of the formula I is administered in combination with topiramat or a derivative thereof, as described in WO2008027557.

In a further embodiment, the compound of the formula I is administered in combination with a solid combination of topiramat with phentermine (Qnexa™).

In a further embodiment, the compound of the formula I is administered in combination with an antisense compound, e.g. ISIS-377131, which inhibits the production of the glucocorticoid receptor.

In another embodiment, the compound of the formula I is administered in combination with an aldosterone synthase inhibitor and an antagonist of the glucocorticoid receptor, a cortisol synthesis inhibitor and/or an antagonist of the corticotropin releasing factor, as described, for example, in EP1886695, WO2008119744.

In one embodiment, the compound of the formula I is administered in combination with an agonist of the RUP3 receptor, as described, for example, in WO2007035355, WO2008005576.

In another embodiment, the compound of the formula I is administered in combination with an activator of the gene which codes for ataxia telangiectasia mutated (ATM) protein kinase, for example chloroquine.

In one embodiment, the compound of the formula I is administered in combination with a tau protein kinase 1 inhibitor (TPK1 inhibitor), as described, for example, in WO2007119463.

In one embodiment, the compound of the formula I is administered in combination with a "c-Jun N-terminal kinase" inhibitor (JNK inhibitor), as described, for example, in WO2007125405, WO2008028860, WO2008118626.

In one embodiment, the compound of the formula I is administered in combination with an endothelin A receptor antagonist, for example avosentan (SPP-301).

In one embodiment, the compound of the formula I is administered in combination with modulators of the glucocorticoid receptor (GR), for example KB-3305 or those compounds as described, for example, in WO2005090336, WO2006071609, WO2006135826, WO2007105766, WO2008120661.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the enzyme SIRT1 and/or SIRT3 (an NADtdependent protein deacetylase); this active ingredient may, for example, be resveratrol in suitable formulations, or those compounds as specified in WO2007019416 (e.g. SRT-1720), WO2008073451.

In one embodiment of the invention, the further active ingredient is DM-71 (N-acetyl-L-cysteine with bethanechol).

In one embodiment, the compound of the formula I is administered in combination with antihypercholesterolemic compounds, as described, for example, in WO2007107587, WO2007111994, WO2008106600, WO2008113796.

In a further embodiment, the compound of the formula I is administered in combination with inhibitors of SREBP (sterol regulatory element-binding protein), as described, for example, in WO2008097835.

In another embodiment, the compound of the formula I is administered in combination with a cyclic peptide agonist of the VPAC2 receptor, as described, for example, in WO2007101146, WO2007133828.

In a further embodiment, the compound of the formula I is administered in combination with an agonist of the endothelin receptor, as described, for example, in WO2007112069.

In a further embodiment, the compound of the formula I is administered in combination with AKP-020 (bis(ethyhaltolato)oxovanadium(IV)).

In another embodiment, the compound of the formula I is administered in combination with tissue-selective androgen receptor modulators (SARM), as described, for example, in WO2007099200, WO2007137874.

In a further embodiment, the compound of the formula I is administered in combination with an AGE (advanced glycation endproduct) inhibitor, as described, for example, in JP2008024673.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment of the invention, the further active ingredient is metreleptin (recombinant methionyl-leptin) combined with pramlintide.

In a further embodiment of the invention, the further active ingredient is the tetrapeptide ISF-402.

In one embodiment, the further active ingredient is dexamphetamine or amphetamine.

In one embodiment, the further active ingredient is fenfluramine or dexfenfluramine.

In another embodiment, the further active ingredient is sibutramine or those derivatives as described in WO2008034142.

In one embodiment, the further active ingredient is mazindol or phentermin.

In a further embodiment, the further active ingredient is geniposidic acid (WO2007100104) or derivatives thereof (JP2008106008).

In one embodiment, the further active ingredient is a nasal calcium channel blocker, for example diltiazem, or those as described in U.S. Pat. No. 7,138,107.

In one embodiment, the further active ingredient is an inhibitor of sodium-calcium ion exchange, for example those as described in WO2008028958, WO2008085711.

In a further embodiment, the further active ingredient is a blocker of calcium channels, for example of CaV3.2 or CaV2.2, as described in WO2008033431, WO2008033447, WO2008033356, WO2008033460, WO2008033464, WO2008033465, WO2008033468, WO2008073461.

In one embodiment, the further active ingredient is a modulator of a calcium channel, for example those as described in WO2008073934, WO2008073936.

In one embodiment, the further active ingredient is a blocker of the "T-type calcium channel", as described, for example, in WO2008033431, WO2008110008.

In one embodiment, the further active ingredient is an inhibitor of KCNQ potassium channel 2 or 3, for example those as described in US2008027049, US2008027090.

In one embodiment, the further active ingredient is an inhibitor of the potassium Kv1.3 ion channel, for example those as described in WO2008040057, WO2008040058, WO2008046065.

In another embodiment, the further active ingredient is a modulator of the MCP-1 receptor (monocyte chemoattractant protein-1 (MCP-1)), for example those as described in WO2008014360, WO2008014381.

In one embodiment, the further active ingredient is a modulator of somatostatin receptor 5 (SSTR5), for example those as described in WO2008019967, US2008064697, US2008249101, WO2008000692.

In one embodiment, the further active ingredient is a modulator of somatostatin receptor 2 (SSTR2), for example those as described in WO2008051272.

In one embodiment, the further active ingredient is an erythropoietin-mimetic peptide which acts as an erythropoietin (EPO) receptor agonist. Such molecules are described, for example, in WO2008042800.

In a further embodiment, the further active ingredient is an anorectic/a hypoglycemic compound, for example those as described in WO2008035305, WO2008035306, WO2008035686.

In one embodiment, the further active ingredient is an inductor of lipoic acid synthetase, for example those as described in WO2008036966, WO2008036967.

In one embodiment, the further active ingredient is a stimulator of endothelial nitric oxide synthase (eNOS), for example those as described in WO2008058641, WO2008074413.

In one embodiment, the further active ingredient is a modulator of carbohydrate and/or lipid metabolism, for example those as described in WO2008059023, WO2008059024, WO2008059025, WO2008059026.

In a further embodiment, the further active ingredient is an angiotensin II receptor antagonist, for example those as described in WO2008062905, WO2008067378, WO2008062905.

In one embodiment, the further active ingredient is an agonist of the sphingosine 1-phosphate receptor (S1P), for example those as described in WO2008064315, WO2008074820, WO2008074821.

In one embodiment, the further active ingredient is an agent which retards gastric emptying, for example 4-hydroxyisoleucine (WO2008044770).

In one embodiment, the further active ingredient is a muscle-relaxing substance, as described, for example, in WO2008090200.

In a further embodiment, the further active ingredient is an inhibitor of monoamine oxidase B (MAO-B), for example those as described in WO2008092091.

In another embodiment, the further active ingredient is an inhibitor of the binding of cholesterol and/or triglycerides to the SCP-2 protein (sterol carrier protein-2), for example those as described in US2008194658.

In another embodiment, the further active ingredient is lisofylline, which prevents autoimmune damage to insulin-producing cells.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Hochst, 65926 Frankfurt/Main)). Combination with Caromax® is possible in one preparation or by separate administration of compounds of the formula I and Caromax®. Caromax® can also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered by the scope of protection conferred by the present invention.

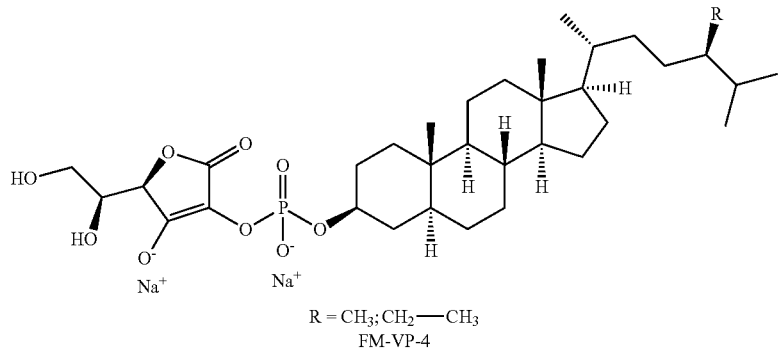

R = CH$_3$; CH$_2$—CH$_3$
FM-VP-4

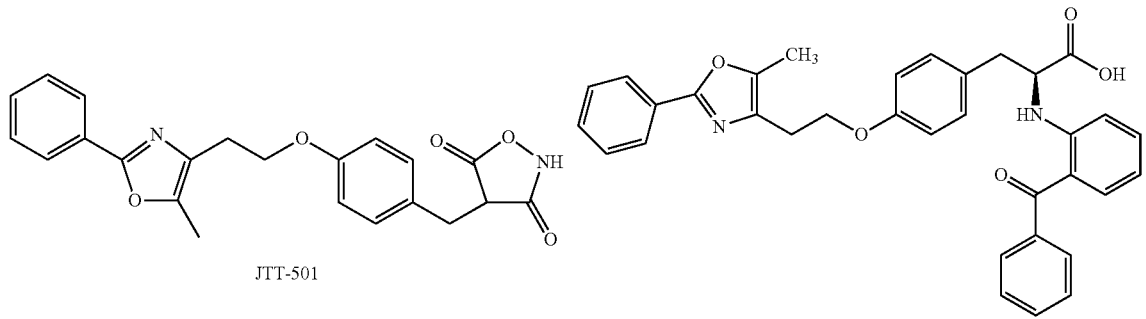

JTT-501

GI 262570

-continued
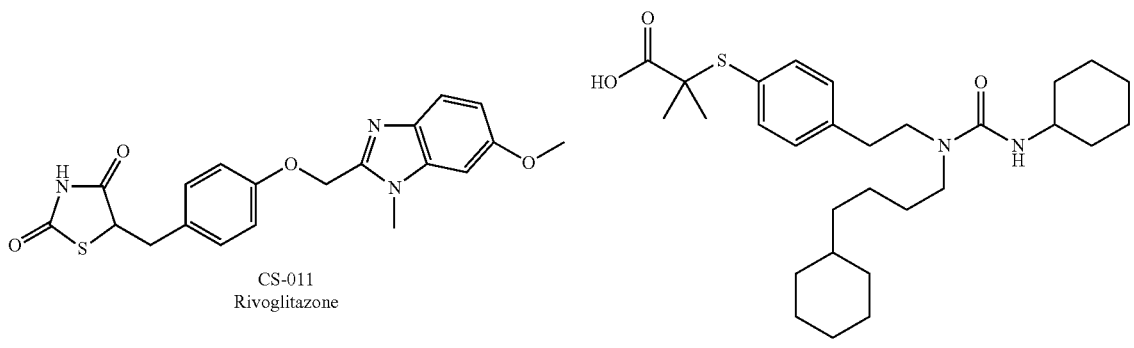
CS-011
Rivoglitazone
GW-9578
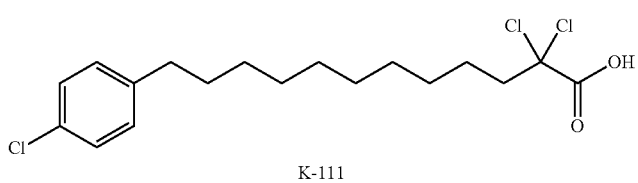
K-111
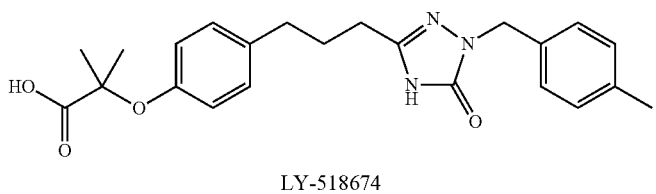
LY-518674
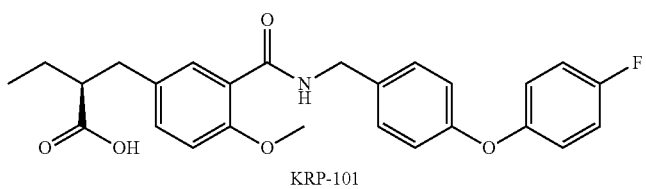
KRP-101
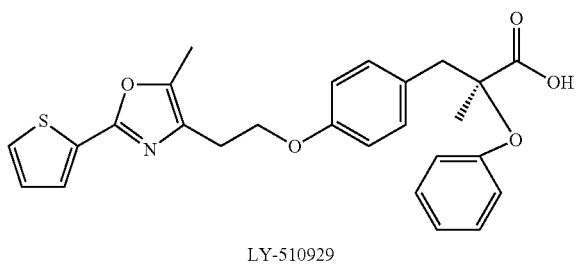
LY-510929
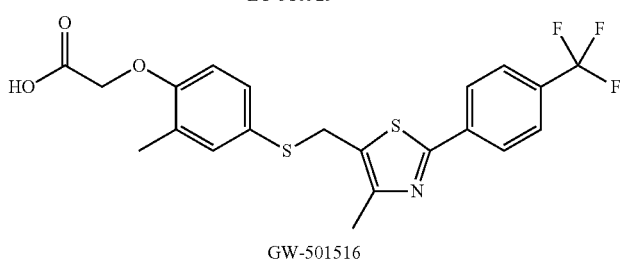
GW-501516

-continued
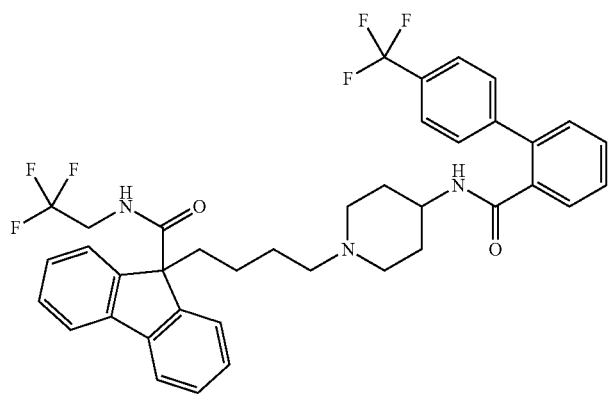
BMS-201038
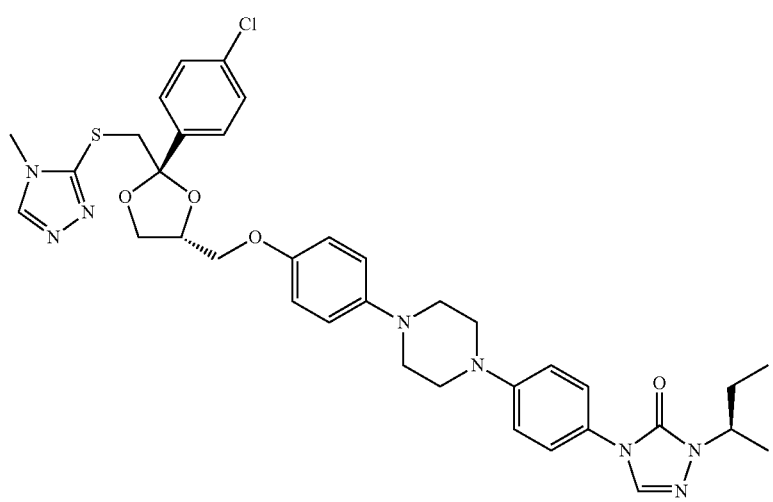
R-103757
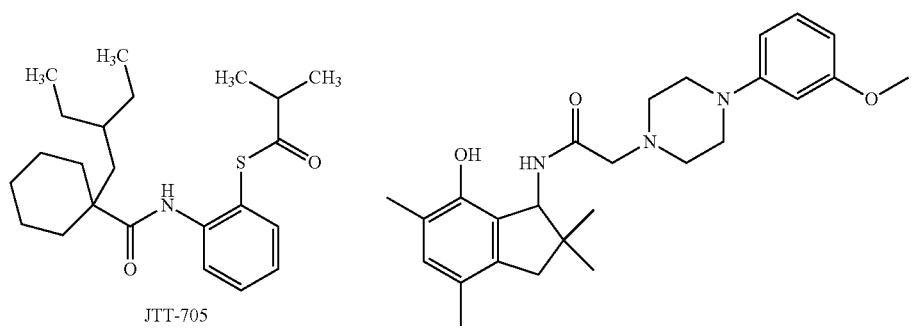
JTT-705
OPC-14117
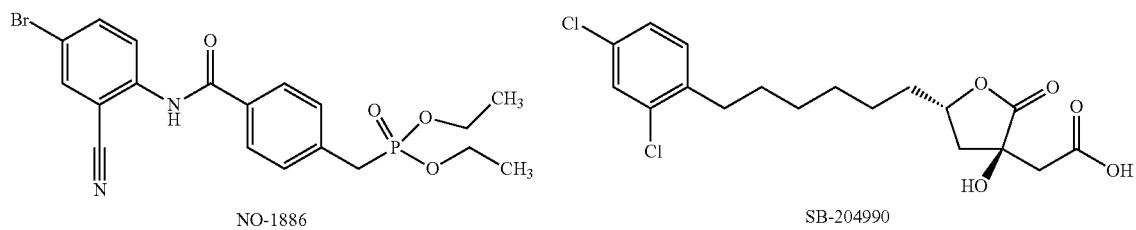
NO-1886
SB-204990

-continued
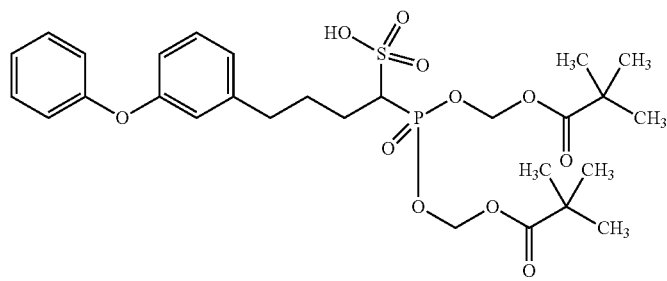
BMS-188494
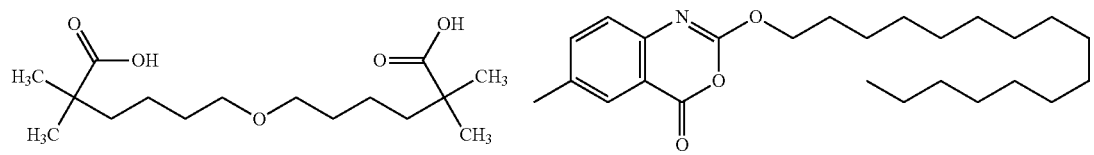
Cl-1027  ATL-962
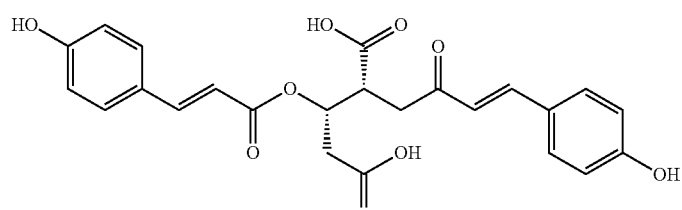
FR-258900
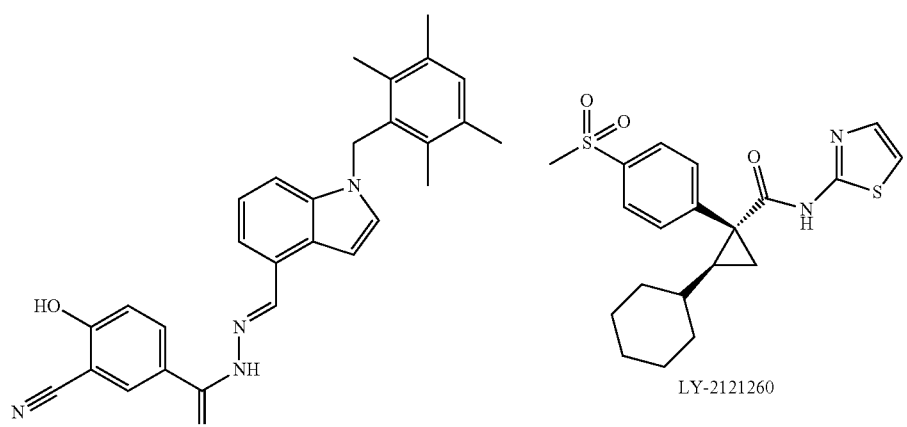
NNC-25-2504  LY-2121260
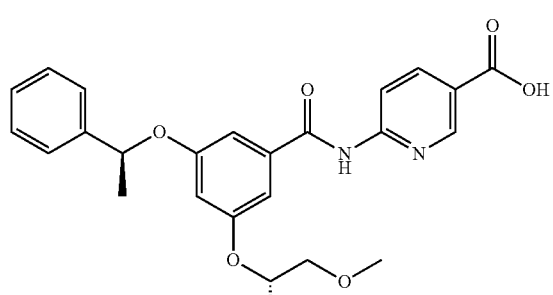
GKA-50
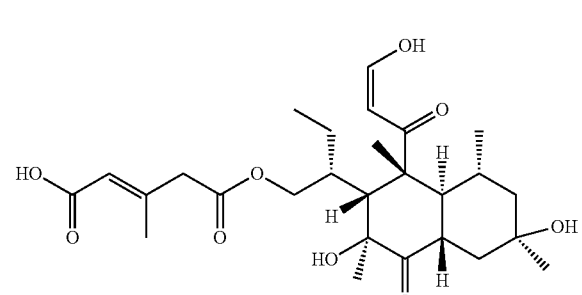
FR-225654

-continued
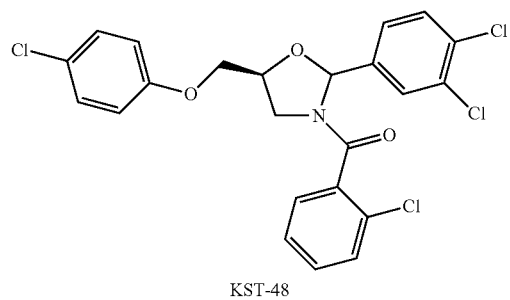
KST-48
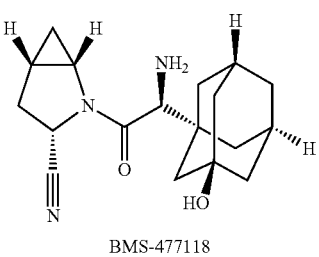
BMS-477118
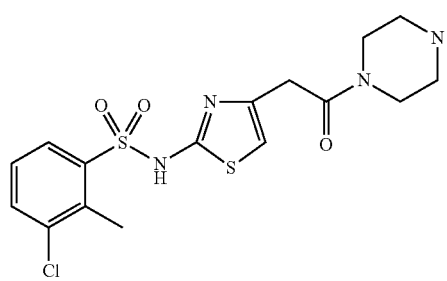
BVT-2733
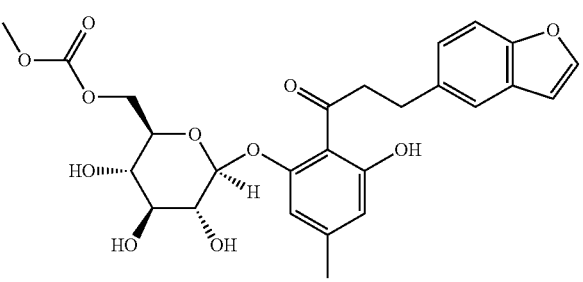
T-1095
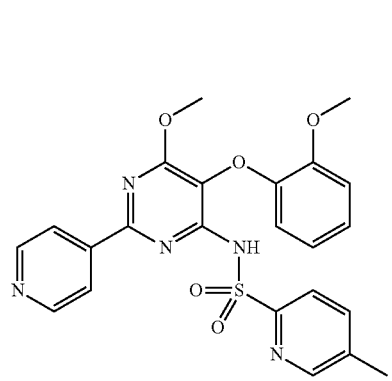
SPP-301
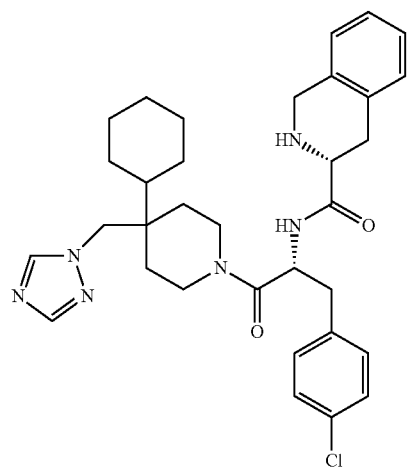
THIQ
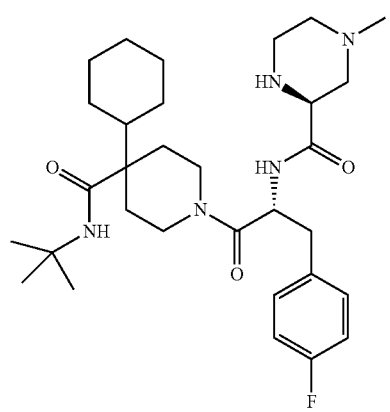
MB243
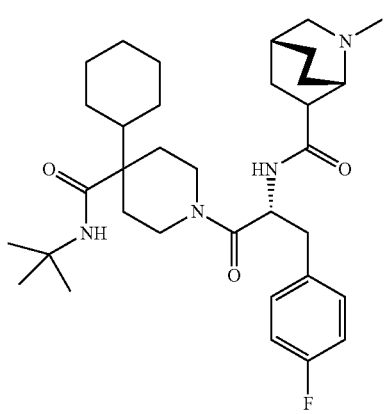
RY764

-continued
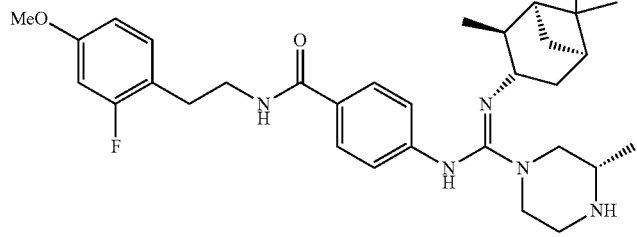
CHIR-785
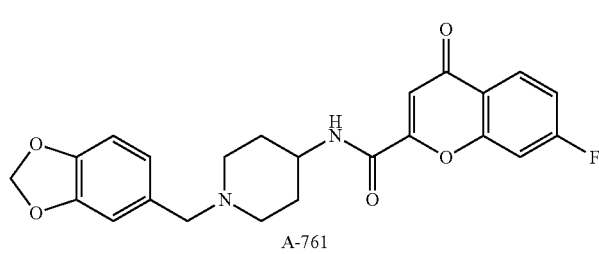
A-761
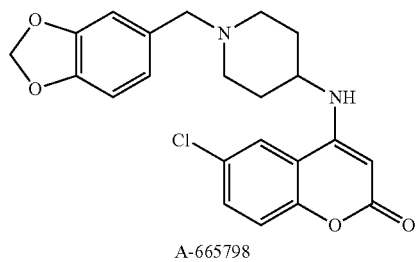
A-665798
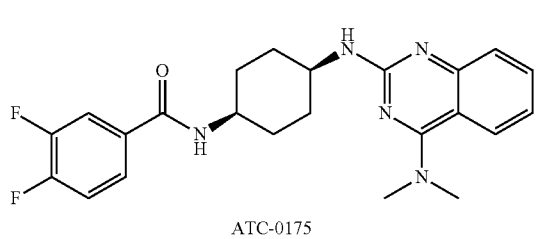
ATC-0175
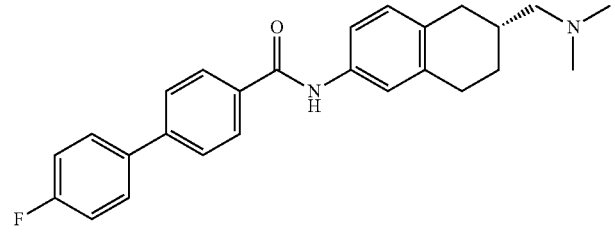
T-226296
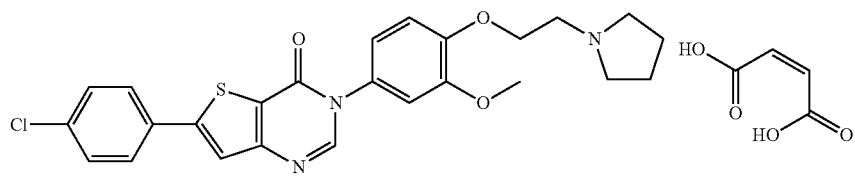
GW-803430
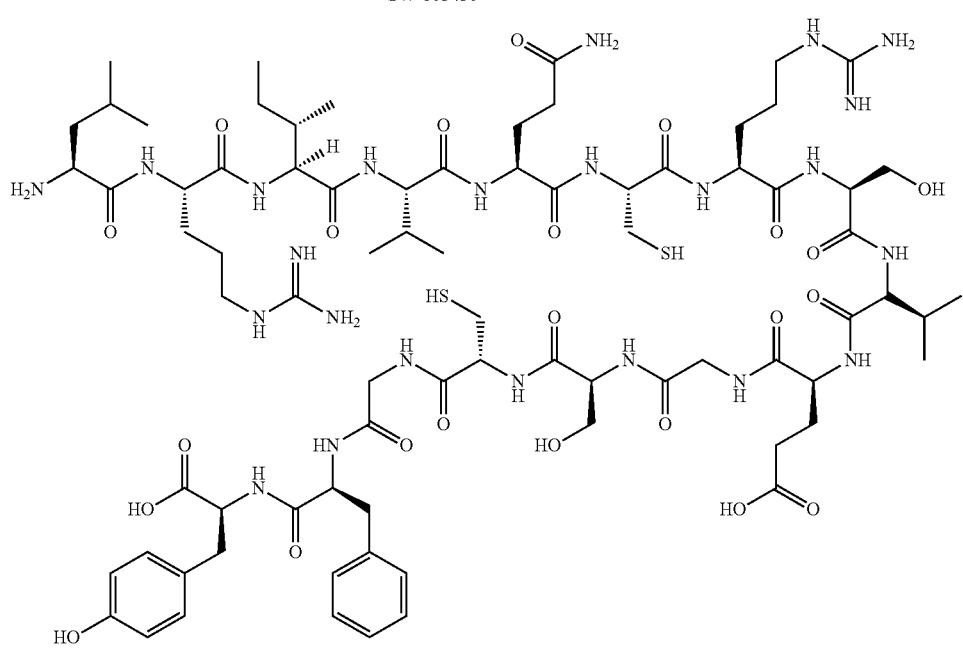
AOD-9604

-continued
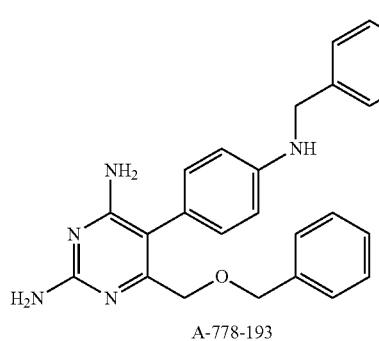
A-778-193
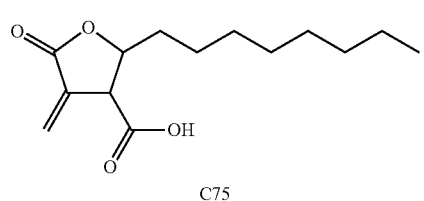
C75
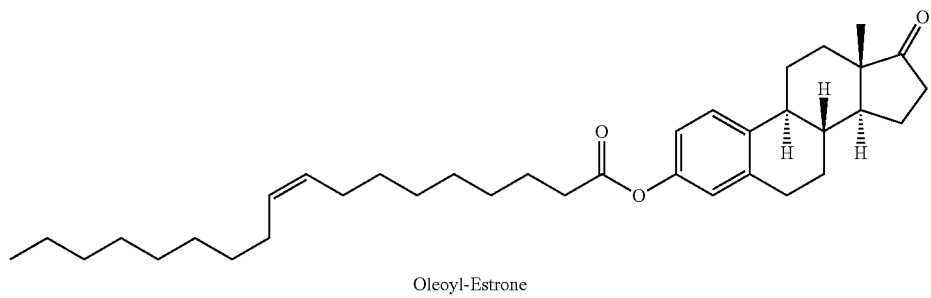
Oleoyl-Estrone
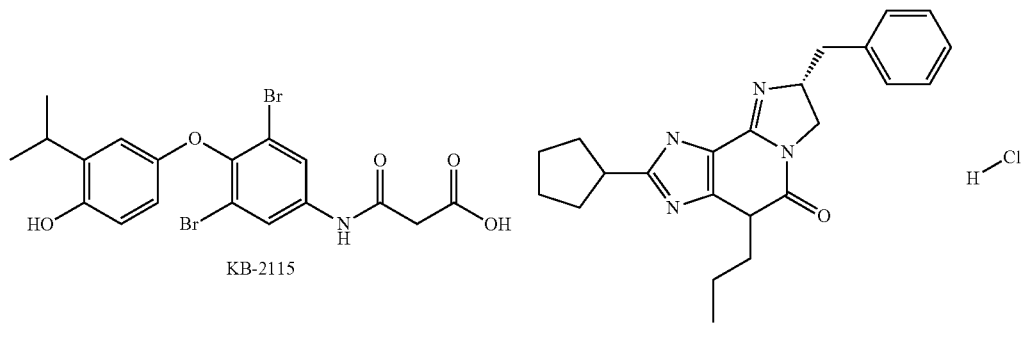
KB-2115
KCP-265
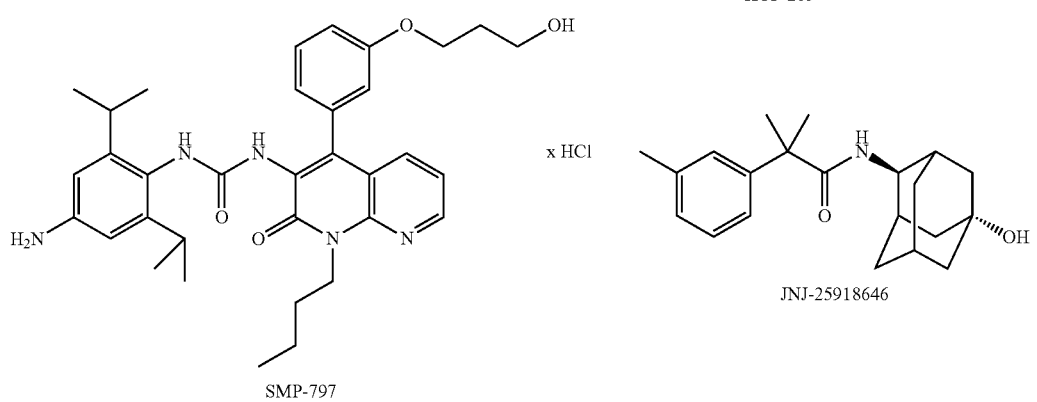
SMP-797
JNJ-25918646
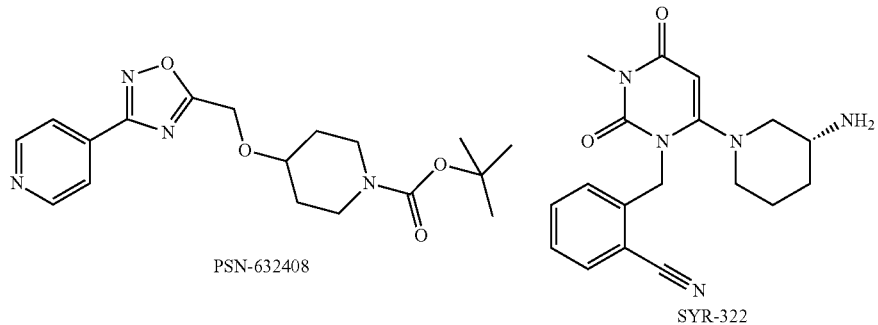
PSN-632408
SYR-322

-continued
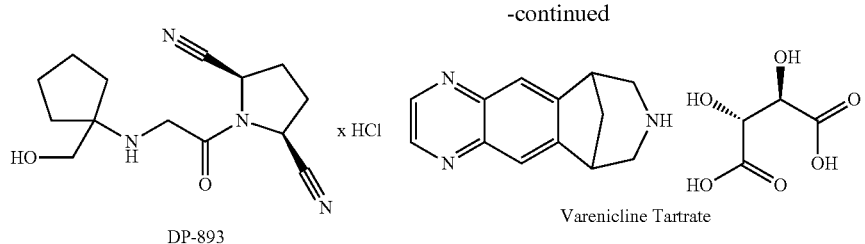
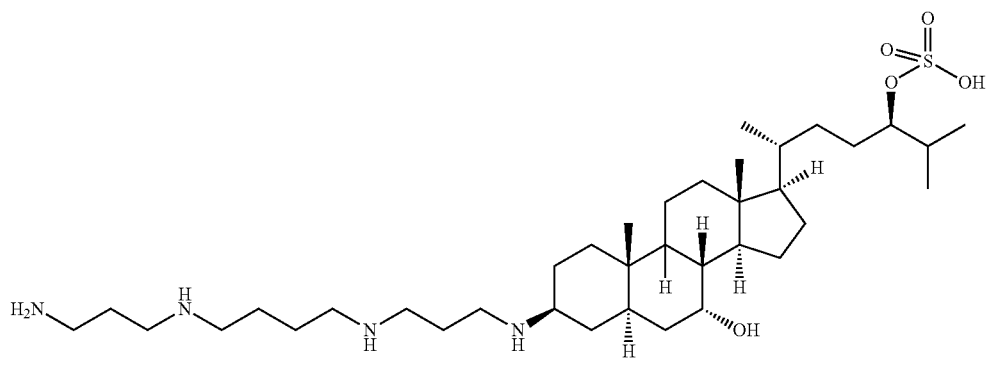
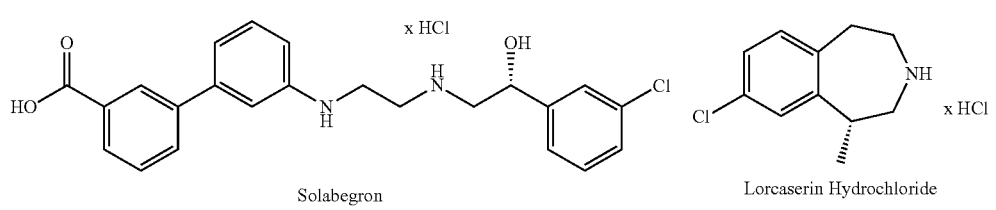
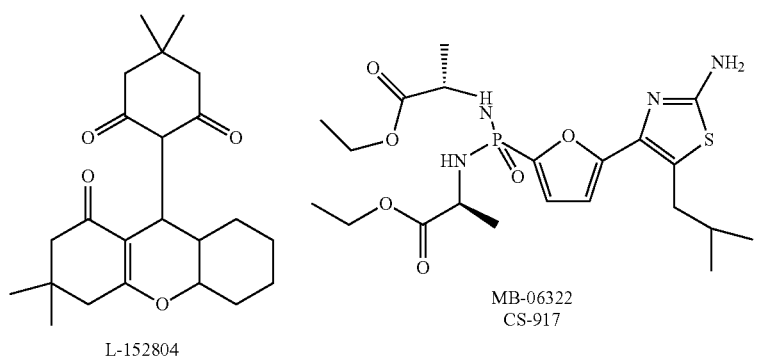
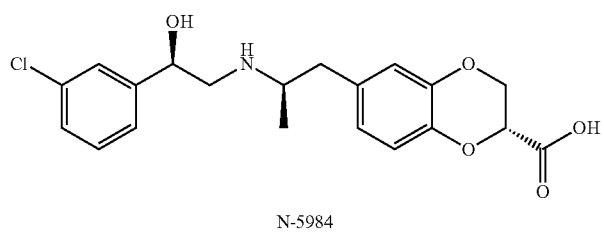
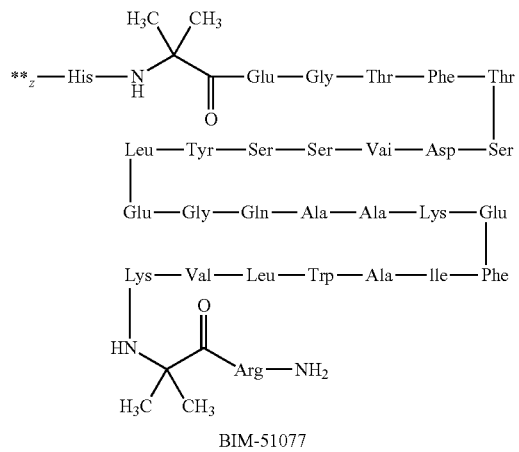

-continued
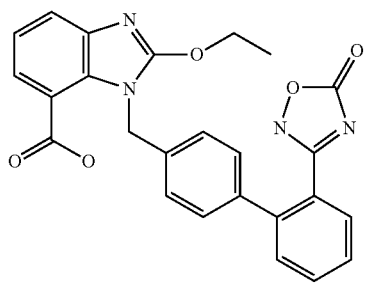
TAK-536
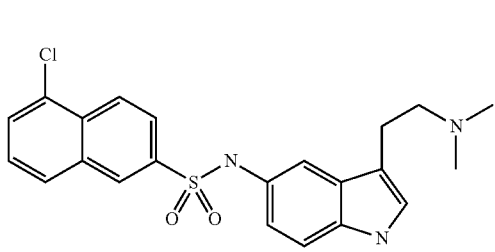
E-6837
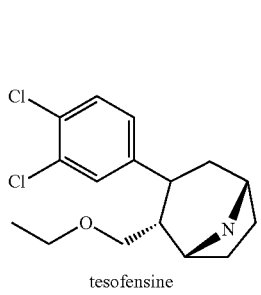
tesofensine
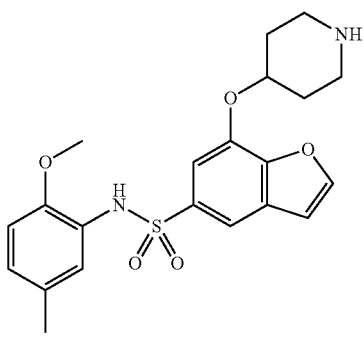
BVT-74316
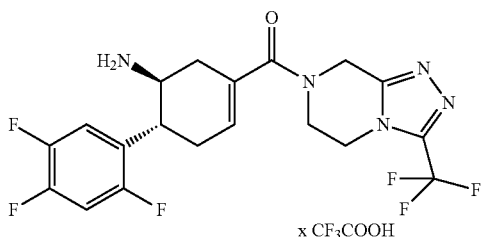
ABT-341
x CF$_3$COOH
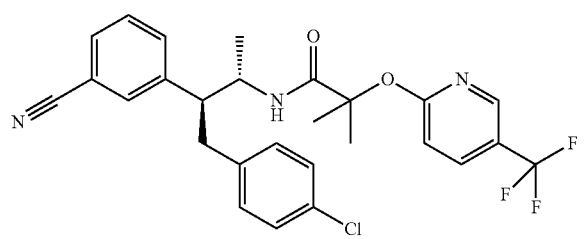
MK-0364
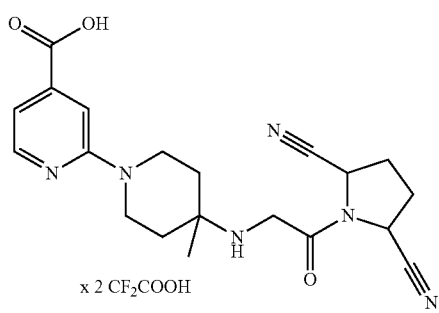
ABT-279
x 2 CF$_3$COOH
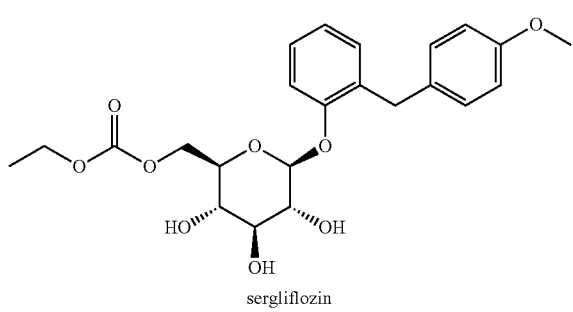
sergliflozin
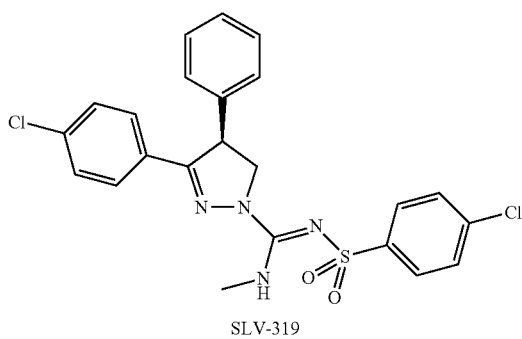
SLV-319
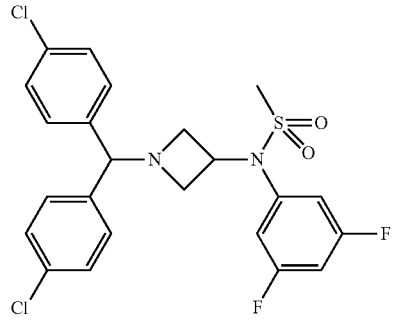
AVE 1625 (proposed INN: drinabant)

-continued
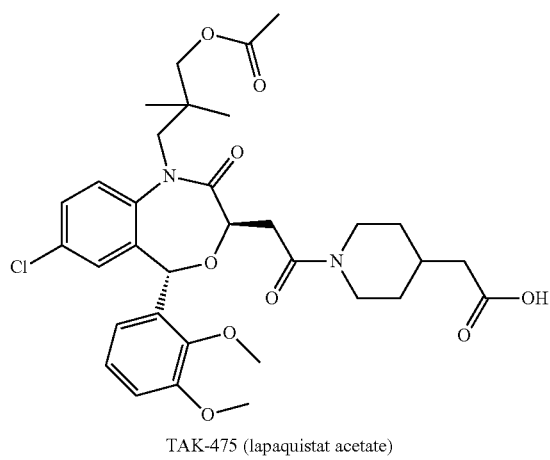
TAK-475 (lapaquistat acetate)
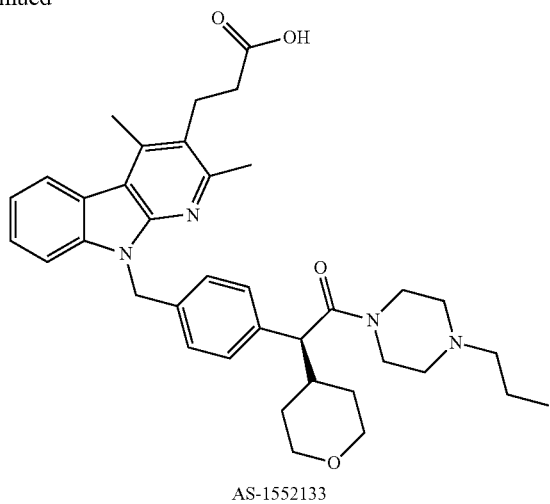
AS-1552133
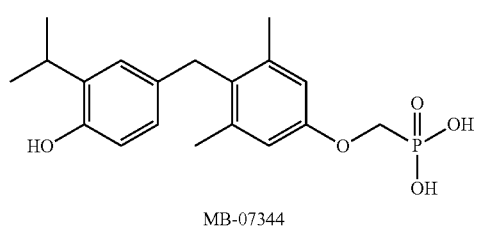
MB-07344
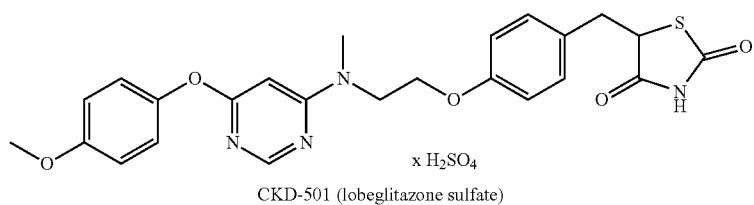
CKD-501 (lobeglitazone sulfate)
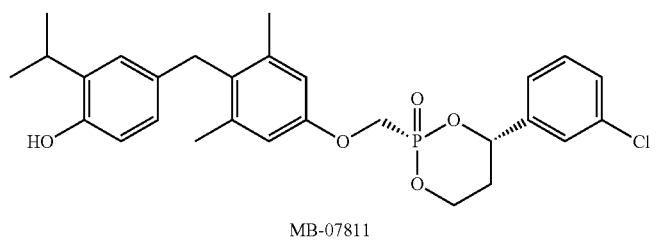
MB-07811
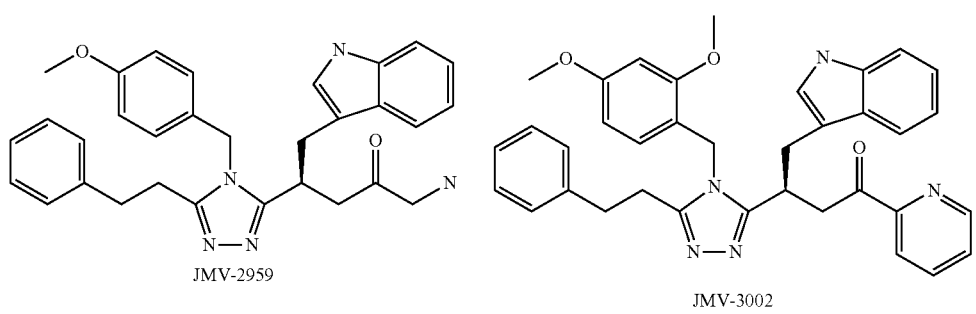
JMV-2959     JMV-3002

-continued
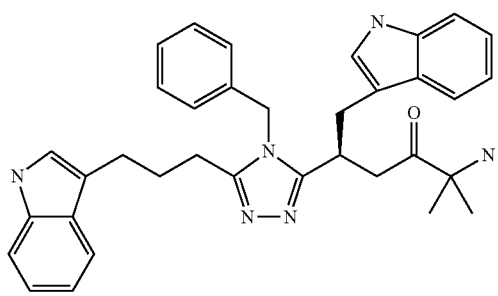
JMV-2810
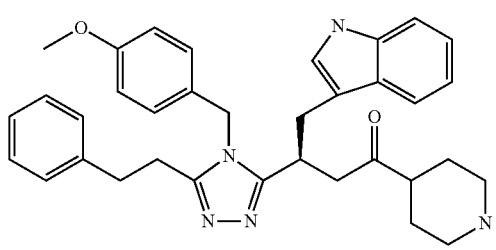
JMV-2951
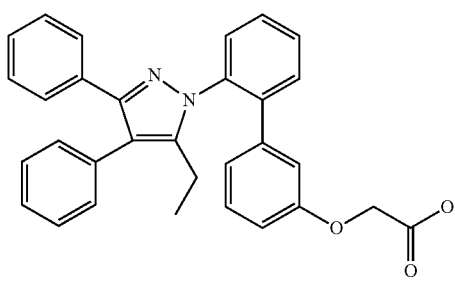
BMS-309403
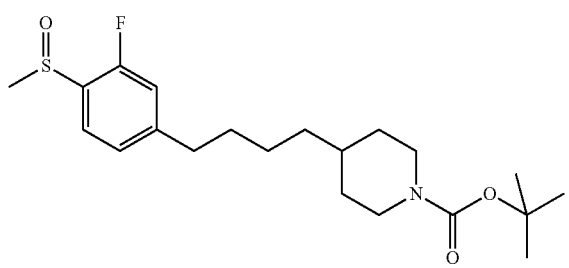
PSN-119-1
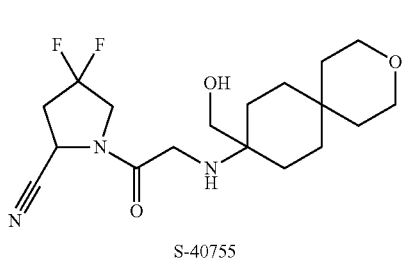
S-40755
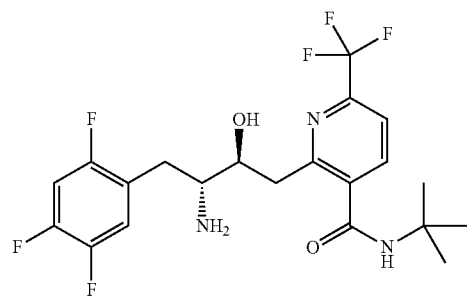
LY-2463665
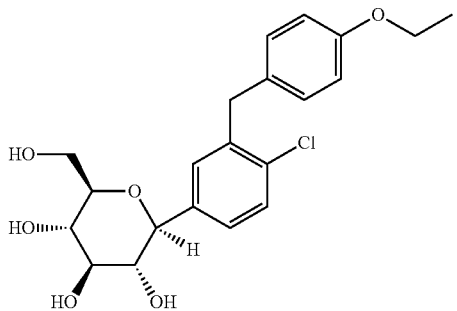
dapagliflozin, BMS-512148
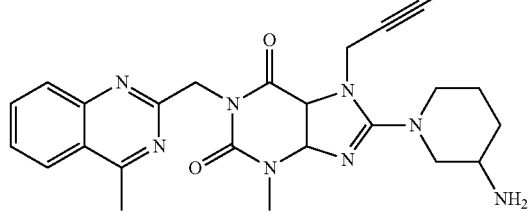
BI-1356
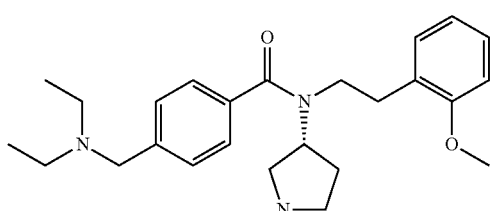
PF-426242
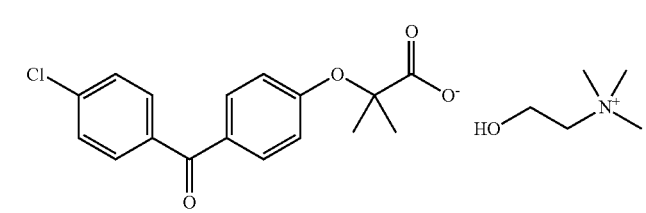
SLV-348

-continued
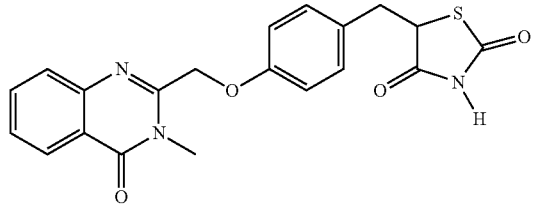
balaglitazone
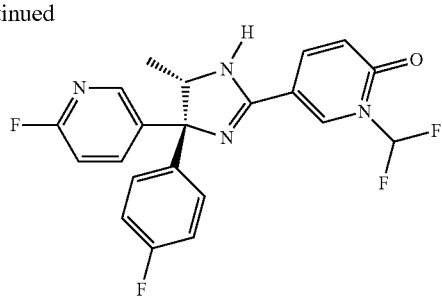
"NPY-5-BY"
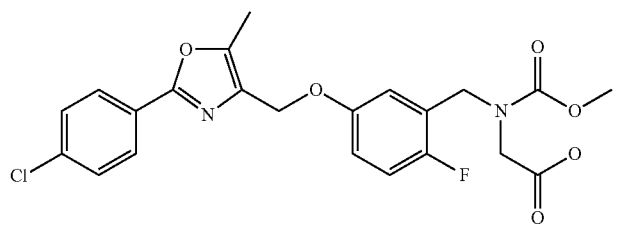
BMS-711939
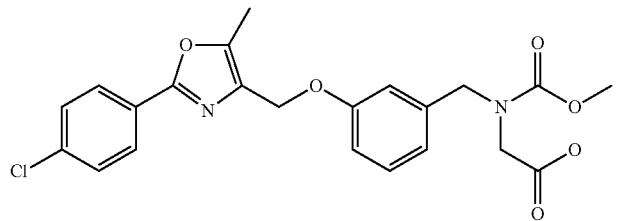
BMS-687453
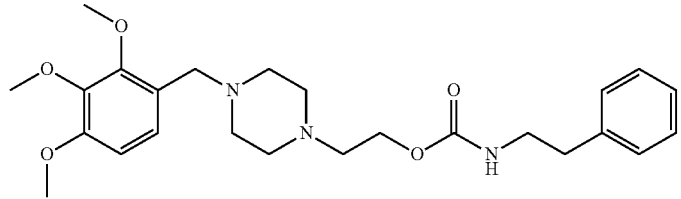
ST-3473
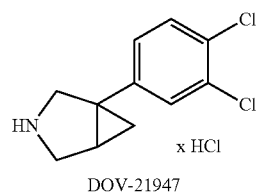
DOV-21947
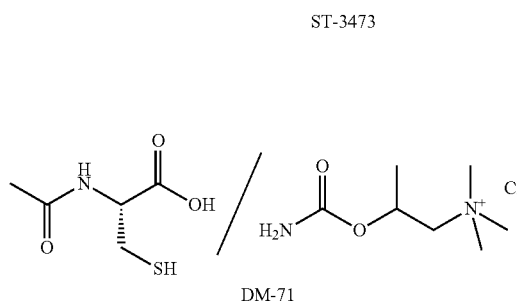
DM-71
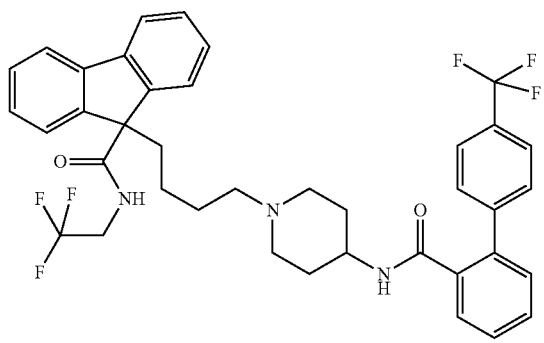
AEGR-733
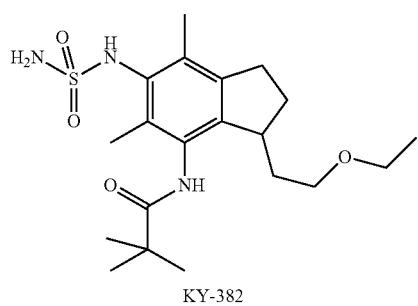
KY-382
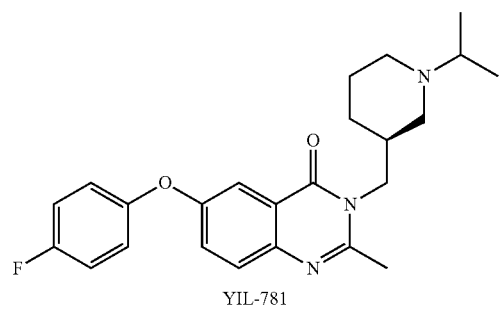
YIL-781

-continued
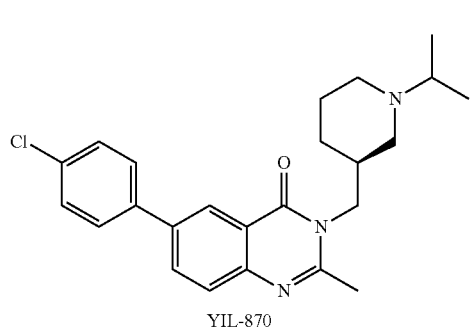
YIL-870
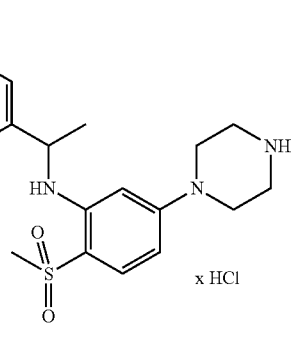
PRX-07034 x HCl
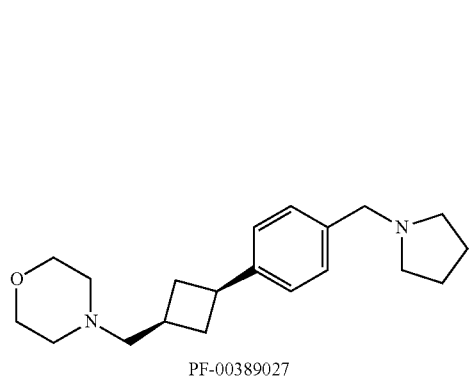
PF-00389027
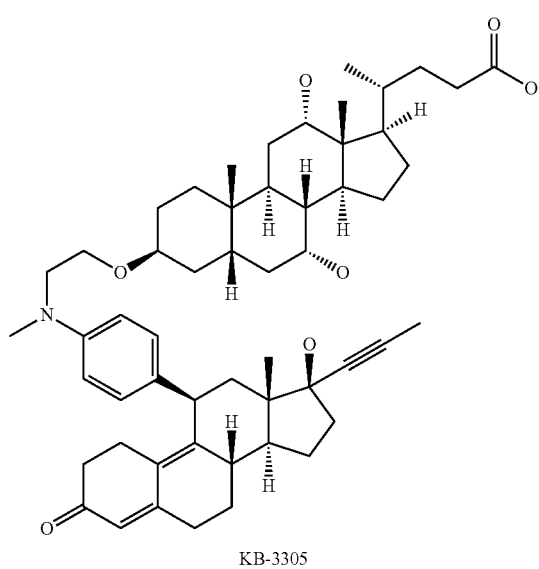
KB-3305
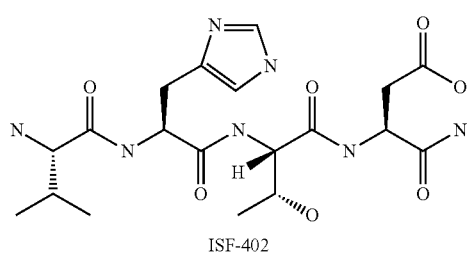
ISF-402
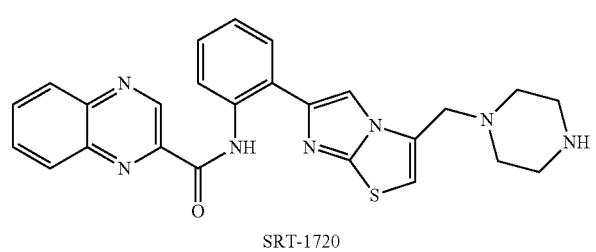
SRT-1720
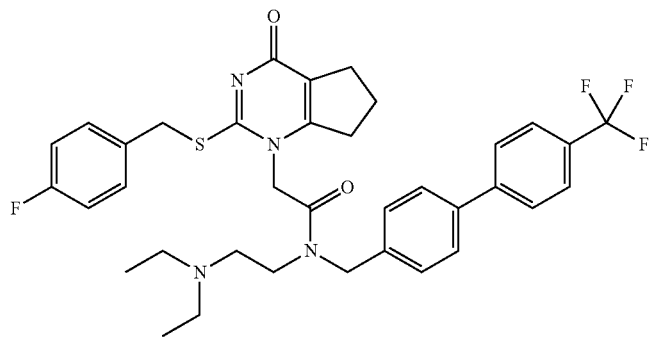
darapladib
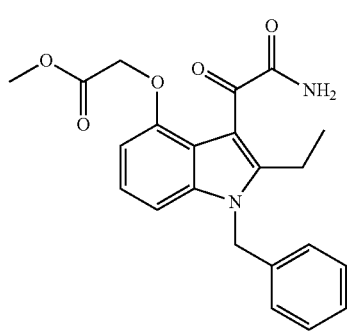
A-002

-continued
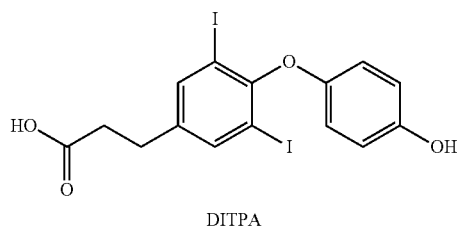
DITPA
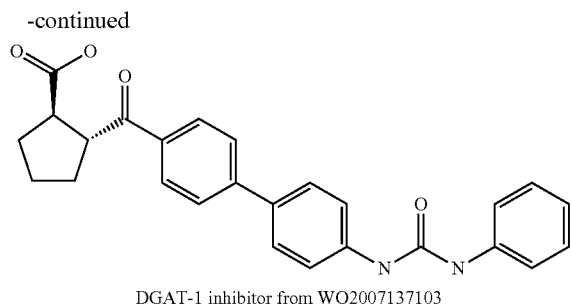
DGAT-1 inhibitor from WO2007137103
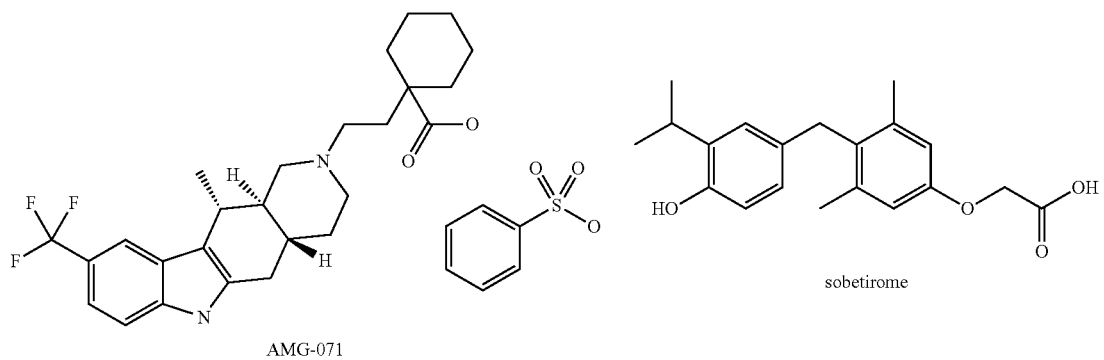
AMG-071
sobetirome
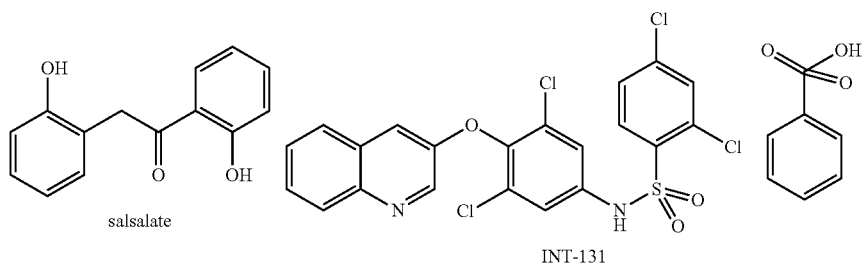
salsalate
INT-131
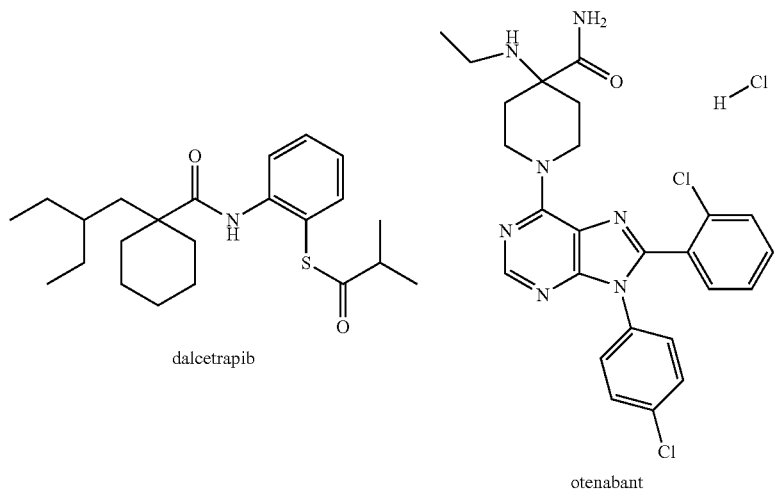
dalcetrapib
otenabant
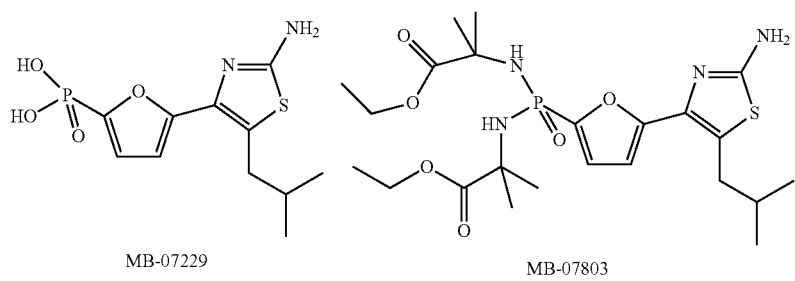
MB-07229
MB-07803

-continued
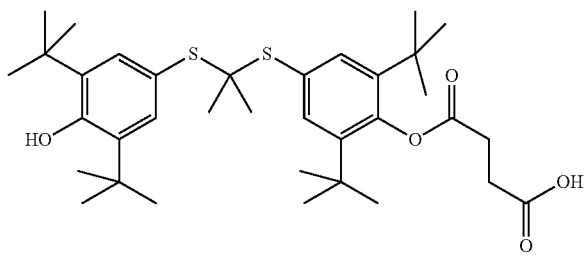
succinobucol
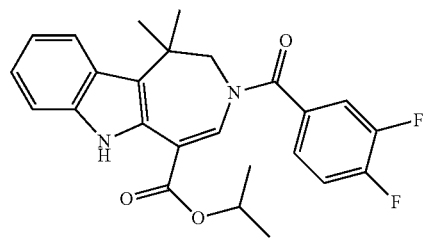
WAY-362450
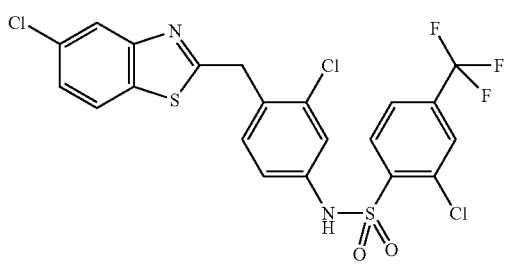
T-2384
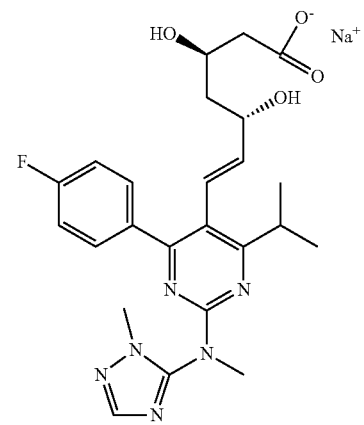
BMS-644950
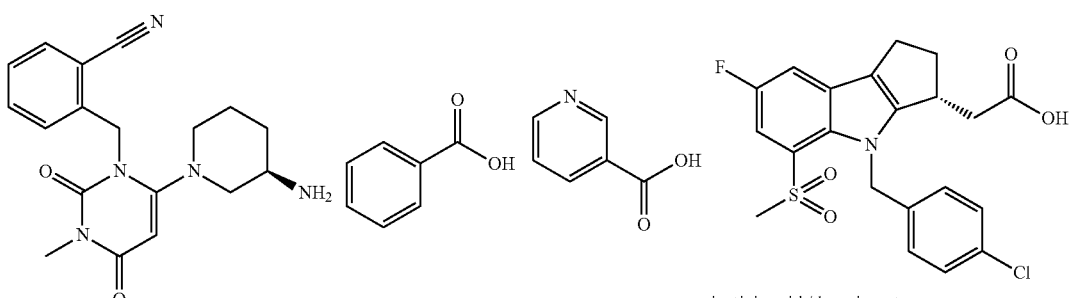
alogliptin benzoate — nicotinic acid / laropiprant
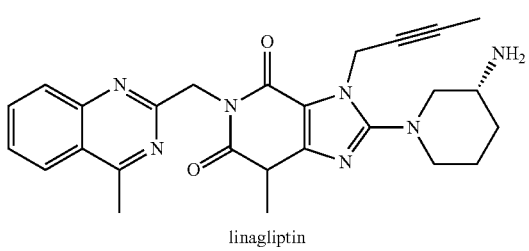
linagliptin
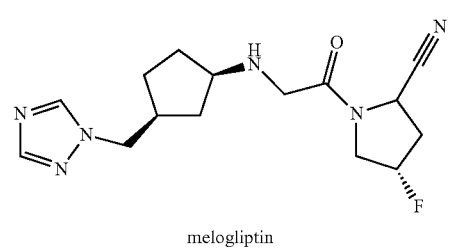
melogliptin
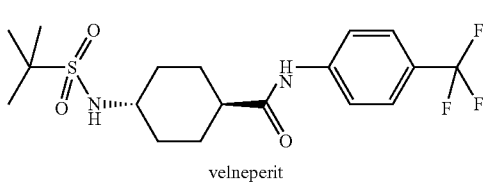
velneperit
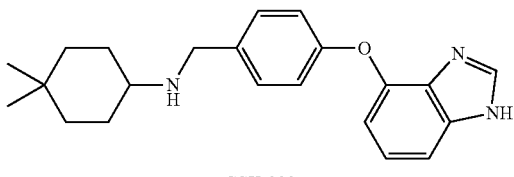
GSK-982

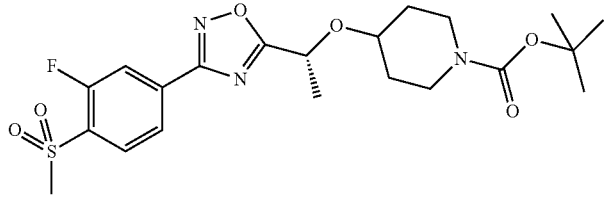

PSN-119-2

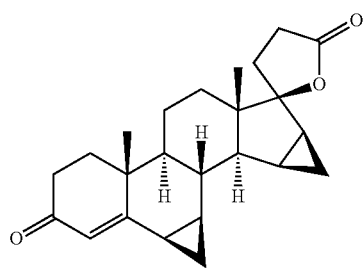

drospirenone

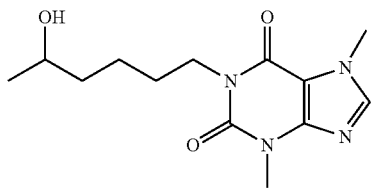

lisofylline

Also suitable are the following active ingredients for combination products:

all antiepileptic drugs specified in the Rote Liste 2007, chapter 15;

all antihypertensive drugs specified in the Rote Liste 2007, chapter 17;

all hypotensive drugs specified in the Rote Liste 2007, chapter 19;

all anticoagulant drugs specified in the Rote Liste 2007, chapter 20;

all arteriosclerosis drugs specified in the Rote Liste 2007, chapter 25;

all beta receptor blockers, calcium channel blockers and inhibitors of the renin angiotensin system specified in the Rote Liste 2007, chapter 27;

all diuretic and perfusion-promoting drugs specified in the Rote Liste 2007, chapters 36 and 37;

all withdrawal drugs/drugs for the treatment of addictive disorders specified in the Rote Liste 2007, chapter 39;

all coronary drugs and gastrointestinal drugs specified in the Rote Liste 2007, chapters 55 and 60;

all migraine drugs, neuropathy preparations and Parkinson's drugs specified in the Rote Liste 2007, chapters 61, 66 and 70.

The efficacy of the inventive compounds of the formula I was tested using the following enzyme test systems:

Test for inhibition of EL:

Preparation of EL

EL is released as a secretory protein by recombinant cell lines (CHO, HEK293) in high concentration into cell culture medium (conditioned medium). This was used as an enzyme solution after concentration.

Assay for EL Activity

For characterization of the enzymatic activity of endothelial lipase and the effect of inhibitors, the phospholipase-specific substrate 1,2-bis(4,4-difluoro-5,7-dimethyl-4-bora-3a,4a-diaza-s-indacene-3-undecanoyl)-sn-glycero-3-phosphocholine (manufacturer: Molecular Probes) was used. Hydrolysis of the A1 ester bond of this phospholipid by the enzyme releases the fluorescent dye Bodipy, which can be detected by measuring the fluorescence after separation by thin-layer chromatography on an HPTLC plate (silica gel 60, Merck) or directly in the reaction vessel. To prepare the substrate solution, 100 µg of 1,2-bis(4,4-difluoro-5,7-dimethyl-4-bora-3a,4a-diaza-s-indacene-3-undecanoyl)-sn-glycero-3-phosphocholine (manufacturer: Molecular Probes) were dissolved in 100 µl of DMSO and taken up in 2.4 mg of tripalmitin (Sigma) in 393 µl of chloroform which contained 20 mg/ml DOP—choline (1,2-dioleoyl-sn-glycero-3-phosphocholine). 39.3 µl of this lipid mixture were transferred into a fresh reaction vessel and the solvent was evaporated off. The lipid mixture was dissolved by sonicating twice in 4 ml of 200 mM TRIS-HCl, 150 mM sodium chloride, pH=7.4. The subsequent enzyme reaction was effected at 37° C. for 90 minutes. For this purpose, 20 µl of the substrate solution were incubated with 2 µl of inhibitor of appropriate concentration (dissolved in 10% DMSO; 10% DMSO solution was used as a control) and 2 µl of enzyme solution (conditioned medium). Thereafter, 4 µl of the test mixture were applied to an HPTLC plate (silica gel 60, Merck) and the fluorescent dye released was separated for detection with an eluent (diethyl ether:petroleum:acetic acid [78:22:1]). After the eluent had been evaporated off, the plate was read in a fluorescence scanner. As a measure of enzyme activity, an enhanced release of the fluorescent dye in the uninhibited reaction was observed.

As a function of the inhibitor concentration used, a reduction in the enzymatic activity was found. The inhibitor concentration at which a half-maximum enzyme activity is observed is referred to as $IC_{50}$.

In this test, the compounds from the examples exhibited the following $IC_{50}$ values:

| Example | $IC_{50}$ [nM] EL |
|---|---|
| 3 | 926 |
| 4 | 40 |
| 5 | 200 |
| 18 | 69 |
| 28 | 107 |
| 29 | 4290 |
| 37 | 148 |
| 38 | 182 |
| 39 | 120 |
| 46 | 28 |
| 50 | 138 |
| 55 | 116 |
| 59 | 264 |

-continued

| Example | IC$_{50}$ [nM] EL |
|---|---|
| 114 | 216 |
| 115 | 1380 |
| 116 | 1590 |
| 129 | 230 |
| 130 | 85 |
| 134 | 391 |
| 142 | 517 |
| 156 | 1580 |
| 161 | 80 |
| 162 | 453 |

Other Test Models Various test models can be used to test the suitability of the inventive compounds as an active pharmaceutical ingredient. Descriptions of such test models are given by way of example hereinafter.

Solubilities in Aqueous Systems

Adequate solubility of a substance in aqueous solvent systems is an important prerequisite for (reproducible) pharmacological action. Solubilities in aqueous systems can be determined by various methods. Suitable examples are solution precipitation methods ("kinetic solubility") and methods which examine the dissolution of a solid sample until equilibrium is established ("thermodynamic solubility").

a) Kinetic Solubility

In a 96-well microtiter plate, a DMSO solution of the test compound (2.5 mM; 0.5 µl) is pipetted into 200 µl of an aqueous test solution (for example phosphate-buffered saline, 10×, 1 M, Sigma, diluted to 10 mM, pH 7.4) and the turbidity is measured at the resulting theoretical concentration of the test compound of 6.25 µM using a nephelometer (for example Nephelostar Galaxy, BMG Labtech). Thereafter, the concentration of the test compound in the aqueous test solution is increased to a theoretical 12.5 µM by adding further DMSO solution (2.5 mM; 0.5 µl), and the turbidity measurement is repeated. Further additions of DMSO solutions (1 µl, 2.5 mM; 0.5 µl, 10 mM; then 9×1 µl, 10 mM, resulting in theoretical concentrations of 25 µM, 50 µM, 100 µM, 150 µM, 200 µM, 250 µM, 300 µM, 350 µM, 400 µM, 450 µM and 500 µM), with turbidity measurement between the additions, complete the measurement process.

Evaluation: The turbidity values from the nephelometer are plotted against the theoretical concentration of the test compound in the aqueous test solution. As soon as significant turbidity is detected (e.g. 5 times greater than the control value of the aqueous test solution) at any theoretical concentration, the concentration below it is stated as the solubility limit of the test compound in the test solution. The maximum possible measurement range is thus found to be at values of <6.25 µM, 6.25-500 µM and >500 µM.

Preferred inventive compounds exhibit a kinetic solubility in phosphate buffer (pH 7.4) of at least 12.5 µM, more preferably of at least 50 µM and even more preferably of at least 250 µM.

b) Thermodynamic Solubility

By HPLC-UV analysis of a dilution series of the test compound in DMSO (500 µM, 100 µM, 50 µM, 10 µM and 1 µM), the integrated UV absorption gives a linear correlation with the concentration in a calibration line. The test compound (500 µg) is shaken together with the aqueous test solution (250 µl) in a closed vessel (capacity: 1.5 ml) for 16 hours (Eppendorf Thermoshaker, 1400 rpm, 25° C., cover as a light guard). Subsequently, the sample is centrifuged at maximum speed and the supernatant is finally filtered. A sample of the filtered supernatant is analyzed directly by means of HPLC-UV analysis (see above). A further sample is analyzed after dilution (1 part by volume of supernatant, 39 parts by volume of test solution).

Evaluation: Using the calibration lines produced, the resulting integrated UV absorptions of the supernatant samples are used to calculate the concentration of the test compound in the undiluted supernatant, and it is reported as the solubility of the test compound in the respective aqueous test solution.

Examples of aqueous test solutions are demineralized water or aqueous phosphate buffers with various pH values (e.g. pH 1.2; pH 4.0; pH 6.8; pH 7.4; pH 9.0), which can be prepared by standard methods from the commercial solution (phosphate-buffered saline, 10×, Sigma), by dilution with phosphoric acid or sodium hydroxide solution. Preferred inventive compounds exhibit a solubility in phosphate buffer (pH 7.4) of at least 12.5 µM, more preferably of at least 50 µM and even more preferably of at least 250 µM.

Permeability

The test for permeability is conducted in CACO-2/TC7 cells which have been cultured (DMEM/Glutamax I/Gibco with high glucose content, HEPES 25 mM, 1% NEAA, 10% FBS, 40 µg/ml gentamycin; ambient temperature 37° C.; air humidity 95% and CO2 content 10%) on Becton Dickinson filters (24-well, uncoated) for 21 days. Permeability is examined at a concentration of the test compound of 20 µM (1% DMSO in HBSS) with a pH gradient (apical: pH 6.5 and 0.5% BSA; basolateral: pH 7.4 and 5% BSA). The analysis is effected by means of LCMS/MS. Further descriptions of the test system and references for the experimental procedure can be found in Balimane, P. V.; Drug Discovery Today 2005, 10(5), 335-343.

Inhibition of CYP Enzymes

The inhibition of CYP enzymes is determined on recombinant enzymes (obtained from Becton Dickinson) and fluorescent substrates (BD/Gentest) as recommended by the manufacturer (see website http://www.bdbiosciences.com). Further descriptions of the test system and references for the experimental procedure can be found in Zlokarnik, G.; Drug Discovery Today 2005, 10(21), 1443-1450.

Metabolic Stability

Metabolic stability is determined by incubating the test compound (5 µM) at 37° C. with microsomal liver fractions (1 mg/ml protein with 0.1% w/v BSA; 1 mM NADPH, 0.5% DMSO). Analysis at incubation time 0 and 20 minutes is effected by means of LCMS/MS. Further descriptions of the test system and references for the experimental procedure can be found in Plant, N.; Drug Discovery Today 2004, 9(7), 328-336 and Lau, Y. Y. et al.; Pharmaceutical Res. 2002, 19(11), 1606-1610.

Plasma Stability

Plasma stability is determined by incubating the test compound at 37° C. with human plasma (10 mM stock solution of the test compound in DMSO). Working solution: concentration 1000 ng/l diluted in water/acetonitrile/DMSO 79/20/1 v/v/v).

Analysis at incubation time 0 h, 1 h and 4 h is effected by means of LCMS/MS. The incubation is conducted in multititer plates (MTP) with well capacity 0.8 ml. The 1 h and 4 h samples: 5 µl of the working solution (10 wells) are mixed with 45 µl of plasma and covered with a lid during incubation.

The 0 h sample: 5 µl of the working solution (10 wells) are mixed with 300 µl of acetonitrile and then 45 µl of plasma are added, and the plate is sealed with a removable film and mixed.

The reaction is stopped by rapid cooling (ice bath, 0° C., 1 min) and addition of 300 µl of precooled acetonitrile.

Analysis:

The plates are centrifuged at 10° C. and 1734 g for 20 min centrifuged. 220 µl of the supernatant are transferred to an MTP (0.3 ml).

LC/MS-MS analyses are undertaken in the following sequence: 4 h-1 h-0 h sample. Calculation of the percentage of hydrolyzed compound:

$$[\% \text{ hydrolysis}] = \left[1 - \left(\frac{1 \text{ h or } 4 \text{ h peak area}}{0 \text{ h peak area}}\right)\right] \times 100$$

Chemical Stability

The chemical stability of the compounds was tested in phosphate buffer over 5 hours. Sample preparation and procedure Standard:

5 µl of a 10 mM DMSO stock solution were diluted with 995 µl of acetonitrile to give a final concentration of 50 µM. This solution was analyzed on a liquid chromatography (LC) column as described below.

Test Sample:

5 µl of a 10 mM DMSO stock solution of the compound to be tested were diluted with 995 µl of pH 7.4 phosphate buffer in 50% acetonitrile to give a final concentration of 50 µM. This solution was kept at 25° C. for 5 h and then the content of starting compound was determined by LC.

Experimental Conditions:

Instrument: Waters Acquity Ultra Performance LC

Detector: Waters Acquity Ultra Performance LC PDA detector

Software: Empower2

Column: Waters Acquity BEH C18 1.7 µm 1×50 mm

Eluent A: water/0.05% trifluoroacetic acid

Eluent B acetonitrile/0.035% trifluoroacetic acid

Gradients:

| Time [min] | % A | % B |
|---|---|---|
| 0.0 | 98 | 2 |
| 0.05 | 98 | 2 |
| 1.8 | 2 | 98 |
| 2.5 | 2 | 98 |
| 2.55 | 98 | 2 |

Flow rate: 0.3 ml/min

Detection: 210-450 nm; ex. 220/254 nm

Column temperature: 40° C.

Autosampler temperature: 25° C.

Injection volume: 2 µl

Process for Preparation

The inventive compounds of the formula I are synthesized by methods known per se. The azolopyridinols II can be reacted with isocyanates III (method A), or acylated with carbamoyl chlorides (method B). They can also in two stages by acylation with phosgene or phosgene equivalents such as trichloromethyl chlorocarbonate, ditrichloromethyl carbonate, 4-nitrophenyl chloroformate and further reaction of the resulting azolecarboxylic acid derivatives with amines (method C).

Method A:

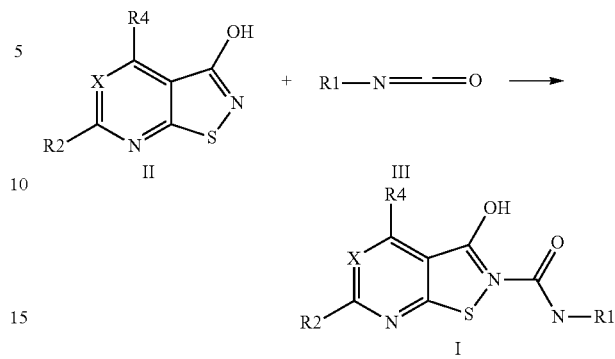

Method B:

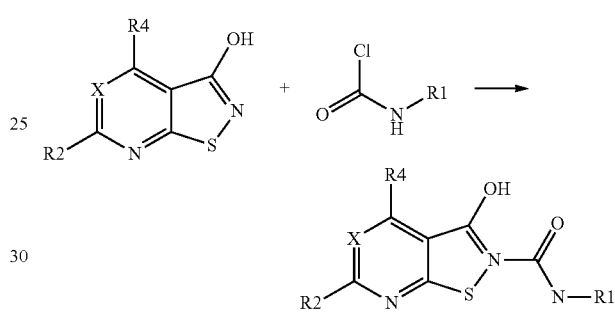

Method C:

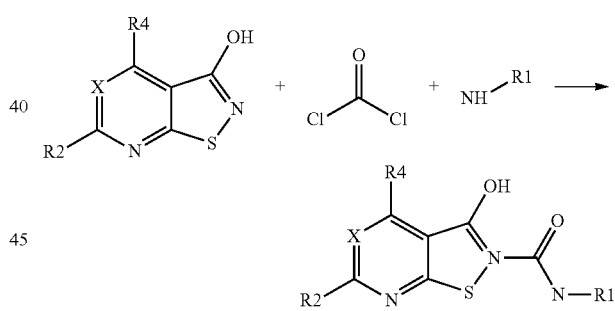

Since these reactions generally release acids, it is advisable to accelerate them by adding bases such as pyridine, triethylamine, sodium hydroxide solution or alkali metal carbonates. The reactions can be conducted within wide temperature ranges. It has generally been found to be advantageous to work at 0° C. up to the boiling point of the solvent used. The solvents used may, for example, be methylene chloride, THF, DMF, toluene, ethyl acetate, n-heptane, dioxane, diethyl ether or pyridine. If anhydrous conditions are employed, strong bases such as lithium hydride, sodium hydride or potassium tert-butoxide in aprotic solvents such as THF or DMF have also been found to be useful.

The examples adduced below serve to illustrate the invention, but without restricting it.

Synthesis of the Azolopyridinol Units

The azolopyridinols of the formula II (X=CH, N) can be obtained from correspondingly substituted mercaptonicotinic acids (X=CH) or 4-mercaptopyrimidine-5-carboxylic acids (X=N) by reaction with diphenylphosphoryl azide.

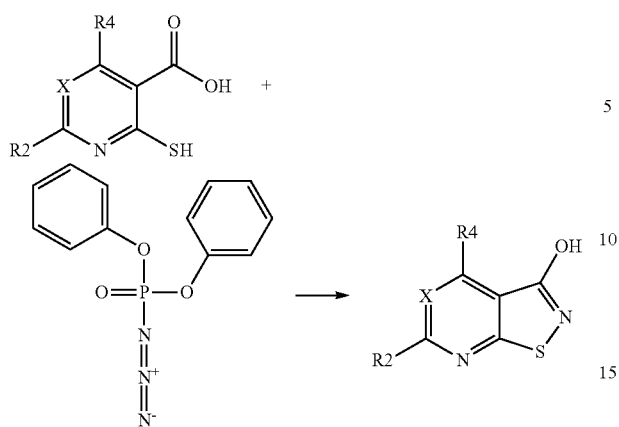

Alternatively, azolopyridinols are also obtained by heating 3-cyano-2-mercaptopyridines of the formula IV in 98% sulfuric acid.

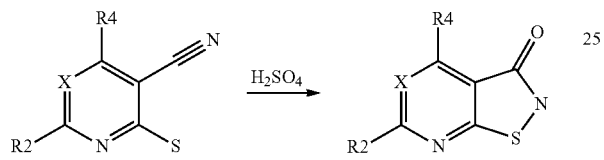

Azolopyridin-3-ol derivatives II are also commercially available or can be prepared by processes known from the literature (e.g. L. Baiocchi, G. Corsi Synthesis (1978) 633-648; I. Sekikawa et al. J. Het. Chem. (1973) 931-932; A. Dornow, M. Siebrecht, Chem. Ber. (1960) 1106-1110; M. Tilser, B. Stanovnik, Z. Zrimsek, Heterocycles (1979) 217-219; K. Bowden, G. Crank, W, J. Roos, J. Chem. Soc. 1968, 172-185).

Synthesis of the Isocyanates

The isocyanates used are either commercially available or can be prepared from corresponding amines by reaction with phosgene in toluene, THF or acetonitrile under reflux.

The amines used may again be commercially available or be obtained by reduction from cyanides, or by reductive amination from ketones.

Reaction of the isocyanates with the azolopyridinols to give the azolopyridinoneureas The inventive 3-oxo-3H-isothiazolo[5,4-b]pyridine-2-carboxamides and 3-oxo-3H-isothiazolo[5,4-d]pyrimidine-2-carboxamides are obtained by reacting the azolopyridinones of the formula II with isocyanates.

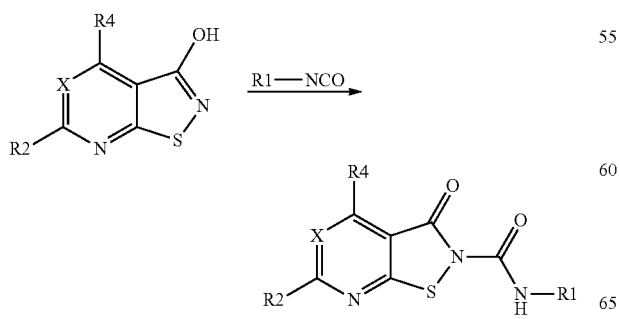

Azolopyridinone Units:
Method A

Compound 1: isothiazolo[5,4-b]pyridin-3-ol (1)

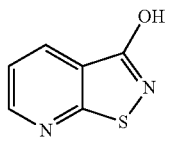

To a solution of diphenylphosphoryl azide (6.9 ml, 32 mmol) in pyridine (50 ml) and triethylamine (4.5 ml) is added, at 0° C., 2-mercaptonicotinic acid (5 g, 32 mmol) in portions. After 30 min, the ice cooling is removed and the mixture is stirred at 25° C. for a further 16 h. The solvent is distilled off under reduced pressure and the residue, a viscous oil, is admixed with methyl tert-butyl ether. While stirring, EtOAc/H$_2$O is added and the mixture is stirred for another 15 min. The resulting pale yellow solid is filtered off with suction and dried.

Yield: 2.57 g

Method B

Compound 2:
4,6-dimethylisothiazolo[5,4-b]pyridin-3-ol (2)

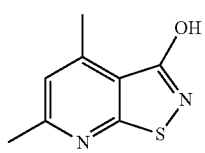

3-Cyano-4,6-dimethyl-2-mercaptopyridine (4.7 g, 28.6 mmol) is dissolved in H$_2$SO$_4$(60 ml, 98%) and then stirred at 105° C. for 3 h. The reaction is monitored by HPLC-MS. The reaction solution is cooled to 25° C. and then poured onto ice. The product eventually (15 min) precipitates out as a voluminous solid and is filtered off with suction and washed with H$_2$O. The residue is taken up with aqueous Na$_2$CO$_3$ solution (pH 8-9) and the product is extracted with EtOAc. The solvent is distilled off under reduced pressure and the residue (white solid) is dried (Na$_2$SO$_4$).

Yield: 1.16 g (22.5%)

Compound 3: 6-cyclopropyl-4-methylisothiazolo[5,4-d]pyrimidin-3-ol (3)

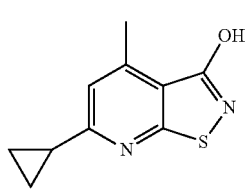

Compound 3 is prepared by method A from 2-cyclopropyl-4-mercapto-6-methylpyrimidinecarboxylic acid.

Compound 4: 6-phenylisothiazolo[5,4-b]pyridin-3-ol (4)

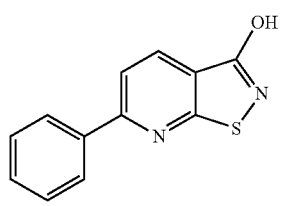 [SMILES: Oc1nsc2nc(-c3ccccc3)ccc12]

Compound 4 is prepared by method A from 2-mercapto-6-phenylnicotinic acid.

Compound 5: 6-methyl-3-oxo-2,3-dihydroisothiazolo[5,4-b]pyridine-4-carboxylic acid (5)

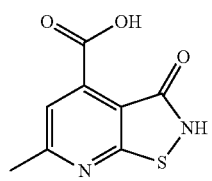

Compound 5 is prepared by method B from ethyl 3-cyano-2-mercapto-6-methylisonicotinate.

Reaction of the isocyanates with the azolopyridinones to give the azolopyridinoneureas

EXAMPLE 1

N-[3-(furan-2-ylmethoxymethyl)benzyl]-3-oxo-3H-isothiazolo[5,4-b]pyridine-2-carboxamide (6)

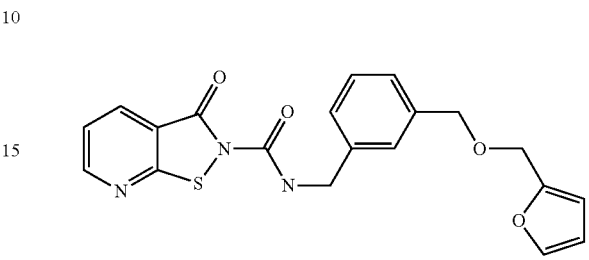

A solution of 3-(furan-2-ylmethoxymethyl)benzylamine (218 mg, 1 mmol) in toluene (10 ml) is admixed at 25° C. with phosgene (5 ml, 10 mmol; 20% solution in toluene) and heated to reflux. After 3 h, the mixture is filtered and the filtrate is concentrated. The residue is taken up in THF (25 ml) and admixed with compound 1 (122 mg, 0.8 mmol). The mixture is stirred at 60° C. for 3 h. The reaction is monitored by HPLC-MS. The solvent is reduced, and the product crystallizes. C20H17N3O4S, Mw 395.44. Yield: 239 mg (75.7%).

The examples listed hereinafter were prepared analogously. In cases where the product did not crystallize directly, the product was purified by chromatography.

| Example No. | Structure | Name<br>Empirical formula<br>Molar mass [g/mol] |
|---|---|---|
| 2 | 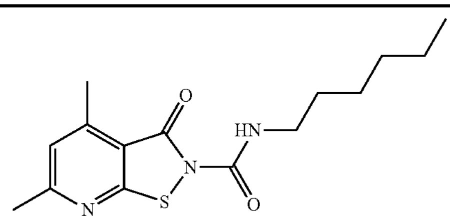 | 4,6-Dimethyl-3-oxo-3H-isothiazolo[5,4-b]pyridine-2-carboxylic acid hexylamide<br>C15H21N3O2 307.416 |
| 3 | 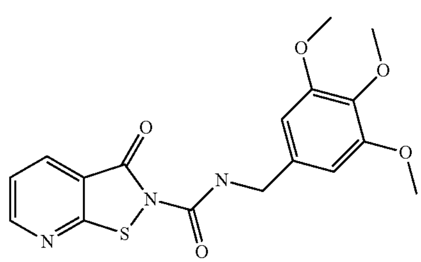 [SMILES: COc1cc(CNC(=O)n2sc3ncccc3c2=O)cc(OC)c1OC] | 3-Oxo-3H-isothiazolo[5,4-b]pyridine-2-carboxylic acid 3,4,5-trimethoxybenzylamide<br>C17H17N3O5S 375.406 |
| 4 | 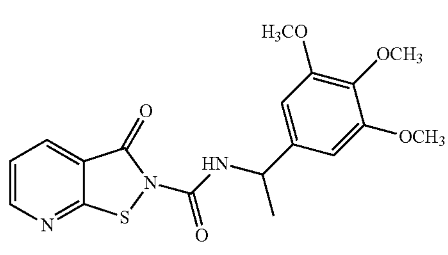 [SMILES: COc1cc(C(C)NC(=O)n2sc3ncccc3c2=O)cc(OC)c1OC] | 3-Oxo-3H-isothiazolo[5,4-b]pyridine-2-carboxylic acid [1-(3,4,5-trimethoxy-phenyl)-ethyl]-amide<br>C18H19N3O5S 389.433 |

-continued

| Example No. | Structure | Name<br>Empirical formula<br>Molar mass [g/mol] |
|---|---|---|
| 5 | 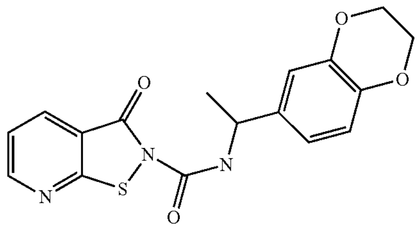 [SMILES: CC(NC(=O)n1sc2ncccc2c1=O)c1ccc2c(c1)OCCO2] | 3-Oxo-3H-isothiazolo[5,4-b]pyridine-2-carboxylic acid [1-(2,3-dihydro-benzo[1,4]dioxin-6-yl)-ethyl]-amide<br>C17H15N3O4S 357.391 |
| 6 | 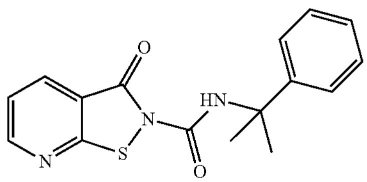 [SMILES: CC(C)(NC(=O)n1sc2ncccc2c1=O)c1ccccc1] | 3-Oxo-3H-isothiazolo[5,4-b]pyridine-2-carboxylic acid (1-methyl-1-phenyl-ethyl)-amide<br>C16H15N3O2S 313.381 |
| 7 | 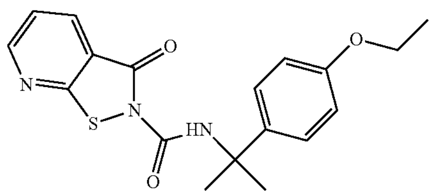 [SMILES: CCOc1ccc(C(C)(C)NC(=O)n2sc3ncccc3c2=O)cc1] | 3-Oxo-3H-isothiazolo[5,4-b]pyridine-2-carboxylic acid (1-methyl-1-phenyl-ethyl)-amide<br>C18H19N3O3S 357.434 |
| 8 | 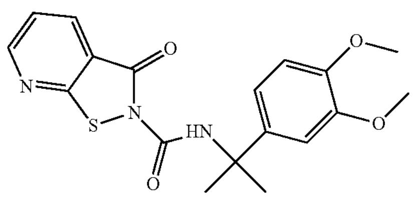 [SMILES: COc1ccc(C(C)(C)NC(=O)n2sc3ncccc3c2=O)cc1OC] | 3-Oxo-3H-isothiazolo[5,4-b]pyridine-2-carboxylic acid [1-(3,4-dimethoxy-phenyl)-1-methyl-ethyl]-amide<br>C18H19N3O4S 373.434 |
| 9 | 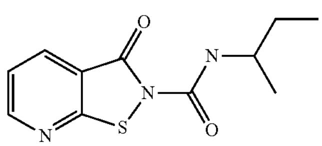 [SMILES: CCC(C)NC(=O)n1sc2ncccc2c1=O] | 3-Oxo-3H-isothiazolo[5,4-b]pyridine-2-carboxylic acid sec-butylamide<br>C11H13N3O2S 251.309 |
| 10 | 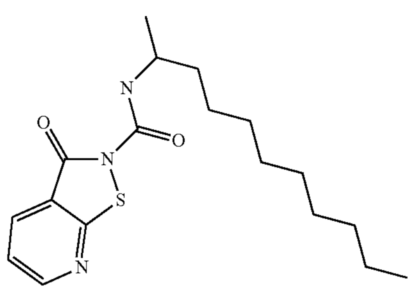 [SMILES: CCCCCCCCCC(C)NC(=O)n1sc2ncccc2c1=O] | 3-Oxo-3H-isothiazolo[5,4-b]pyridine-2-carboxylic acid (1-methyl-decyl)-amide<br>C18H27N3O2S 349.499 |
| 11 | 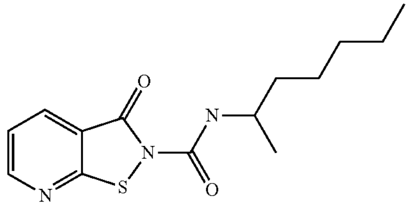 [SMILES: CCCCCC(C)NC(=O)n1sc2ncccc2c1=O] | 3-Oxo-3H-isothiazolo[5,4-b]pyridine-2-carboxylic acid (1-methyl-hexyl)-amide<br>C14H19N3O2S 293.39 |

-continued

| Example No. | Structure | Name<br>Empirical formula<br>Molar mass [g/mol] |
|---|---|---|
| 12 | 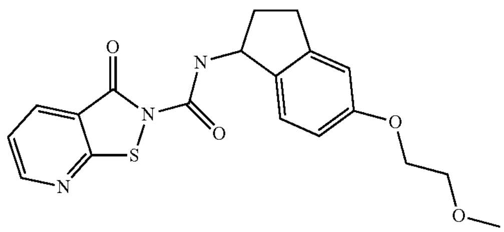 [SMILES: COCCOc1ccc2c(c1)CCC2NC(=O)n1sc2ncccc2c1=O] | 3-Oxo-3H-isothiazolo[5,4-b]pyridine-2-carboxylic acid [5-(2-methoxy-ethoxy)-indan-1-yl]-amide<br>C19H19N3O4S 385.445 |
| 13 | 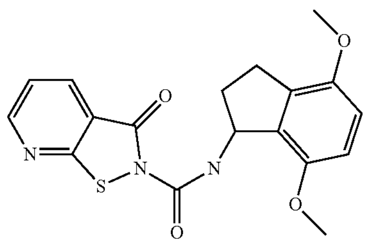 [SMILES: COc1ccc(OC)c2c1CCC2NC(=O)n1sc2ncccc2c1=O] | 3-Oxo-3H-isothiazolo[5,4-b]pyridine-2-carboxylic acid (4,7-dimethoxy-indan-1-yl)-amide<br>C18H17N3O4S 371.418 |
| 14 | 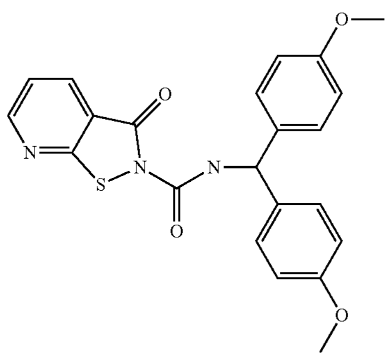 [SMILES: COc1ccc(C(NC(=O)n2sc3ncccc3c2=O)c2ccc(OC)cc2)cc1] | 3-Oxo-3H-isothiazolo[5,4-b]pyridine-2-carboxylic acid [bis-(4-methoxy-phenyl)-methyl]-amide<br>C22H19N3O4S 421.478 |
| 15 | 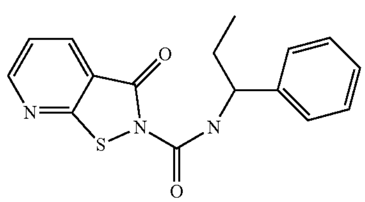 [SMILES: CCC(NC(=O)n1sc2ncccc2c1=O)c1ccccc1] | 3-Oxo-3H-isothiazolo[5,4-b]pyridine-2-carboxylic acid (1-phenyl-propyl)-amide<br>C16H15N3O2S 313.381 |
| 16 | 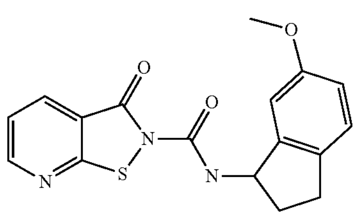 [SMILES: COc1ccc2c(c1)C(NC(=O)n1sc3ncccc3c1=O)CC2] | 3-Oxo-3H-isothiazolo[5,4-b]pyridine-2-carboxylic acid (6-methoxy-indan-1-yl)-amide<br>C17H15N3O3S 341.391 |
| 17 | 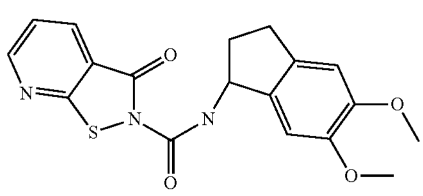 [SMILES: COc1cc2c(cc1OC)C(NC(=O)n1sc3ncccc3c1=O)CC2] | 3-Oxo-3H-isothiazolo[5,4-b]pyridine-2-carboxylic acid (5,6-dimethoxy-indan-1-yl)-amide<br>C18H17N3O4S 371.418 |

-continued

| Example No. | Structure | Name / Empirical formula / Molar mass [g/mol] |
|---|---|---|
| 18 | 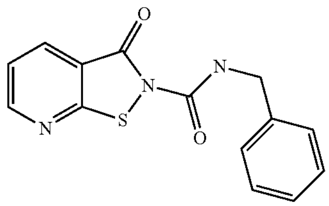 [SMILES: O=C(NCc1ccccc1)n1sc2ncccc2c1=O] | 3-Oxo-3H-isothiazolo[5,4-b]pyridine-2-carboxylic acid benzylamide<br>C14H11N3O2S 285.327 |
| 19 | 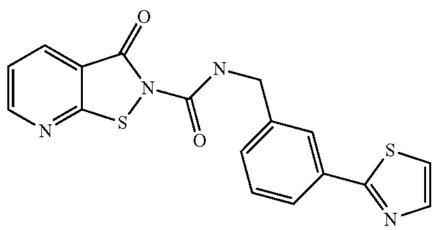 [SMILES: O=C(NCc1cccc(-c2nccs2)c1)n1sc2ncccc2c1=O] | 3-Oxo-3H-isothiazolo[5,4-b]pyridine-2-carboxylic acid 3-thiazol-2-yl-benzylamide<br>C17H12N4O2S2 368.439 |
| 20 | 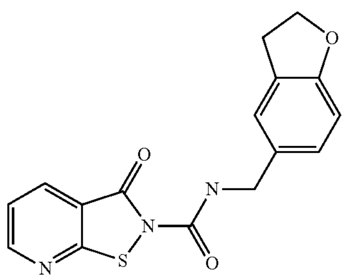 [SMILES: O=C(NCc1ccc2c(c1)CCO2)n1sc2ncccc2c1=O] | 3-Oxo-3H-isothiazolo[5,4-b]pyridine-2-carboxylic acid (2,3-dihydro-benzofuran-5-ylmethyl)-amide<br>C16H13N3O3S 327.364 |
| 21 | 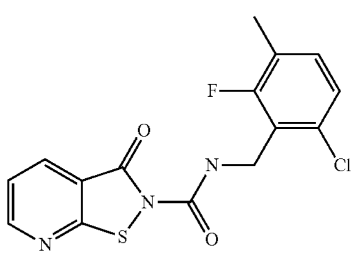 [SMILES: Cc1ccc(Cl)c(CNC(=O)n2sc3ncccc3c2=O)c1F] | 3-Oxo-3H-isothiazolo[5,4-b]pyridine-2-carboxylic acid 6-chloro-2-fluoro-3-methyl-benzylamide<br>C15H11ClFN3O2 351.789 |
| 22 | 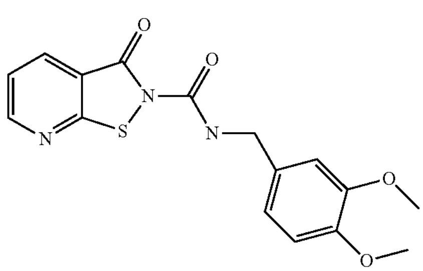 [SMILES: COc1ccc(CNC(=O)n2sc3ncccc3c2=O)cc1OC] | 3-Oxo-3H-isothiazolo[5,4-b]pyridine-2-carboxylic acid 3,4-dimethoxy-benzylamide<br>C16H15N3O4S 345.38 |
| 23 | 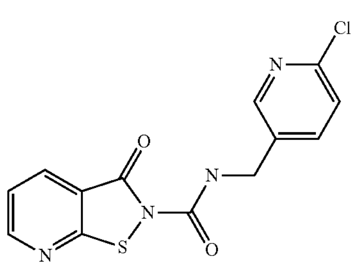 [SMILES: O=C(NCc1ccc(Cl)nc1)n1sc2ncccc2c1=O] | 3-Oxo-3H-isothiazolo[5,4-b]pyridine-2-carboxylic acid (6-chloro-pyridin-3-ylmethyl)-amide<br>C13H9ClN4O2S 320.759 |

-continued

| Example No. | Structure | Name<br>Empirical formula<br>Molar mass [g/mol] |
|---|---|---|
| 24 | 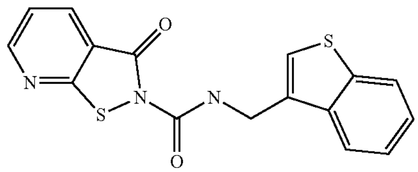 [SMILES: O=C(NCc1csc2ccccc12)n1sc2ncccc2c1=O] | 3-Oxo-3H-isothiazolo[5,4-b]pyridine-2-carboxylic acid (benzo[b]thiophen-3-ylmethyl)-amide<br>C16H11N3O2S2 341.413 |
| 25 | 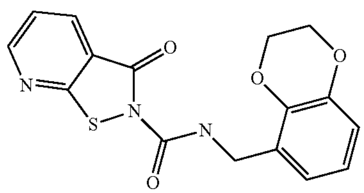 [SMILES: O=C(NCc1cccc2c1OCCO2)n1sc2ncccc2c1=O] | 3-Oxo-3H-isothiazolo[5,4-b]pyridine-2-carboxylic acid (2,3-dihydro-benzo[1,4]dioxin-5-ylmethyl)-amide<br>C16H13N3O4S 343.364 |
| 26 | 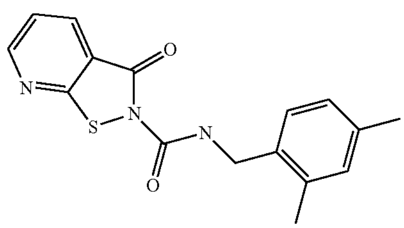 [SMILES: Cc1ccc(CNC(=O)n2sc3ncccc3c2=O)c(C)c1] | 3-Oxo-3H-isothiazolo[5,4-b]pyridine-2-carboxylic acid 2,4-dimethyl-benzylamide<br>C16H15N3O2S 313.381 |
| 27 | 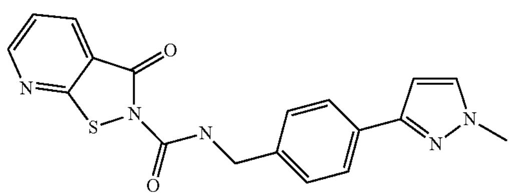 [SMILES: Cn1ccc(-c2ccc(CNC(=O)n3sc4ncccc4c3=O)cc2)n1] | 3-Oxo-3H-isothiazolo[5,4-b]pyridine-2-carboxylic acid 4-(1-methyl-1H-pyrazol-3-yl)-benzylamide<br>C18H15N5O2S 365.417 |
| 28 | 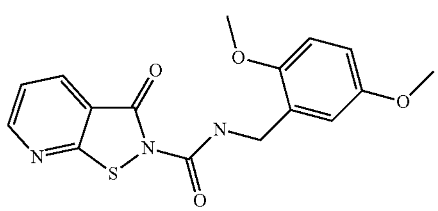 [SMILES: COc1ccc(OC)c(CNC(=O)n2sc3ncccc3c2=O)c1] | 3-Oxo-3H-isothiazolo[5,4-b]pyridine-2-carboxylic acid 2,5-dimethoxy-benzylamide<br>C16H15N3O4S 345.38 |
| 29 | 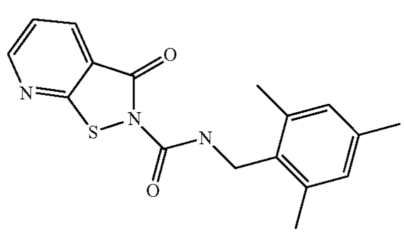 [SMILES: Cc1cc(C)c(CNC(=O)n2sc3ncccc3c2=O)c(C)c1] | 3-Oxo-3H-isothiazolo[5,4-b]pyridine-2-carboxylic acid 2,4,6-trimethyl-benzylamide<br>C17H17N3O2S 327.408 |
| 30 | 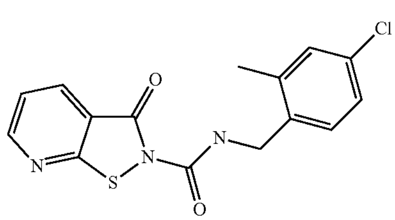 [SMILES: Cc1cc(Cl)ccc1CNC(=O)n1sc2ncccc2c1=O] | 3-Oxo-3H-isothiazolo[5,4-b]pyridine-2-carboxylic acid 4-chloro-2-methyl-benzylamide<br>C15H12ClN3O2 333.799 |

-continued

| Example No. | Structure | Name / Empirical formula / Molar mass [g/mol] |
|---|---|---|
| 31 | 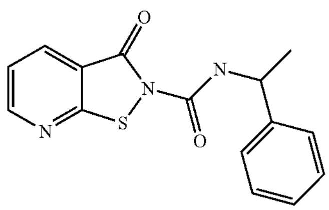 [SMILES: CC(NC(=O)n1sc2ncccc2c1=O)c1ccccc1] | 3-Oxo-3H-isothiazolo[5,4-b]pyridine-2-carboxylic acid (1-phenyl-ethyl)-amide<br>C15H13N3O2S 299.354 |
| 32 | 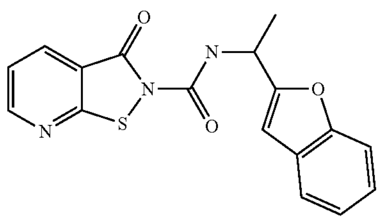 [SMILES: CC(NC(=O)n1sc2ncccc2c1=O)c1cc2ccccc2o1] | 3-Oxo-3H-isothiazolo[5,4-b]pyridine-2-carboxylic acid (1-benzofuran-2-yl-ethyl)-amide<br>C17H13N3O3S 339.375 |
| 33 | 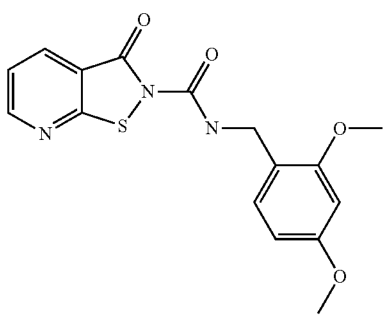 [SMILES: COc1ccc(CNC(=O)n2sc3ncccc3c2=O)c(OC)c1] | 3-Oxo-3H-isothiazolo[5,4-b]pyridine-2-carboxylic acid 2,4-dimethoxy-benzylamide<br>C16H15N3O4S 345.38 |
| 34 | 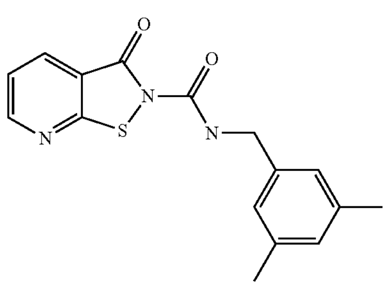 [SMILES: Cc1cc(C)cc(CNC(=O)n2sc3ncccc3c2=O)c1] | 3-Oxo-3H-isothiazolo[5,4-b]pyridine-2-carboxylic acid 3,5-dimethyl-benzylamide<br>C16H15N3O2S 313.381 |
| 35 | 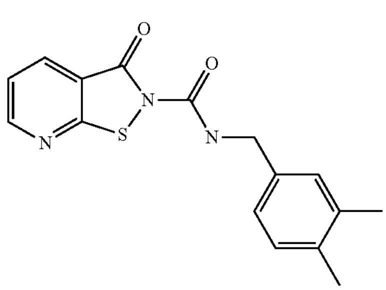 [SMILES: Cc1ccc(CNC(=O)n2sc3ncccc3c2=O)cc1C] | 3-Oxo-3H-isothiazolo[5,4-b]pyridine-2-carboxylic acid 3,4-dimethyl-benzylamide<br>C16H15N3O2S 313.381 |

| Example No. | Structure | Name<br>Empirical formula<br>Molar mass [g/mol] |
|---|---|---|
| 36 | 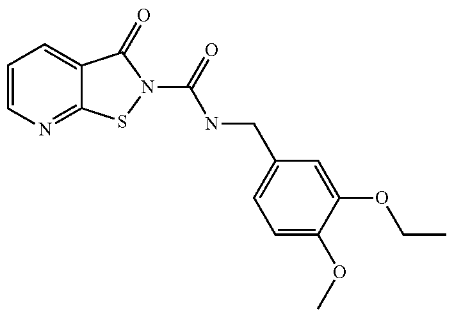 [SMILES: CCOc1cc(CNC(=O)n2sc3ncccc3c2=O)ccc1OC] | 3-Oxo-3H-isothiazolo[5,4-b]pyridine-2-carboxylic acid 3-ethoxy-4-methoxy-benzylamide<br>C17H17N3O4S 359.407 |
| 37 | 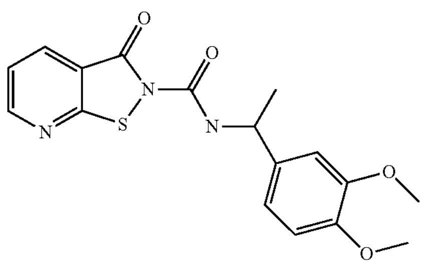 [SMILES: COc1ccc(C(C)NC(=O)n2sc3ncccc3c2=O)cc1OC] | 3-Oxo-3H-isothiazolo[5,4-b]pyridine-2-carboxylic acid [1-(3,4-dimethoxyphenyl)-ethyl]-amide<br>C17H17N3O4S 359.407 |
| 38 | 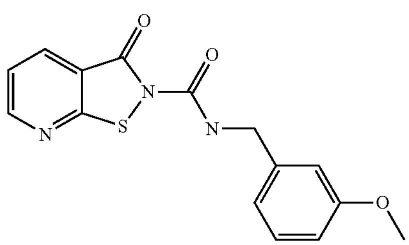 | 3-Oxo-3H-isothiazolo[5,4-b]pyridine-2-carboxylic acid 3-methoxy-benzylamide<br>C15H13N3O3S 315.353 |
| 39 | 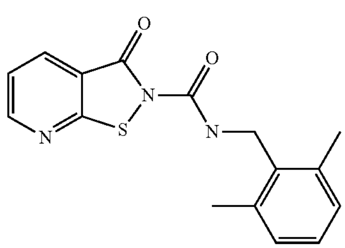 [SMILES: Cc1cccc(C)c1CNC(=O)n1sc2ncccc2c1=O] | 3-Oxo-3H-isothiazolo[5,4-b]pyridine-2-carboxylic acid 2,6-dimethyl-benzylamide<br>C16H15N3O2S 313.381 |
| 40 | 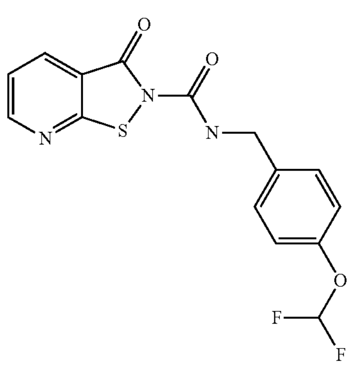 [SMILES: O=C(NCc1ccc(OC(F)F)cc1)n1sc2ncccc2c1=O] | 3-Oxo-3H-isothiazolo[5,4-b]pyridine-2-carboxylic acid 4-difluoromethoxy-benzylamide<br>C15H11F2N3O3 351.334 |

-continued

| Example No. | Structure | Name<br>Empirical formula<br>Molar mass [g/mol] |
|---|---|---|
| 41 | 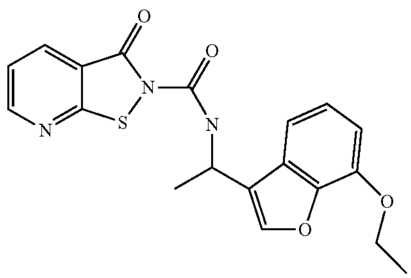 [SMILES: CCOc1cccc2c(C(C)NC(=O)n3sc4ncccc4c3=O)coc12] | 3-Oxo-3H-isothiazolo[5,4-b]pyridine-2-carboxylic acid [1-(7-ethoxy-benzofuran-3-yl)-ethyl]-amide<br>C19H17N3O4S 383.429 |
| 42 | 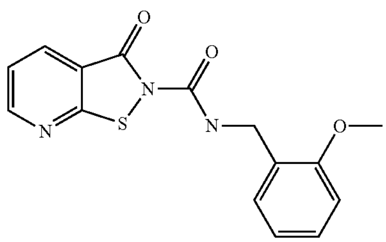 | 3-Oxo-3H-isothiazolo[5,4-b]pyridine-2-carboxylic acid 2-methoxy-benzyl-amide<br>C15H13N3O3S 315.353 |
| 43 | 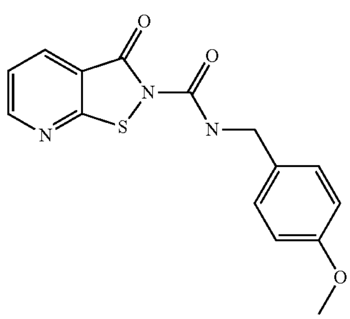 [SMILES: COc1ccc(CNC(=O)n2sc3ncccc3c2=O)cc1] | 3-Oxo-3H-isothiazolo[5,4-b]pyridine-2-carboxylic acid 4-methoxy-benzyl-amide<br>C15H13N3O3S 315.353 |
| 44 | 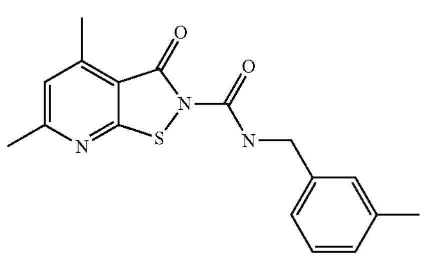 | 4,6-Dimethyl-3-oxo-3H-isothiazolo[5,4-b]pyridine-2-carboxylic acid 3-methyl-benzylamide<br>C17H17N3O2S 327.408 |
| 45 | 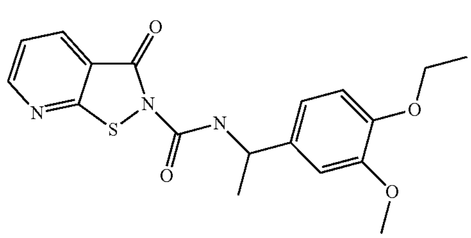 [SMILES: CCOc1ccc(C(C)NC(=O)n2sc3ncccc3c2=O)cc1OC] | 3-Oxo-3H-isothiazolo[5,4-b]pyridine-2-carboxylic acid [1-(4-ethoxy-3-methoxy-phenyl)-ethyl]-amide<br>C18H19N3O4S 373.434 |

-continued

| Example No. | Structure | Name<br>Empirical formula<br>Molar mass [g/mol] |
|---|---|---|
| 46 | 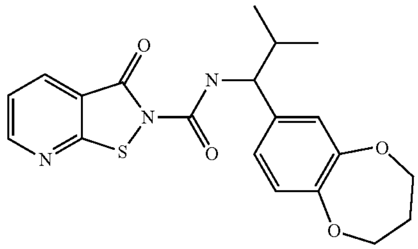 [SMILES: CC(C)C(NC(=O)n1sc2ncccc2c1=O)c1ccc2c(c1)OCCCO2] | 3-Oxo-3H-isothiazolo[5,4-b]pyridine-2-carboxylic acid [1-(3,4-dihydro-2H-benzo[b][1,4]dioxepin-7-yl)-2-methyl-propyl]-amide<br>C20H21N3O4S 399.472 |
| 47 | 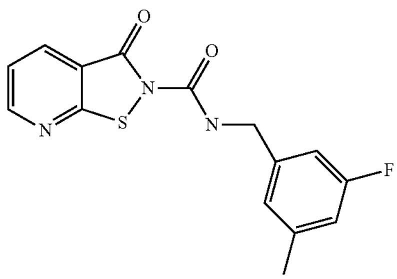 [SMILES: Cc1cc(F)cc(CNC(=O)n2sc3ncccc3c2=O)c1] | 3-Oxo-3H-isothiazolo[5,4-b]pyridine-2-carboxylic acid 3-fluoro-5-methyl-benzylamide<br>C15H12FN3O2S 317.344 |
| 48 | 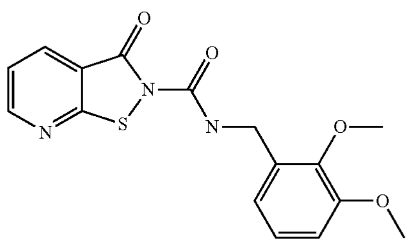 [SMILES: COc1cccc(CNC(=O)n2sc3ncccc3c2=O)c1OC] | 3-Oxo-3H-isothiazolo[5,4-b]pyridine-2-carboxylic acid 2,3-dimethoxy-benzylamide<br>C16H15N3O4S 345.38 |
| 49 | 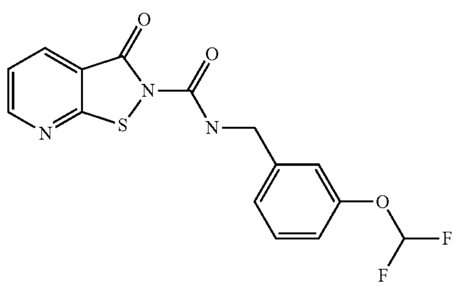 [SMILES: O=C(NCc1cccc(OC(F)F)c1)n1sc2ncccc2c1=O] | 3-Oxo-3H-isothiazolo[5,4-b]pyridine-2-carboxylic acid 3-difluoromethoxy-benzylamide<br>C15H11F2N3O3 351.334 |
| 50 | 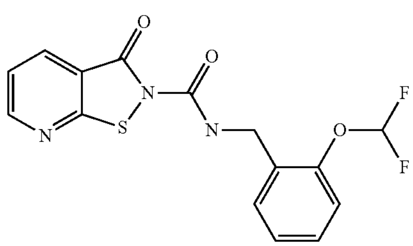 [SMILES: O=C(NCc1ccccc1OC(F)F)n1sc2ncccc2c1=O] | 3-Oxo-3H-isothiazolo[5,4-b]pyridine-2-carboxylic acid 2-difluoromethoxy-benzylamide<br>C15H11F2N3O3 351.334 |
| 51 | 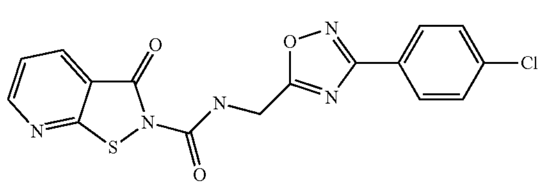 [SMILES: O=C(NCc1nc(-c2ccc(Cl)cc2)no1)n1sc2ncccc2c1=O] | 3-Oxo-3H-isothiazolo[5,4-b]pyridine-2-carboxylic acid [3-(4-chloro-phenyl)-[1,2,4]oxadiazol-5-ylmethyl]-amide<br>C16H10ClN5O3S 387.807 |

-continued

| Example No. | Structure | Name<br>Empirical formula<br>Molar mass [g/mol] |
|---|---|---|
| 52 | 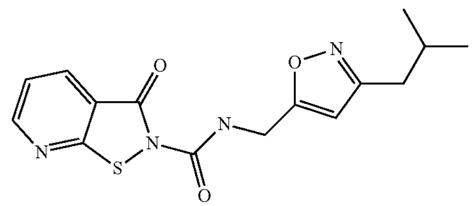 [SMILES: CC(C)Cc1cc(CNC(=O)n2sc3ncccc3c2=O)on1] | 3-Oxo-3H-isothiazolo[5,4-b]pyridine-2-carboxylic acid (3-isobutyl-isoxazol-5-ylmethyl)-amide<br>C15H16N4O3S 332.384 |
| 53 | 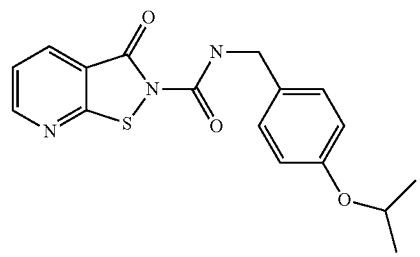 [SMILES: CC(C)Oc1ccc(CNC(=O)n2sc3ncccc3c2=O)cc1] | 3-Oxo-3H-isothiazolo[5,4-b]pyridine-2-carboxylic acid 4-isopropoxybenzylamide<br>C17H17N3O3S 343.407 |
| 54 | 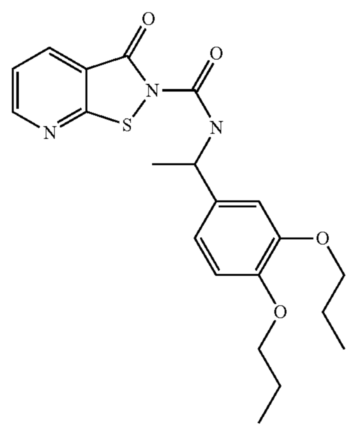 [SMILES: CCCOc1ccc(C(C)NC(=O)n2sc3ncccc3c2=O)cc1OCCC] | 3-Oxo-3H-isothiazolo[5,4-b]pyridine-2-carboxylic acid [1-(3,4-dipropoxyphenyl)-ethyl]-amide<br>C21H25N3O4S 415.515 |
| 55 | 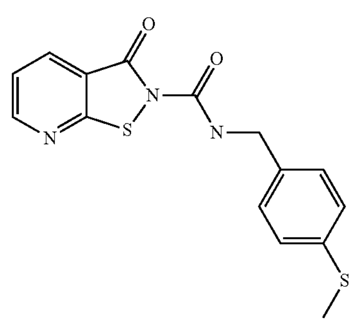 [SMILES: CSc1ccc(CNC(=O)n2sc3ncccc3c2=O)cc1] | 3-Oxo-3H-isothiazolo[5,4-b]pyridine-2-carboxylic acid 4-methylsulfanylbenzylamide<br>C15H13N3O2S2 331.418 |
| 56 | 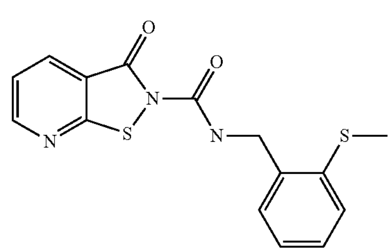 [SMILES: CSc1ccccc1CNC(=O)n1sc2ncccc2c1=O] | 3-Oxo-3H-isothiazolo[5,4-b]pyridine-2-carboxylic acid 2-methylsulfanylbenzylamide<br>C15H13N3O2S2 331.418 |

-continued

| Example No. | Structure | Name<br>Empirical formula<br>Molar mass [g/mol] |
|---|---|---|
| 57 | 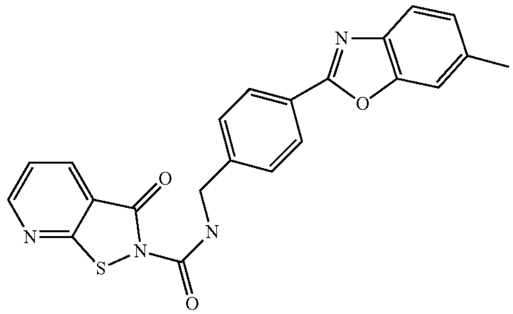 [SMILES: Cc1ccc2nc(-c3ccc(CNC(=O)n4sc5ncccc5c4=O)cc3)oc2c1] | 3-Oxo-3H-isothiazolo[5,4-b]pyridine-2-carboxylic acid 4-(6-methyl-benzo-oxazol-2-yl)-benzylamide<br>C22H16N4O3S 416.462 |
| 58 | 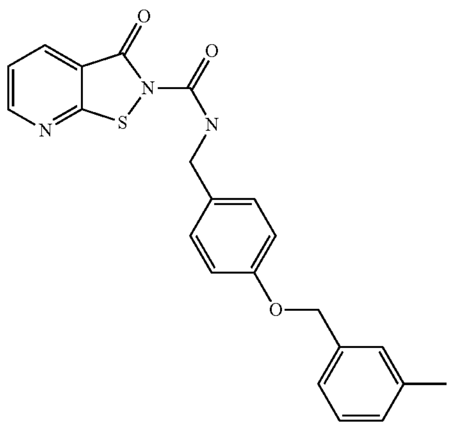 [SMILES: Cc1cccc(COc2ccc(CNC(=O)n3sc4ncccc4c3=O)cc2)c1] | 3-Oxo-3H-isothiazolo[5,4-b]pyridine-2-carboxylic acid 4-(3-methyl-benzyloxy)-benzylamide<br>C22H19N3O3S 405.479 |
| 59 | 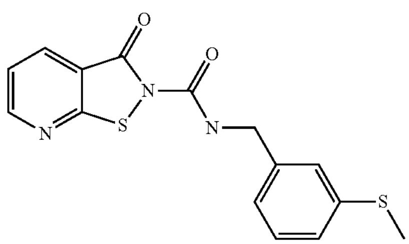 [SMILES: CSc1cccc(CNC(=O)n2sc3ncccc3c2=O)c1] | 3-Oxo-3H-isothiazolo[5,4-b]pyridine-2-carboxylic acid 3-methylsulfanyl-benzylamide<br>C15H13N3O2S2 331.418 |
| 60 | 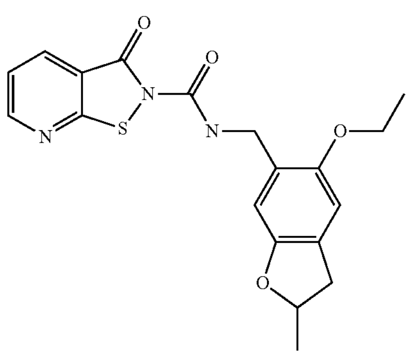 [SMILES: CCOc1cc2c(cc1CNC(=O)n1sc3ncccc3c1=O)OC(C)C2] | 3-Oxo-3H-isothiazolo[5,4-b]pyridine-2-carboxylic acid (5-ethoxy-2-methyl-2,3-dihydro-benzofuran-6-ylmethyl)-amide<br>C19H19N3O4S 385.445 |
| 61 | 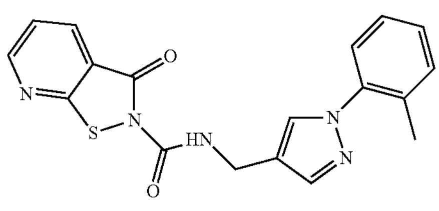 [SMILES: Cc1ccccc1-n1cc(CNC(=O)n2sc3ncccc3c2=O)cn1] | 3-Oxo-3H-isothiazolo[5,4-b]pyridine-2-carboxylic acid (1-o-tolyl-1H-pyrazol-4-ylmethyl)-amide<br>C18H15N5O2S 365.417 |

-continued

| Example No. | Structure | Name<br>Empirical formula<br>Molar mass [g/mol] |
|---|---|---|
| 62 | 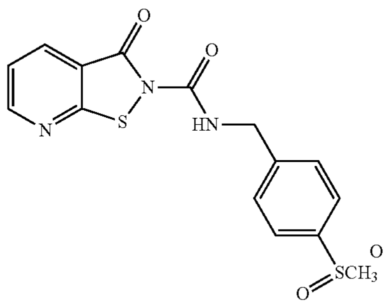 | 3-Oxo-3H-isothiazolo[5,4-b]pyridine-2-carboxylic acid 4-methanesulfonyl-benzylamide<br>C15H13N3O4S2 363.417 |
| 63 | 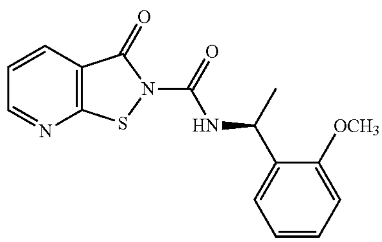 [SMILES: COc1ccccc1[C@H](C)NC(=O)n1sc2ncccc2c1=O] | 3-Oxo-3H-isothiazolo[5,4-b]pyridine-2-carboxylic acid [(S)-1-(2-methoxy-phenyl)-ethyl]-amide<br>C16H15N3O3S 329.38 |
| 64 | 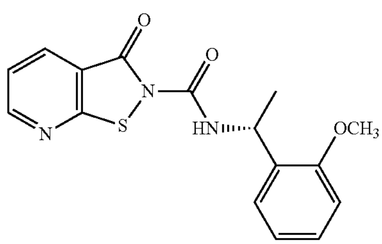 [SMILES: COc1ccccc1[C@@H](C)NC(=O)n1sc2ncccc2c1=O] | 3-Oxo-3H-isothiazolo[5,4-b]pyridine-2-carboxylic acid [(R)-1-(2-methoxy-phenyl)-ethyl]-amide<br>C16H15N3O3S 329.38 |
| 65 | 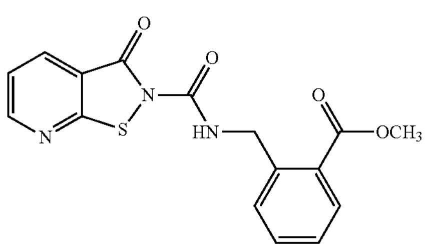 [SMILES: COC(=O)c1ccccc1CNC(=O)n1sc2ncccc2c1=O] | 2-{[(3-Oxo-3H-isothiazolo[5,4-b]pyridine-2-carbonyl)-amino]-methyl}-benzoic acid methyl ester<br>C16H13N3O4S 343.364 |
| 66 | 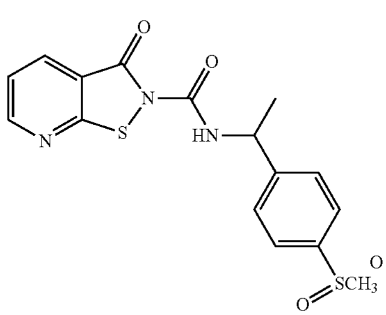 | 3-Oxo-3H-isothiazolo[5,4-b]pyridine-2-carboxylic acid [1-(4-methane-sulfonyl-phenyl)-ethyl]-amide<br>C16H15N3O4S2 377.444 |

-continued

| Example No. | Structure | Name<br>Empirical formula<br>Molar mass [g/mol] |
|---|---|---|
| 67 | 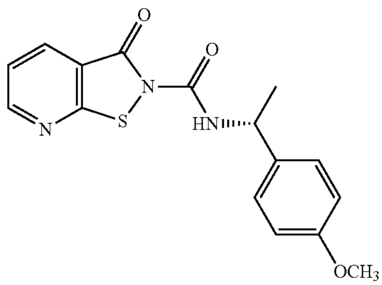 [SMILES: COc1ccc([C@@H](C)NC(=O)n2sc3ncccc3c2=O)cc1] | 3-Oxo-3H-isothiazolo[5,4-b]pyridine-2-carboxylic acid [(R)-1-(4-methoxy-phenyl)-ethyl]-amide<br>C16H15N3O3S 329.38 |
| 68 | 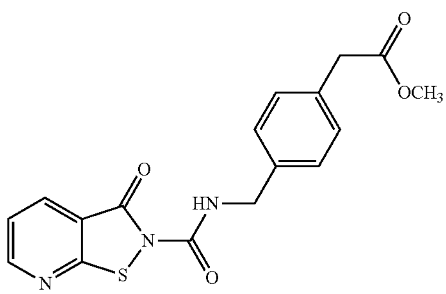 [SMILES: COC(=O)Cc1ccc(CNC(=O)n2sc3ncccc3c2=O)cc1] | (4-{[(3-Oxo-3H-isothiazolo[5,4-b]pyridine-2-carbonyl)-amino]-methyl}-phenyl)-acetic acid methyl ester<br>C17H15N3O4S 357.391 |
| 69 | 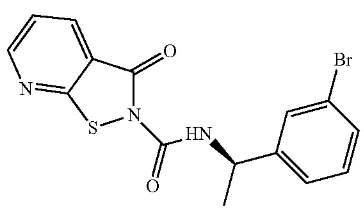 [SMILES: C[C@@H](NC(=O)n1sc2ncccc2c1=O)c1cccc(Br)c1] | 3-Oxo-3H-isothiazolo[5,4-b]pyridine-2-carboxylic acid [(R)-1-(3-bromo-phenyl)-ethyl]-amide<br>C15H12BrN3O2 378.25 |
| 70 | 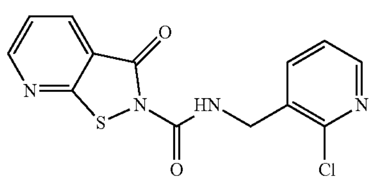 [SMILES: O=C(NCc1cccnc1Cl)n1sc2ncccc2c1=O] | 3-Oxo-3H-isothiazolo[5,4-b]pyridine-2-carboxylic acid (2-chloro-pyridin-3-ylmethyl)-amide<br>C13H9ClN4O2S 320.759 |
| 71 | 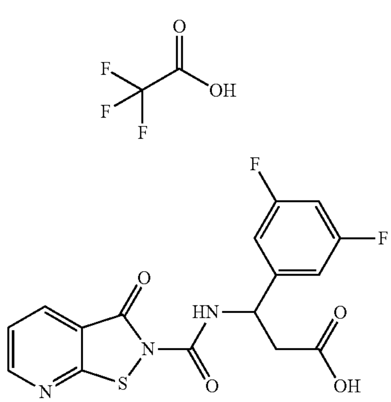 [SMILES: O=C(O)C(F)(F)F ; O=C(O)CC(NC(=O)n1sc2ncccc2c1=O)c1cc(F)cc(F)c1] | 3-(3,5-Difluoro-phenyl)-3-[(3-oxo-3H-isothiazolo[5,4-b]pyridine-2-carbonyl)-amino]-propionic acid; compound with trifluoro-acetic acid<br>C16H11F2N3O4S.<br>C2HF3O2 493.369 |

| Example No. | Structure | Name<br>Empirical formula<br>Molar mass [g/mol] |
|---|---|---|
| 72 | 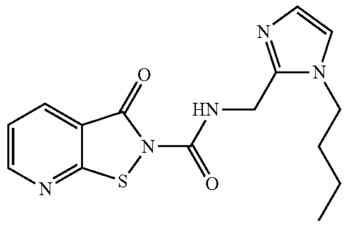 [SMILES: CCCCn1ccnc1CNC(=O)n1sc2ncccc2c1=O] | 3-Oxo-3H-isothiazolo[5,4-b]pyridine-2-carboxylic acid (1-butyl-1H-imidazol-2-ylmethyl)-amide<br>C15H17N5O2S 331.399 |
| 73 | 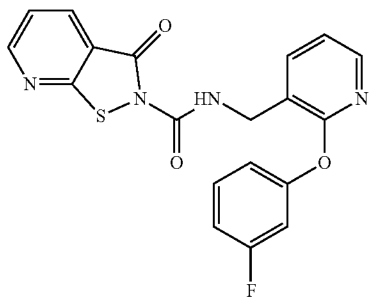 [SMILES: O=C(NCc1cccnc1Oc1cccc(F)c1)n1sc2ncccc2c1=O] | 3-Oxo-3H-isothiazolo[5,4-b]pyridine-2-carboxylic acid [2-(3-fluoro-phenoxy)-pyridin-3-ylmethyl]-amide<br>C19H13FN4O3S 396.403 |
| 74 | 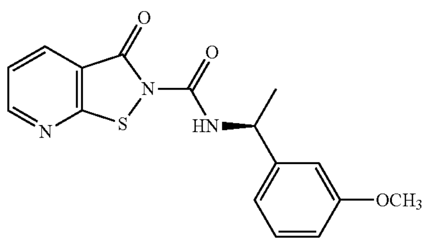 [SMILES: COc1cccc([C@H](C)NC(=O)n2sc3ncccc3c2=O)c1] | 3-Oxo-3H-isothiazolo[5,4-b]pyridine-2-carboxylic acid [(S)-1-(3-methoxyphenyl)-ethyl]-amide<br>C16H15N3O3S 329.38 |
| 75 | 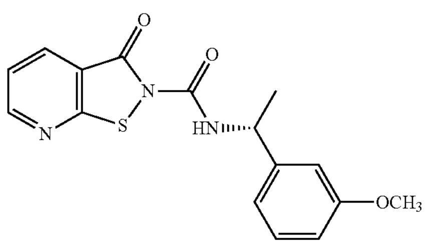 [SMILES: COc1cccc([C@@H](C)NC(=O)n2sc3ncccc3c2=O)c1] | 3-Oxo-3H-isothiazolo[5,4-b]pyridine-2-carboxylic acid [(R)-1-(3-methoxyphenyl)-ethyl]-amide<br>C16H15N3O3S 329.38 |
| 76 | 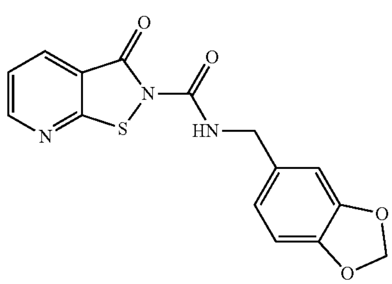 [SMILES: O=C(NCc1ccc2c(c1)OCO2)n1sc2ncccc2c1=O] | 3-Oxo-3H-isothiazolo[5,4-b]pyridine-2-carboxylic acid (benzo[1,3]dioxol-5-ylmethyl)-amide<br>C15H11N3O4S 329.337 |
| 77 | 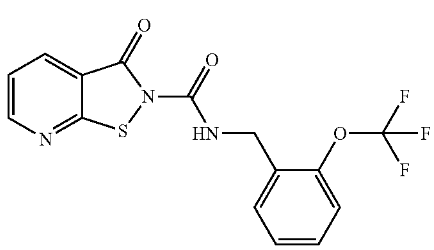 [SMILES: O=C(NCc1ccccc1OC(F)(F)F)n1sc2ncccc2c1=O] | 3-Oxo-3H-isothiazolo[5,4-b]pyridine-2-carboxylic acid 2-trifluoromethoxy-benzylamide<br>C15H10F3N3O3 369.324 |

-continued

| Example No. | Structure | Name / Empirical formula / Molar mass [g/mol] |
|---|---|---|
| 78 | 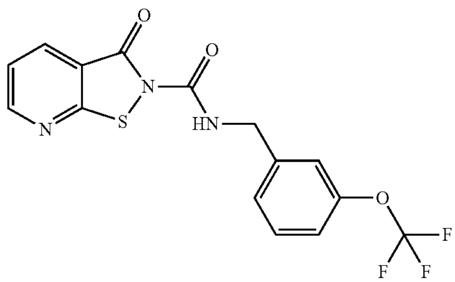 [SMILES: O=C(NCc1cccc(OC(F)(F)F)c1)n1sc2ncccc2c1=O] | 3-Oxo-3H-isothiazolo[5,4-b]pyridine-2-carboxylic acid 3-trifluoromethoxy-benzylamide<br>C15H10F3N3O3 369.324 |
| 79 | 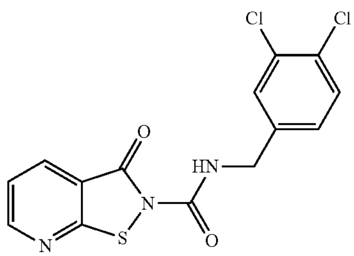 [SMILES: O=C(NCc1ccc(Cl)c(Cl)c1)n1sc2ncccc2c1=O] | 3-Oxo-3H-isothiazolo[5,4-b]pyridine-2-carboxylic acid 3,4-dichloro-benzylamide<br>C14H9Cl2N3O2 354.217 |
| 80 | 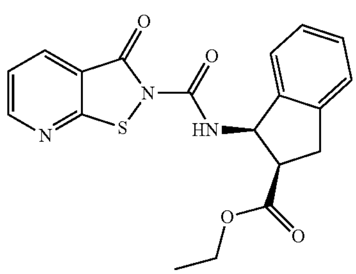 [SMILES: CCOC(=O)[C@@H]1Cc2ccccc2[C@@H]1NC(=O)n1sc2ncccc2c1=O] | (1R,2R)-1-[(3-Oxo-3H-isothiazolo[5,4-b]pyridine-2-carbonyl)-amino]-indan-2-carboxylic acid ethyl ester<br>C19H17N3O4S 383.429 |
| 81 | 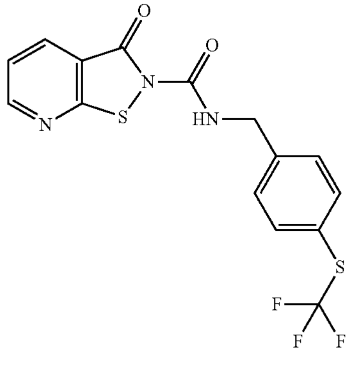 [SMILES: O=C(NCc1ccc(SC(F)(F)F)cc1)n1sc2ncccc2c1=O] | 3-Oxo-3H-isothiazolo[5,4-b]pyridine-2-carboxylic acid 4-trifluoromethyl-sulfanyl-benzylamide<br>C15H10F3N3O2S 385.389 |

-continued

| Example No. | Structure | Name<br>Empirical formula<br>Molar mass [g/mol] |
|---|---|---|
| 82 | 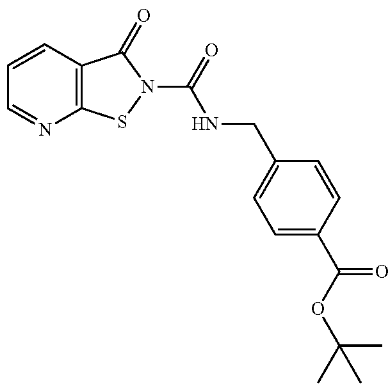 [SMILES: CC(C)(C)OC(=O)c1ccc(CNC(=O)n2sc3ncccc3c2=O)cc1] | 4-{[(3-Oxo-3H-isothiazolo[5,4-b]<br>pyridine-2-carbonyl)-amino]-methyl}-<br>benzoic acid tert-butyl ester<br>C19H19N3O4S 385.445 |
| 83 | 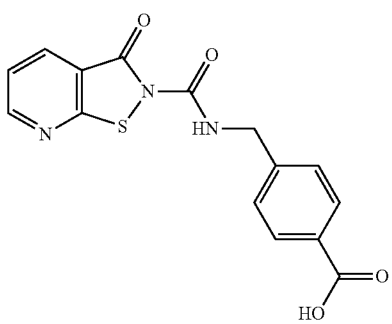 [SMILES: O=C(O)c1ccc(CNC(=O)n2sc3ncccc3c2=O)cc1] | 4-{[(3-Oxo-3H-isothiazolo[5,4-b]<br>pyridine-2-carbonyl)-amino]-methyl}-<br>benzoic acid<br>C15H11N3O4S 329.337 |
| 84 | 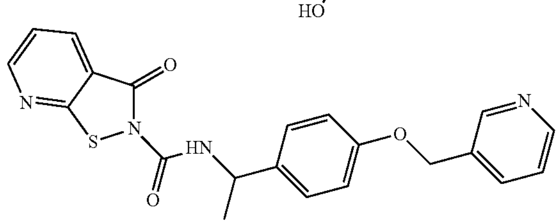 | 3-Oxo-3H-isothiazolo[5,4-b]pyridine-<br>2-carboxylic acid {1-[4-(pyridin-3-<br>ylmethoxy-phenyl]-ethyl}amide<br>C21H18N4O3S 406.467 |
| 85 | 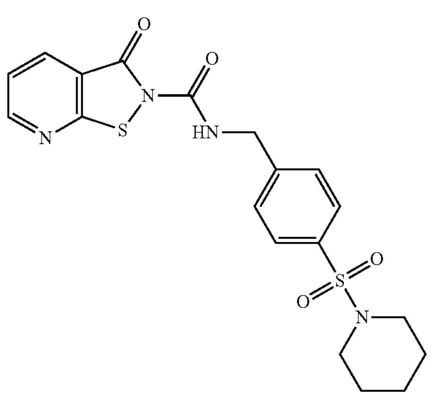 [SMILES: O=C(NCc1ccc(S(=O)(=O)N2CCCCC2)cc1)n1sc2ncccc2c1=O] | 3-Oxo-3H-isothiazolo[5,4-b]pyridine-<br>2-carboxylic acid 4-(piperidine-1-<br>sulfonyl)-benzylamide<br>C19H20N4O4S2 432.524 |
| 86 | 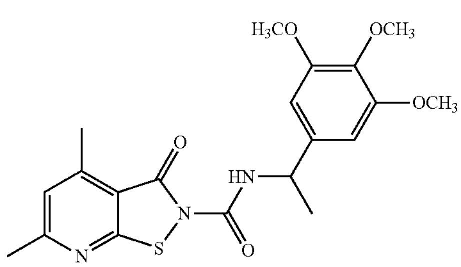 [SMILES: COc1cc(C(C)NC(=O)n2sc3nc(C)cc(C)c3c2=O)cc(OC)c1OC] | 4,6-Dimethyl-3-oxo-3H-isothiazolo[5,4-<br>b]pyridine-2-carboxylic acid [1-<br>(3,4,5-trimethoxy-phenyl)-ethyl]<br>amide<br>C20H23N3O5S 417.487 |

-continued

| Example No. | Structure | Name<br>Empirical formula<br>Molar mass [g/mol] |
|---|---|---|
| 87 | 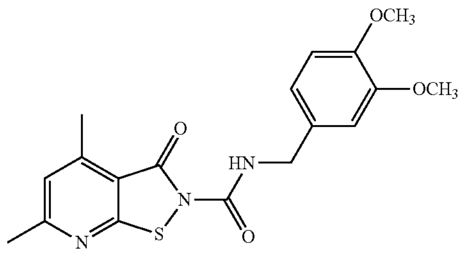 [SMILES: COc1ccc(CNC(=O)n2sc3nc(C)cc(C)c3c2=O)cc1OC] | 4,6-Dimethyl-3-oxo-3H-isothiazolo[5,4-b]pyridine-2-carboxylic acid 3,4-dimethoxy-benzylamide<br>C18H19N3O4S 373.434 |
| 88 | 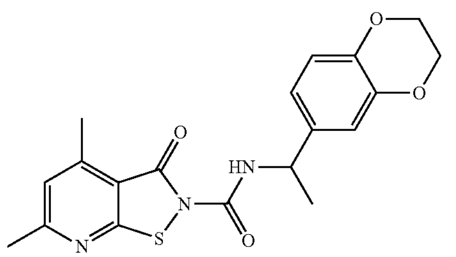 [SMILES: Cc1cc(C)c2c(=O)n(C(=O)NC(C)c3ccc4c(c3)OCCO4)sc2n1] | 4,6-Dimethyl-3-oxo-3H-isothiazolo[5,4-b]pyridine-2-carboxylic acid [1-(2,3-dihydro-benzo[1,4]dioxin-6-yl)-ethyl]-amide<br>C19H19N3O4S 385.445 |
| 89 | 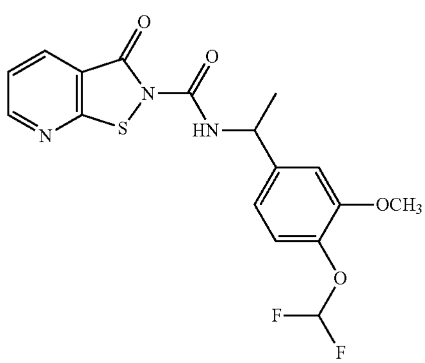 [SMILES: COc1cc(C(C)NC(=O)n2sc3ncccc3c2=O)ccc1OC(F)F] | 3-Oxo-3H-isothiazolo[5,4-b]pyridine-2-carboxylic acid [1-(4-difluoro-methoxy-3-methoxy-phenyl)-ethyl]-amide<br>C17H15F2N3O4 395.388 |
| 90 | 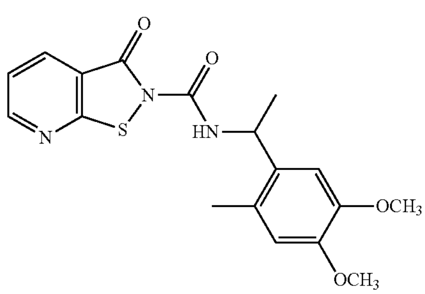 [SMILES: COc1cc(C)c(C(C)NC(=O)n2sc3ncccc3c2=O)cc1OC] | 3-Oxo-3H-isothiazolo[5,4-b]pyridine-2-carboxylic acid [1-(4,5-dimethoxy-2-methyl-phenyl)-ethyl]-amide<br>C18H19N3O4S 373.434 |
| 91 | 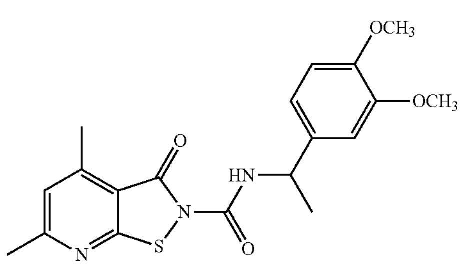 [SMILES: COc1ccc(C(C)NC(=O)n2sc3nc(C)cc(C)c3c2=O)cc1OC] | 4,6-Dimethyl-3-oxo-3H-isothiazolo[5,4-b]pyridine-2-carboxylic acid [1-(3,4-dimethoxy-phenyl)-ethyl]-amide<br>C19H21N3O4S 387.461 |

-continued

| Example No. | Structure | Name Empirical formula Molar mass [g/mol] |
|---|---|---|
| 92 | 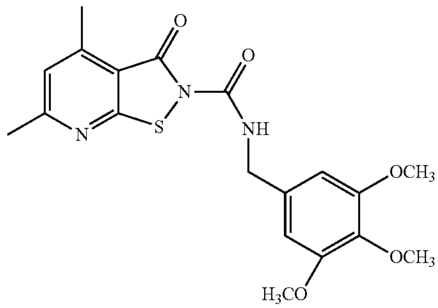 [SMILES: COc1cc(CNC(=O)n2sc3nc(C)cc(C)c3c2=O)cc(OC)c1OC] | 4,6-Dimethyl-3-oxo-3H-isothiazolo[5,4-b]pyridine-2-carboxylic acid 3,4,5-trimethoxy-benzylamide<br>C19H21N3O5S 403.46 |
| 93 | 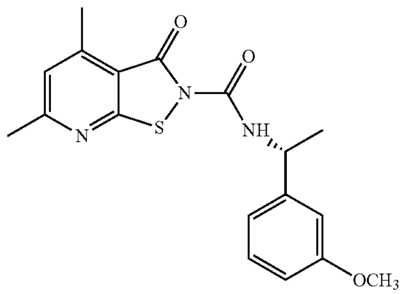 [SMILES: COc1cccc([C@@H](C)NC(=O)n2sc3nc(C)cc(C)c3c2=O)c1] | 4,6-Dimethyl-3-oxo-3H-isothiazolo[5,4-b]pyridine-2-carboxylic acid [(R)-1-(3-methoxy-phenyl)-ethyl]-amide<br>C18H19N3O3S 357.434 |
| 94 | 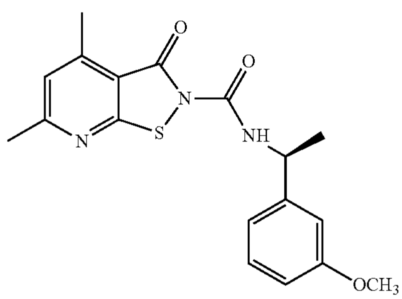 [SMILES: COc1cccc([C@H](C)NC(=O)n2sc3nc(C)cc(C)c3c2=O)c1] | 4,6-Dimethyl-3-oxo-3H-isothiazolo[5,4-b]pyridine-2-carboxylic acid [(S)-1-(3-methoxy-phenyl)-ethyl]-amide<br>C18H19N3O3S 357.434 |
| 95 | 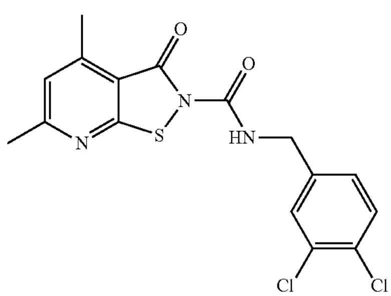 [SMILES: Cc1cc(C)c2c(=O)n(C(=O)NCc3ccc(Cl)c(Cl)c3)sc2n1] | 4,6-Dimethyl-3-oxo-3H-isothiazolo[5,4-b]pyridine-2-carboxylic acid 3,4-dichloro-benzylamide<br>C16H13Cl2N3O 382.271 |
| 96 | 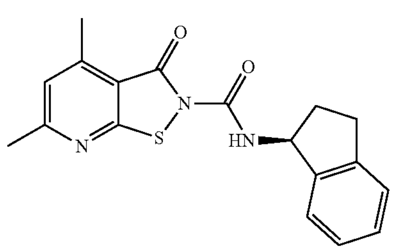 [SMILES: Cc1cc(C)c2c(=O)n(C(=O)N[C@H]3CCc4ccccc43)sc2n1] | 4,6-Dimethyl-3-oxo-3H-isothiazolo[5,4-b]pyridine-2-carboxylic acid (S)-indan-1-ylamide<br>C18H17N3O2S 339.419 |

-continued

| Example No. | Structure | Name / Empirical formula / Molar mass [g/mol] |
|---|---|---|
| 97 | 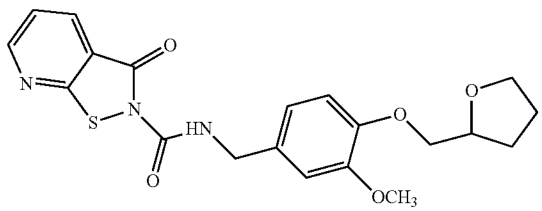 [SMILES: COc1cc(CNC(=O)n2sc3ncccc3c2=O)ccc1OCC1CCCO1] | 3-Oxo-3H-isothiazolo[5,4-b]pyridine-2-carboxylic acid 3-methoxy-4-(tetrahydro-furan-2-ylmethoxy)-benzylamide<br>C20H21N3O5S 415.471 |
| 98 | 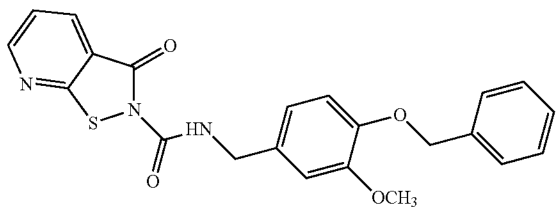 [SMILES: COc1cc(CNC(=O)n2sc3ncccc3c2=O)ccc1OCc1ccccc1] | 3-Oxo-3H-isothiazolo[5,4-b]pyridine-2-carboxylic acid 4-benzyloxy-3-methoxy-benzylamide<br>C22H19N3O4S 421.478 |
| 99 | 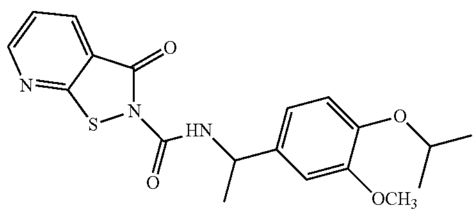 [SMILES: COc1cc(C(C)NC(=O)n2sc3ncccc3c2=O)ccc1OC(C)C] | 3-Oxo-3H-isothiazolo[5,4-b]pyridine-2-carboxylic acid [1-(4-isopropoxy-3-methoxy-phenyl)-ethyl]-amide<br>C19H21N3O4S 387.461 |
| 100 | 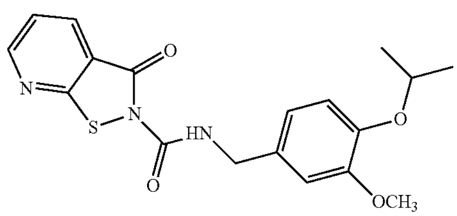 [SMILES: COc1cc(CNC(=O)n2sc3ncccc3c2=O)ccc1OC(C)C] | 3-Oxo-3H-isothiazolo[5,4-b]pyridine-2-carboxylic acid 4-isopropoxy-3-methoxy-benzylamide<br>C18H19N3O4S 373.434 |
| 101 | 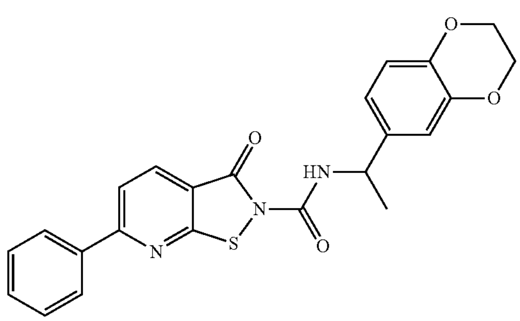 [SMILES: CC(NC(=O)n1sc2nc(-c3ccccc3)ccc2c1=O)c1ccc2c(c1)OCCO2] | 3-Oxo-6-phenyl-3H-isothiazolo[5,4-b]pyridine-2-carboxylic acid [1-(2,3-dihydro-benzo[1,4]dioxin-6-yl)-ethyl]-amide<br>C23H19N3O4S 433.49 |
| 102 | 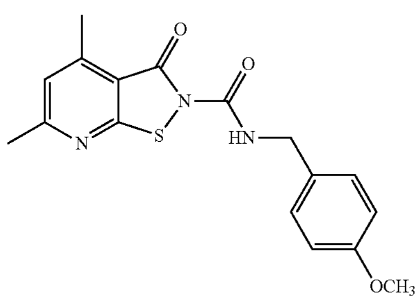 [SMILES: COc1ccc(CNC(=O)n2sc3nc(C)cc(C)c3c2=O)cc1] | 4,6-Dimethyl-3-oxo-3H-isothiazolo[5,4-b]pyridine-2-carboxylic acid 4-methoxy-benzylamide<br>C17H17N3O3S 343.407 |

| Example No. | Structure | Name / Empirical formula / Molar mass [g/mol] |
|---|---|---|
| 103 | | 3-Oxo-3H-isothiazolo[5,4-b]pyridine-2-carboxylic acid 4-(2-dimethylamino-ethoxy)-benzylamide; compound with trifluoro-acetic acid<br>C18H20N4O3S.<br>2C2HF3O2 600.498 |
| 104 | 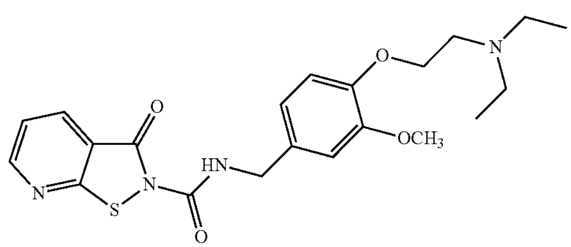 [SMILES: CCN(CC)CCOc1ccc(CNC(=O)n2sc3ncccc3c2=O)cc1OC] | 3-Oxo-3H-isothiazolo[5,4-b]pyridine-2-carboxylic acid 4-(2-diethylamino-ethoxy)-3-methoxy-benzylamide<br>C21H26N4O4S 430.53 |
| 105 | | (2-Methoxy-4-{1-[(3-oxo-3H-isothiazolo[5,4-b]pyridine-2-carbonyl)-amino]-ethyl}-phenoxy)-acetic acid; compound with trifluoro-acetic acid<br>C18H17N3O6S.<br>C2HF3O2 517.441 |
| 106 | 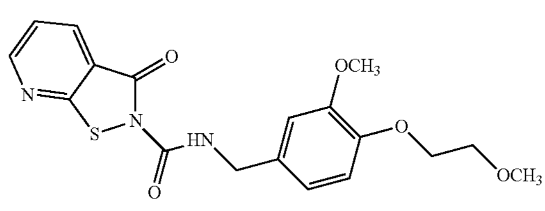 [SMILES: COCCOc1ccc(CNC(=O)n2sc3ncccc3c2=O)cc1OC] | 3-Oxo-3H-isothiazolo[5,4-b]pyridine-2-carboxylic acid 3-methoxy-4-(2-methoxy-ethoxy)-benzylamide<br>C18H19N3O5S 389.433 |
| 107 | 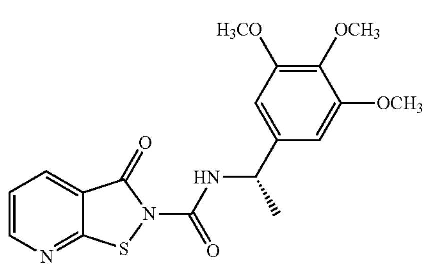 [SMILES: COc1cc([C@H](C)NC(=O)n2sc3ncccc3c2=O)cc(OC)c1OC] | 3-Oxo-3H-isothiazolo[5,4-b]pyridine-2-carboxylic acid [(S)-1-(3,4,5-trimethoxy-phenyl)-ethyl]-amide<br>C18H19N3O5S 389.433 |

-continued

| Example No. | Structure | Name<br>Empirical formula<br>Molar mass [g/mol] |
|---|---|---|
| 108 | 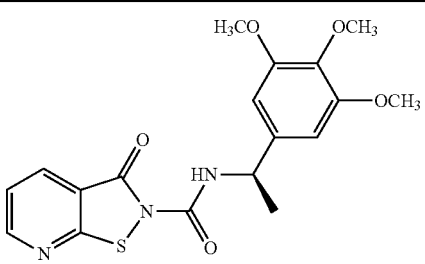 | 3-Oxo-3H-isothiazolo[5,4-b]pyridine-2-carboxylic acid [(R)-1-(3,4,5-trimethoxy-phenyl)-ethyl]amide<br>C18H19N3O5S 389.433 |
| 109 | 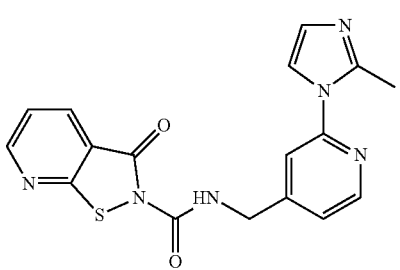 [SMILES: Cc1nccn1-c1cc(CNC(=O)n2sc3ncccc3c2=O)ccn1] | 3-Oxo-3H-isothiazolo[5,4-b]pyridine-2-carboxylic acid [2-(2-methyl-imidazol-1-yl)-pyridin-4-ylmethyl]-amide<br>C17H14N6O2S 366.404 |
| 110 | 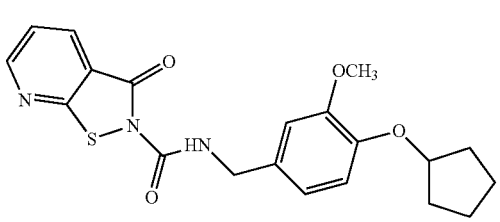 [SMILES: COc1cc(CNC(=O)n2sc3ncccc3c2=O)ccc1OC1CCCC1] | 3-Oxo-3H-isothiazolo[5,4-b]pyridine-2-carboxylic acid 4-cyclopentyloxy-3-methoxy-benzylamide<br>C20H21N3O4S 399.472 |
| 111 | 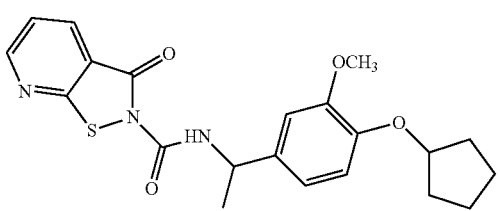 [SMILES: COc1cc(C(C)NC(=O)n2sc3ncccc3c2=O)ccc1OC1CCCC1] | 3-Oxo-3H-isothiazolo[5,4-b]pyridine-2-carboxylic acid [1-(4-cyclopentyloxy-3-methoxy-phenyl)-ethyl]-amide<br>C21H23N3O4S 413.499 |
| 112 | 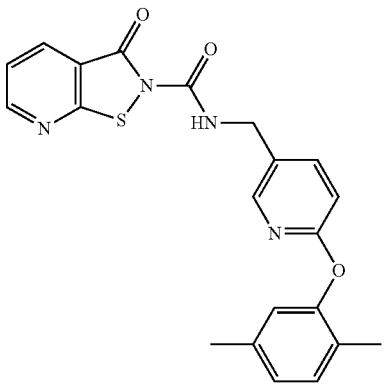 [SMILES: Cc1ccc(C)c(Oc2ccc(CNC(=O)n3sc4ncccc4c3=O)cn2)c1] | 3-Oxo-3H-isothiazolo[5,4-b]pyridine-2-carboxylic acid [6-(2,5-dimethyl-phenoxy)-pyridin-3-ylmethyl]-amide<br>C21H18N4O3S 406.467 |

-continued

| Example No. | Structure | Name<br>Empirical formula<br>Molar mass [g/mol] |
|---|---|---|
| 113 | 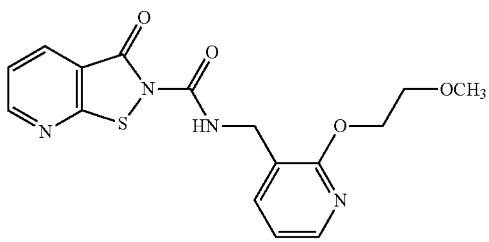 [SMILES: COCCOc1ncccc1CNC(=O)n1sc2ncccc2c1=O] | 3-Oxo-3H-isothiazolo[5,4-b]pyridine-2-carboxylic acid [2-(2-methoxy-ethoxy)-pyridin-3-ylmethyl]-amide<br>C16H16N4O4S 360.394 |
| 114 | 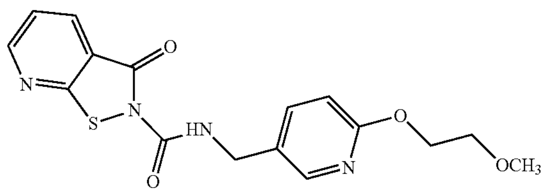 [SMILES: COCCOc1ccc(CNC(=O)n2sc3ncccc3c2=O)cn1] | 3-Oxo-3H-isothiazolo[5,4-b]pyridine-2-carboxylic acid [6-(2-methoxy-ethoxy)-pyridin-3-ylmethyl]-amide<br>C16H16N4O4S 360.394 |
| 115 | 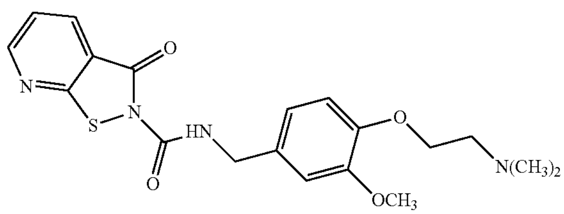 [SMILES: COc1cc(CNC(=O)n2sc3ncccc3c2=O)ccc1OCCN(C)C] | 3-Oxo-3H-isothiazolo[5,4-b]pyridine-2-carboxylic acid 4-(2-dimethylamino-ethoxy)-3-methoxy-benzylamide<br>C19H22N4O4S 402.476 |
| 116 | 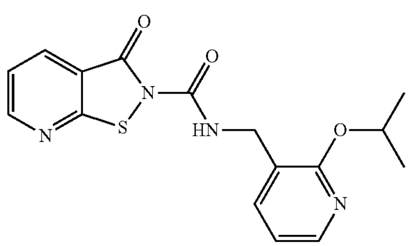 [SMILES: CC(C)Oc1ncccc1CNC(=O)n1sc2ncccc2c1=O] | 3-Oxo-3H-isothiazolo[5,4-b]pyridine-2-carboxylic acid (2-isopropoxy-pyridin-3-ylmethyl)-amide<br>C16H16N4O3S 344.395 |
| 117 | 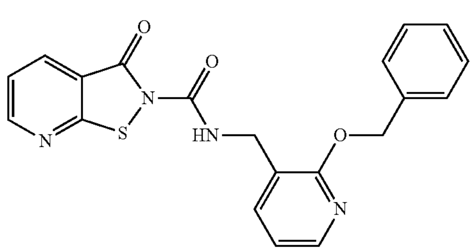 [SMILES: O=C(NCc1cccnc1OCc1ccccc1)n1sc2ncccc2c1=O] | 3-Oxo-3H-isothiazolo[5,4-b]pyridine-2-carboxylic acid (2-benzyloxy-pyridin-3-ylmethyl)-amide<br>C20H16N4O3S 392.44 |
| 118 | 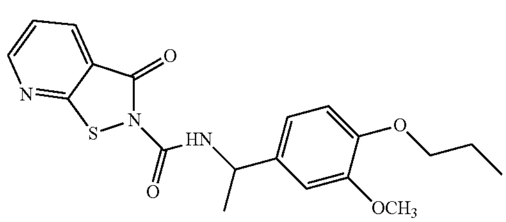 [SMILES: CCCOc1ccc(C(C)NC(=O)n2sc3ncccc3c2=O)cc1OC] | 3-Oxo-3H-isothiazolo[5,4-b]pyridine-2-carboxylic acid [1-(3-methoxy-4-propoxy-phenyl)-ethyl]-amide<br>C19H21N3O4S 387.461 |

| Example No. | Structure | Name<br>Empirical formula<br>Molar mass [g/mol] |
|---|---|---|
| 119 | 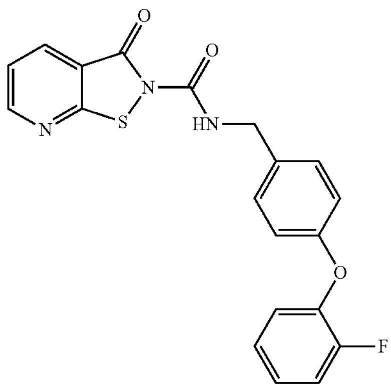 [SMILES: O=C(NCc1ccc(Oc2ccccc2F)cc1)n1sc2ncccc2c1=O] | 3-Oxo-3H-isothiazolo[5,4-b]pyridine-2-carboxylic acid 4-(2-fluoro-phenoxy)-benzylamide<br>C20H14FN3O3S 395.415 |
| 120 | 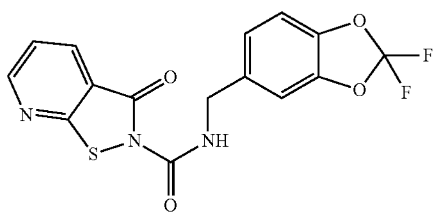 [SMILES: O=C(NCc1ccc2c(c1)OC(F)(F)O2)n1sc2ncccc2c1=O] | 3-Oxo-3H-isothiazolo[5,4-b]pyridine-2-carboxylic acid (2,2-difluoro-benzo[1,3]dioxol-5-ylmethyl)-amide<br>C15H9F2N3O4S 365.317 |
| 121 | HCl | 3-Oxo-3H-isothiazolo[5,4-b]pyridine-2-carboxylic acid 3-methoxy-4-(pyridin-4-ylmethoxy)-benzylamide<br>C21H18N4O4S 458.927 |
| 122 | 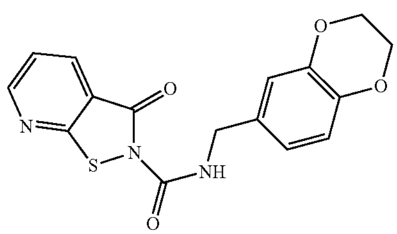 [SMILES: O=C(NCc1ccc2c(c1)OCCO2)n1sc2ncccc2c1=O] | 3-Oxo-3H-isothiazolo[5,4-b]pyridine-2-carboxylic acid (2,3-dihydro-benzo[1,4]dioxin-6-ylmethyl)-amide<br>C16H13N3O4S 343.364 |
| 123 | 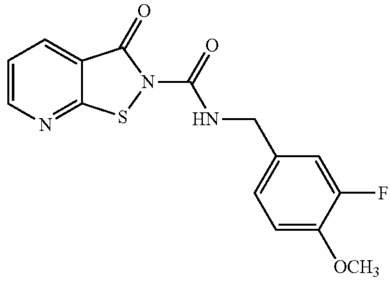 [SMILES: COc1ccc(CNC(=O)n2sc3ncccc3c2=O)cc1F] | 3-Oxo-3H-isothiazolo[5,4-b]pyridine-2-carboxylic acid 3-fluoro-4-methoxy-benzylamide<br>C15H12FN3O3S 333.344 |

-continued

| Example No. | Structure | Name
Empirical formula
Molar mass [g/mol] |
|---|---|---|
| 124 | | 3-Oxo-3H-isothiazolo[5,4-b]pyridine-2-carboxylic acid 4-(2-morpholin-4-yl-ethoxy)-benzylamide
C20H22N4O4S 414.487 |
| 125 | | 3-Oxo-3H-isothiazolo[5,4-b]pyridine-2-carboxylic acid (1-imidazo[2,1-b]thiazol-6-yl-ethyl)-amide
C14H11N5O2S2 345.404 |
| 126 | | 3-Oxo-3H-isothiazolo[5,4-b]pyridine-2-carboxylic acid 4-(4-methyl-piperazin-1-yl)-benzylamide
C19H21N5O2S
383.476 |
| 127 | | 3-Oxo-3H-isothiazolo[5,4-b]pyridine-2-carboxylic acid (3-methyl-3H-imidazol-4-ylmethyl)-amide
C12H11N5O2S
289.318 |
| 128 | | 3-Oxo-3H-isothiazolo[5,4-b]pyridine-2-carboxylic acid {1-[3-methoxy-4-(2-methoxy-ethoxy)-phenyl]ethyl}-amide
C19H21N3O5S
403.46 |
| 129 | | 3-Oxo-3H-isothiazolo[5,4-b]pyridine-2-carboxylic acid 4-ethoxy-3-methoxy-benzylamide
C17H17N3O4S
359.407 |
| 130 | | 3-Oxo-3H-isothiazolo[5,4-b]pyridine-2-carboxylic acid 4-dimethylamino-methyl-benzylamide
C17H18N4O2S
342.423 |

-continued

| Example No. | Structure | Name / Empirical formula / Molar mass [g/mol] |
|---|---|---|
| 131 | 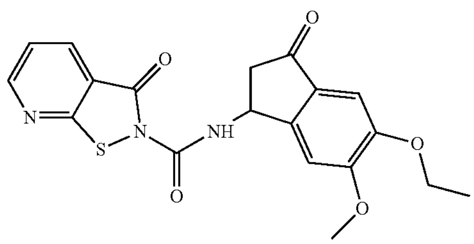 [SMILES: CCOc1cc2c(cc1OC)C(NC(=O)n1sc3ncccc3c1=O)CC2=O] | 3-Oxo-3H-isothiazolo[5,4-b]pyridine-2-carboxylic acid (5-ethoxy-6-methoxy-3-oxo-indan-1-yl)-amide<br>C19H17N3O5S 399.42 |
| 132 | 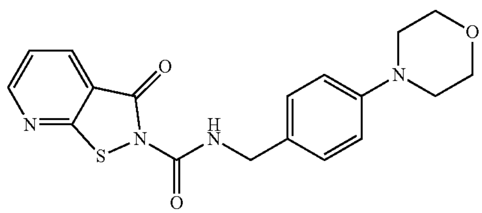 [SMILES: O=C(NCc1ccc(N2CCOCC2)cc1)n1sc2ncccc2c1=O] | 3-Oxo-3H-isothiazolo[5,4-b]pyridine-2-carboxylic acid 4-morpholin-4-yl-benzylamide<br>C18H18N4O3S<br>370.433 |
| 133 | 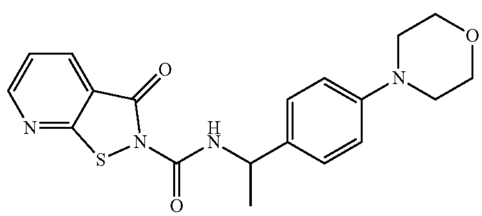 [SMILES: CC(NC(=O)n1sc2ncccc2c1=O)c1ccc(N2CCOCC2)cc1] | 3-Oxo-3H-isothiazolo[5,4-b]pyridine-2-carboxylic acid [1-(4-morpholin-4-yl-phenyl)-ethyl]-amide<br>C19H20N4O3S<br>384.46 |
| 134 | 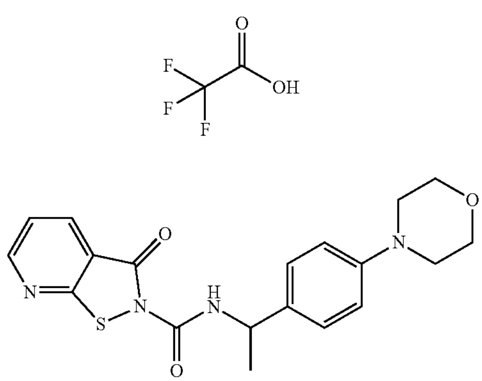 [SMILES: O=C(O)C(F)(F)F ; CC(NC(=O)n1sc2ncccc2c1=O)c1ccc(N2CCOCC2)cc1] | 3-Oxo-3H-isothiazolo[5,4-b]pyridine-2-carboxylic acid [1-(4-morpholin-4-yl-phenyl)-ethyl]-amide<br>C19H20N4O3S•2C2HF3O2<br>612.509 |
| 135 | 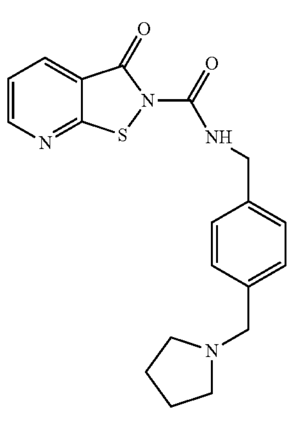 [SMILES: O=C(NCc1ccc(CN2CCCC2)cc1)n1sc2ncccc2c1=O] | 3-Oxo-3H-isothiazolo[5,4-b]pyridine-2-carboxylic acid 4-pyrrolidin-1-ylmethyl-benzylamide<br>C19H20N4O2S<br>368.461 |

| Example No. | Structure | Name<br>Empirical formula<br>Molar mass [g/mol] |
|---|---|---|
| 136 | 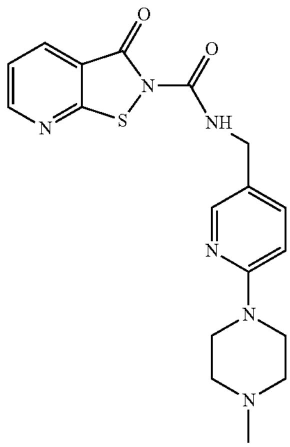 [SMILES: CN1CCN(c2ccc(CNC(=O)n3sc4ncccc4c3=O)cn2)CC1] | 3-Oxo-3H-isothiazolo[5,4-b]pyridine-2-carboxylic acid [6-(4-methyl-piperazin-1-yl)-pyridin-3-ylmethyl]-amide<br>C18H20N6O2S<br>384.463 |
| 137 | 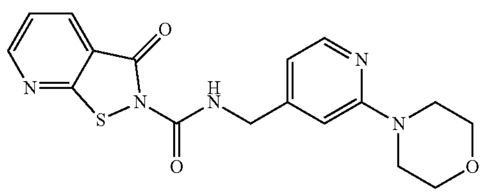 [SMILES: O=C(NCc1ccnc(N2CCOCC2)c1)n1sc2ncccc2c1=O] | 3-Oxo-3H-isothiazolo[5,4-b]pyridine-2-carboxylic acid (2-morpholin-4-yl-pyridin-4-ylmethyl)-amide<br>C17H17N5O3S<br>371.421 |
| 138 | 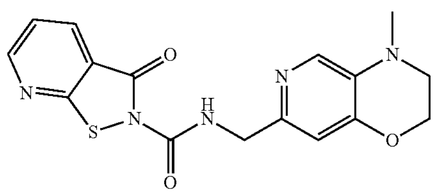 [SMILES: CN1CCOc2cc(CNC(=O)n3sc4ncccc4c3=O)ncc21] | 3-Oxo-3H-isothiazolo[5,4-b]pyridine-2-carboxylic acid (4-methyl-3,4-di-hydro-2H-pyrido[4,3-b][1,4]oxazin-7-ylmethyl)-amide<br>C16H15N5O3S<br>357.394 |
| 139 | 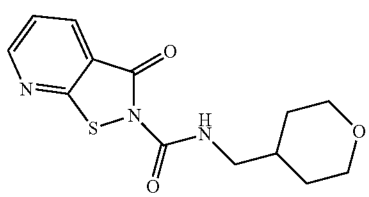 [SMILES: O=C(NCC1CCOCC1)n1sc2ncccc2c1=O] | 3-Oxo-3H-isothiazolo[5,4-b]pyridine-2-carboxylic acid (tetrahydro-pyran-4-ylmethyl)-amide<br>C13H15N3O3S 293.347 |
| 140 | 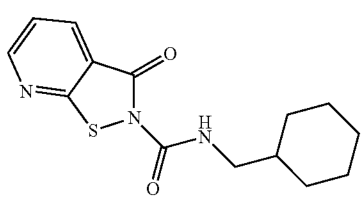 [SMILES: O=C(NCC1CCCCC1)n1sc2ncccc2c1=O] | 3-Oxo-3H-isothiazolo[5,4-b]pyridine-2-carboxylic acid cyclohexylmethyl-amide<br>C14H17N3O2S 291.374 |
| 141 | 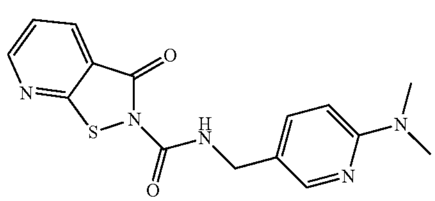 [SMILES: CN(C)c1ccc(CNC(=O)n2sc3ncccc3c2=O)cn1] | 3-Oxo-3H-isothiazolo[5,4-b]pyridine-2-carboxylic acid (6-dimethylamino-pyridin-3-ylmethyl)-amide<br>C15H15N5O2S 329.383 |

-continued

| Example No. | Structure | Name<br>Empirical formula<br>Molar mass [g/mol] |
|---|---|---|
| 142 | 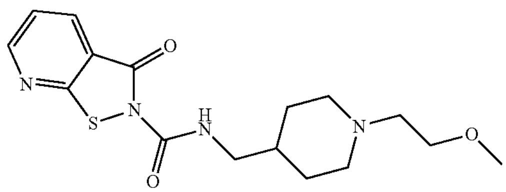 [SMILES: COCCN1CCC(CNC(=O)n2sc3ncccc3c2=O)CC1] | 3-Oxo-3H-isothiazolo[5,4-b]pyridine-2-carboxylic acid [1-(2-methoxy-ethyl)-piperidin-4-ylmethyl]-amide<br>C16H22N4O3S 350.443 |
| 143 | 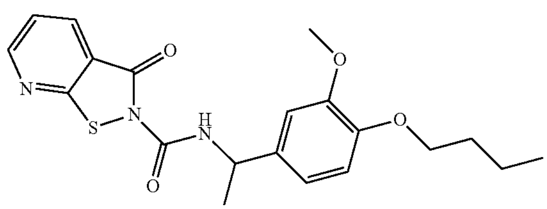 [SMILES: CCCCOc1ccc(C(C)NC(=O)n2sc3ncccc3c2=O)cc1OC] | 3-Oxo-3H-isothiazolo[5,4-b]pyridine-2-carboxylic acid [1-(4-butoxy-3-methoxy-phenyl)-ethyl]-amide<br>C20H23N3O4S 401.488 |
| 144 | 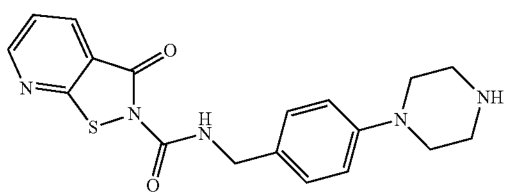 [SMILES: O=C(NCc1ccc(N2CCNCC2)cc1)n1sc2ncccc2c1=O] | 3-Oxo-3H-isothiazolo[5,4-b]pyridine-2-carboxylic acid 4-piperazin-1-yl-benzylamide<br>C18H19N5O2S<br>369.448 |
| 145 | 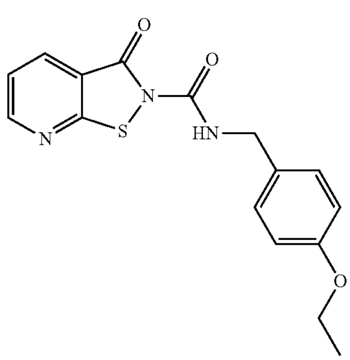 [SMILES: CCOc1ccc(CNC(=O)n2sc3ncccc3c2=O)cc1] | 3-Oxo-3H-isothiazolo[5,4-b]pyridine-2-carboxylic acid 4-ethoxy-benzyl-amide<br>C16H15N3O3S<br>329.38 |
| 146 | 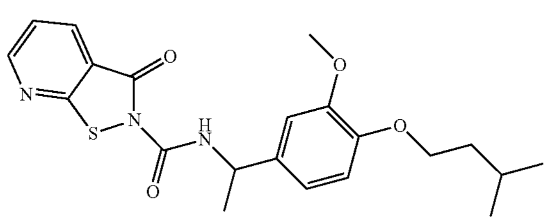 [SMILES: COc1cc(C(C)NC(=O)n2sc3ncccc3c2=O)ccc1OCCC(C)C] | 3-Oxo-3H-isothiazolo[5,4-b]pyridine-2-carboxylic acid {1-[3-methoxy-4-(3-methyl-butoxy)-phenyl]-ethyl}-amide<br>C21H25N3O4S<br>415.515 |
| 147 | 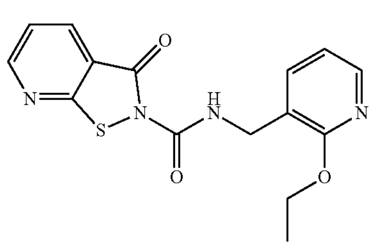 [SMILES: CCOc1ncccc1CNC(=O)n1sc2ncccc2c1=O] | 3-Oxo-3H-isothiazolo[5,4-b]pyridine-2-carboxylic acid (2-ethoxy-pyridin-3-ylmethyl)-amide<br>C15H14N4O3S<br>330.368 |

| Example No. | Structure | Name / Empirical formula / Molar mass [g/mol] |
|---|---|---|
| 148 | 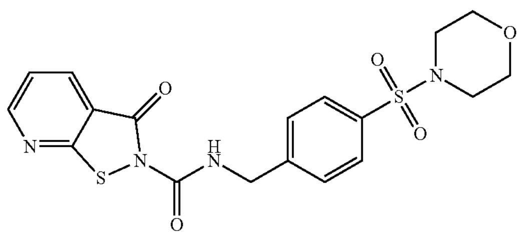 [SMILES: O=C(NCc1ccc(S(=O)(=O)N2CCOCC2)cc1)n1sc2ncccc2c1=O] | 3-Oxo-3H-isothiazolo[5,4-b]pyridine-2-carboxylic acid 4-(morpholine-4-sulfonyl)-benzylamide<br>C18H18N4O5S2<br>434.496 |
| 149 | 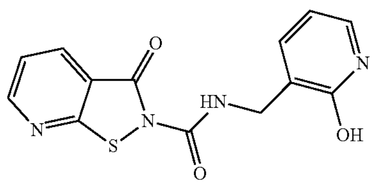 [SMILES: O=C(NCc1cccnc1O)n1sc2ncccc2c1=O] | 3-Oxo-3H-isothiazolo[5,4-b]pyridine-2-carboxylic acid (2-hydroxy-pyridin-3-ylmethyl)-amide<br>C13H10N4O3S<br>302.314 |
| 150 | 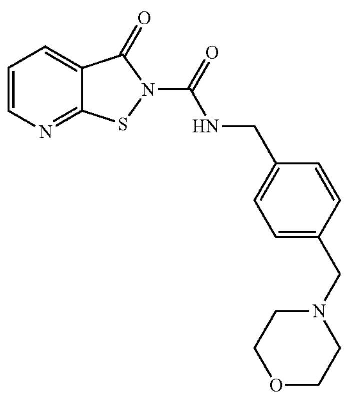 [SMILES: O=C(NCc1ccc(CN2CCOCC2)cc1)n1sc2ncccc2c1=O] | 3-Oxo-3H-isothiazolo[5,4-b]pyridine-2-carboxylic acid 4-morpholin-4-yl-methyl-benzylamide<br>C19H20N4O3S<br>384.46 |
| 151 | 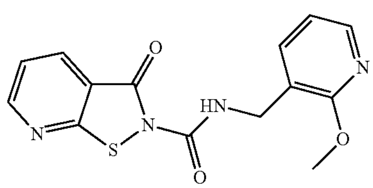 [SMILES: COc1ncccc1CNC(=O)n1sc2ncccc2c1=O] | 3-Oxo-3H-isothiazolo[5,4-b]pyridine-2-carboxylic acid (2-methoxy-pyridin-3-ylmethyl)-amide<br>C14H12N4O3S<br>316.34 |
| 152 | 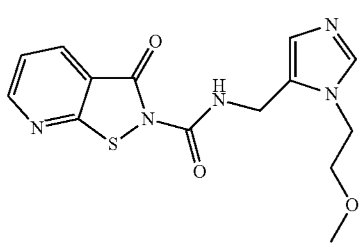 [SMILES: COCCn1cncc1CNC(=O)n1sc2ncccc2c1=O] | 3-Oxo-3H-isothiazolo[5,4-b]pyridine-2-carboxylic acid [3-(2-methoxy-ethyl)-3H-imidazol-4-ylmethyl]-amide<br>C14H15N5O3S<br>333.371 |
| 153 | 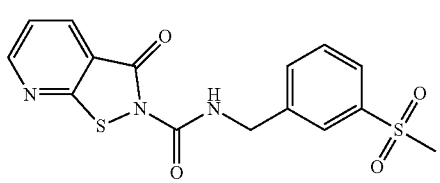 [SMILES: CS(=O)(=O)c1cccc(CNC(=O)n2sc3ncccc3c2=O)c1] | 3-Oxo-3H-isothiazolo[5,4-b]pyridine-2-carboxylic acid 3-methanesulfonyl-benzylamide<br>C15H13N3O4S2<br>363.417 |

-continued

| Example No. | Structure | Name<br>Empirical formula<br>Molar mass [g/mol] |
|---|---|---|
| 154 | 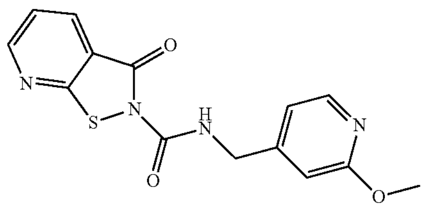 [SMILES: COc1cc(CNC(=O)n2sc3ncccc3c2=O)ccn1] | 3-Oxo-3H-isothiazolo[5,4-b]pyridine-2-carboxylic acid (2-methoxy-pyridin-4-ylmethyl)-amide<br>C14H12N4O3S<br>316.341 |
| 155 | 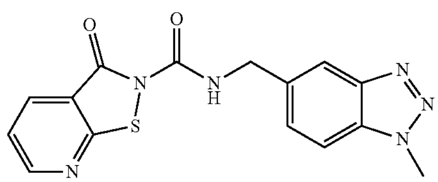 [SMILES: Cn1nnc2cc(CNC(=O)n3sc4ncccc4c3=O)ccc21] | 3-Oxo-3H-isothiazolo[5,4-b]pyridine-2-carboxylic acid (1-methyl-1H-benzotriazol-5-ylmethyl)-amide<br>C15H12N6O2S<br>340.366 |
| 156 | 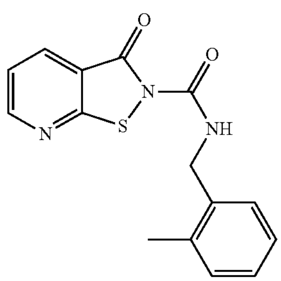 [SMILES: Cc1ccccc1CNC(=O)n1sc2ncccc2c1=O] | 3-Oxo-3H-isothiazolo(5,4-b]pyridine-2-carboxylic acid 2-methyl-benzyl-amide<br>C15H13N3O2S<br>299.353 |
| 157 | 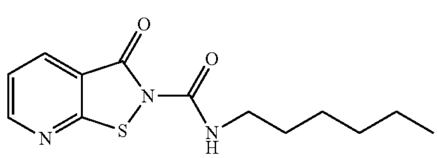 [SMILES: CCCCCCNC(=O)n1sc2ncccc2c1=O] | 3-Oxo-3H-isothiazolo[5,4-b]pyridine-2-carboxylic acid hexylamide<br>C13H17N3O2S<br>279.362 |
| 158 | 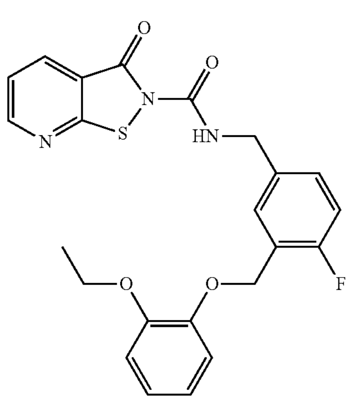 [SMILES: CCOc1ccccc1OCc1cc(CNC(=O)n2sc3ncccc3c2=O)ccc1F] | 3-Oxo-3H-isothiazolo[5,4-b]pyridine-2-carboxylic acid 3-(2-ethoxy-phenoxymethyl)-4-fluoro-benzylamide<br>C23H20FN3O4S<br>453.496 |

| Example No. | Structure | Name<br>Empirical formula<br>Molar mass [g/mol] |
|---|---|---|
| 159 | 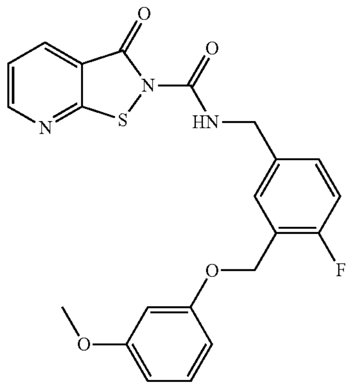 [SMILES: COc1cccc(OCc2cc(CNC(=O)n3sc4ncccc4c3=O)ccc2F)c1] | 3-Oxo-3H-isothiazolo[5,4-b]pyridine-2-carboxylic acid 4-fluoro-3-(3-methoxy-phenoxymethyl)-benzylamide<br>C22H18FN3O4S<br>333.371 |
| 160 | 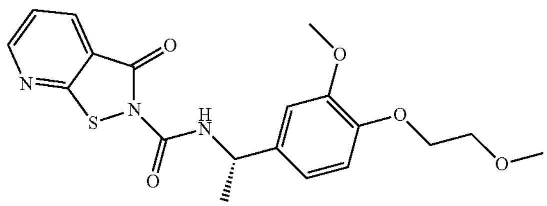 [SMILES: COCCOc1ccc([C@H](C)NC(=O)n2sc3ncccc3c2=O)cc1OC] | 3-Oxo-3H-isothiazolo[5,4-b]pyridine-2-carboxylic acid {(S)-1-[3-methoxy-4-(2-methoxy-ethoxy)-phenyl]-ethyl}-amide<br>C19H21N3O5S<br>403.46 |
| 161 | 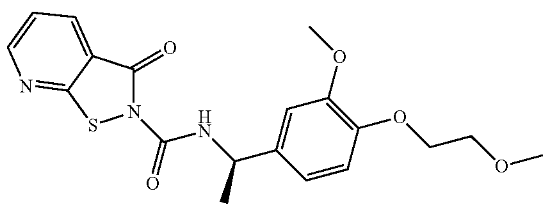 [SMILES: COCCOc1ccc([C@@H](C)NC(=O)n2sc3ncccc3c2=O)cc1OC] | 3-Oxo-3H-isothiazolo[5,4-b]pyridine-2-carboxylic acid {(R)-1-[3-methoxy-4-(2-methoxy-ethoxy)-phenyl]-ethyl}-amide<br>C19H21N3O5S<br>403.46 |

The invention claimed is:

1. A compound of the formula I

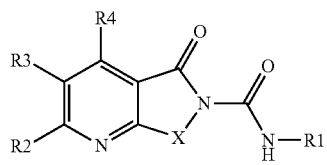

where:
X is S or SO$_2$;
R1 is
a radical of the formula Ia

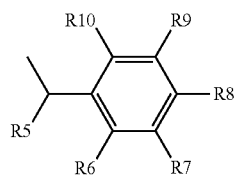

in which
R5 is hydrogen or (C$_1$-C$_3$)-alkyl;
R6, R7, R8, R9, and R10 are each independently hydrogen, CN, OCF$_3$, OCHF$_2$, O—(C$_1$-C$_6$)-alkyl, O—(C$_1$-C$_4$)-alkoxy-(C$_1$-C$_4$)-alkyl, S—(C$_1$-C$_6$)-alkyl, (C$_2$-C$_4$)-haloalkyl, O—(C$_2$-C$_4$)-haloalkyl, (C$_2$-C$_6$)-alkenyl, (C$_2$-C$_6$)-alkynyl, N(R11)(R12), SO$_2$—CH$_3$, SO$_2$—N(R13)(R14), SF$_5$, SCF$_3$, COOH, COO—(C$_1$-C$_6$)-alkyl, CON(R15)(R16), N(R17)CO(R18), N(R19)SO$_2$(R20), CO(R21), (CR22R23)$_x$-O(R24), (CR22R23)$_x$-CO—O(R24), O—(CR22R23)$_x$-CO—O(R24), (CR22R23)$_x$-N(R25)(R26), O—(CR22R23)$_x$-N(R25)(R26), (CR22R23)$_x$-CON(R25)(R26), O—(CR22R23)$_x$-CON(R25)(R26), O—CO—N(R25)(R26), O—CO—(C$_1$-C$_6$)-alkylene-CO—O—(C$_1$-C$_6$)-alkyl, O—CO—(C$_1$-C$_6$)-alkylene-CO—OH, or O—CO—(C$_1$-C$_6$)-alkylene-CO—N(R27)(R28);
with the proviso that at least one R6, R7, R8, R9, or R10 radical is not hydrogen;
x is independently 0, 1, 2, 3, 4, 5, or 6;
or
R7 or R8 is
(O)$_y$—(CH$_2$—)$_{y'}$—(O)$_{y''}$—(CH$_2$)$_{y'''}$—R100;
y and y'' are each independently 0, or 1;
y' and y''' are each independently 1, 2, 3, 4, 5, or 6;
R100 is a 4- to 10-membered mono- or bicyclic saturated, partly unsaturated or aromatic ring which may contain 1 to 4 heteroatoms selected from the group of oxygen, nitrogen and sulfur, where the ring system may optionally be mono- or polysubstituted by F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, (C$_2$-C$_6$)-alkenyl, (C$_3$-C$_8$)-cycloalkyl, O—(C$_3$-C$_8$)-cycloalkyl, (C$_2$-C$_6$)-alkynyl, N(R29)(R30), SO$_2$—CH$_3$, SF$_5$, COOH, COO—(C$_1$-C$_6$)-alkyl, CON(R31)(R32), N(R33)CO(R34), N(R35)SO$_2$(R36), CO(R37), (CR38R39)$_x$-O(R40), (CR38R39)$_x$-CO—O(R40), O—(CR22R23)$_x$-CO—O(R40), (CR22R23)$_x$-N(R41)(R42), O—(CR38R39)$_x$-N(R41)(R42), (CR38R39)$_x$-CON(R41)(R42), O—(CR38R39)$_x$-CON(R41)(R42), O—CO—N(R41)(R42), O—CO—(C$_1$-C$_6$)-alkylene-CO—O—(C$_1$-C$_6$)-alkyl, O—CO—(C$_1$-C$_6$)-alkylene-CO—OH, or O—CO—(C$_1$-C$_6$)-alkylene-CO—N(R43)(R44);

x' is 0, 1, 2, 3, 4, 5, or 6;

or

R7 and R8, or R8 and R9, or R9 and R10 together with the carbon atom which bears them form a monocyclic, 5- to 7-membered saturated, partly unsaturated or aromatic ring system whose individual members may be optionally substituted by —CHR45-, —CR46R47-, =(C—R46)-, O, N or S; with the proviso that no two units from the group of —O—, N and —S— may be adjacent;

R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, and R44 are each independently hydrogen or (C$_1$-C$_6$)-alkyl;

or

R11 and R12, R13 and R14, R15 and R16, R25 and 26, R27 and R28, R29 and R30, R31 and R32, R41 and 42, R43 and 44 each independently form, optionally together with the nitrogen atom to which they are bonded, a 5-6-membered ring which, apart from the nitrogen atom, may optionally include 0-1 further heteroatom from the group of NH, N—(C$_1$-C$_6$)-alkyl, oxygen and sulfur;

R45, R46, and R47 are the same or different and are each F, Cl, Br, I, OH, CF$_3$, NO$_2$, CN, OCHF$_2$, OCF$_3$, SF$_5$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, O—(C$_2$-C$_4$)-haloalkyl, (C$_2$-C$_6$)-alkenyl, (C$_3$-C$_8$)-cycloalkyl, O—(C$_3$-C$_8$)-cycloalkyl, (C$_2$-C$_6$)-alkynyl, N(R134)(R135), SO$_2$—CH$_3$, COOH, COO—(C$_1$-C$_6$)-alkyl, CON(R136)(R137), N(R138)CO(R139), N(R140)SO$_2$(R141), CO(R142), (CR143R144)$_{x''}$-O(R145), (CR143R144)$_{x''}$-CO—O(R145), O—(CR143R144)$_{x''}$-CO—O(R145), (CR143R144)$_{x''}$-N(R146)(R147), O—(CR143R144)$_{x''}$-N(R146)(R147), (CR143R144)$_{x''}$-CON(R146)(R147), O—(CR143R144)$_{x''}$-CON(R146)(R147), O—CO—N(R146)(R147), O—CO—(C$_1$-C$_6$)-alkylene-CO—O—(C$_1$-C$_6$)-alkyl, O—CO—(C$_1$-C$_6$)-alkylene-CO—OH, or O—CO—(C$_1$-C$_6$)-alkylene-CO—N(R148)(R149);

x" is independently 1, 2, 3, 4, 5, or 6;

R134, R135, R136, R137, R138, R139, R140, R141, R142, R143, R144, R145, R146, R147, R148, and R149 are the same or different and are each hydrogen or (C$_1$-C$_6$)-alkyl;

a radical of the formula Ib

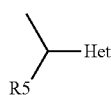

in which

R5 is hydrogen or (C$_1$-C$_3$)-alkyl;

Het is a 4- to 10-membered mono- or bicyclic aromatic ring containing 1 to 4 heteroatoms selected from the group of oxygen, nitrogen and sulfur, where the ring system may optionally be mono- or polysubstituted independently by F, Cl, Br, I, OH, CF$_3$, NO$_2$, CN, OCF$_3$, OCHF$_2$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, O—(C$_2$-C$_4$)-haloalkyl, (C$_2$-C$_6$)-alkenyl, (C$_2$-C$_6$)-alkynyl, N(R48)(R49), SO$_2$—CH$_3$, SO$_2$—N(R50)(R51), SF$_5$, SCF$_3$, COOH, COO—(C$_1$-C$_6$)-alkyl, CON(R52)(R53), N(R54)CO(R55), N(R56)SO$_2$(R57), CO(R58), (CR59R60)$_{x'''}$-O—(R61), (CR59R60)$_{x'''}$-CO—O(R61), O—(CR59R60)$_{x'''}$-CO—O(R61), (CR59R60)$_{x'''}$-N(R62)(R63), O—(CR59R60)$_{x'''}$-N(R62)(R63), (CR59R60)$_{x'''}$-CON(R62)(R63), O—(CR59R60)$_{x'''}$-CON(R62)(R63), O—CO—N(R62)(R63), O—CO—(C$_1$-C$_6$)-alkylene-CO—O—(C$_1$-C$_6$)-alkyl, O—CO—(C$_1$-C$_6$)-alkylene-CO—OH, or O—CO—(C$_1$-C$_6$)-alkylene-CO—N(R64)(R65);

or (O)$_y$—(CH$_2$-)$_{y'}$—(O)$_{y''}$—(CH$_2$)$_{y'''}$—R101, x''' is independently 1, 2, 3, 4, 5, or 6;

y and y'' are each independently 0, or 1;

y' and y''' are each independently 0, 1, 2, 3, 4, 5, or 6;

R101 is a 4- to 10-membered mono- or bicyclic saturated, partly unsaturated or aromatic ring which may contain 1 to 4 heteroatoms selected from the group of oxygen, nitrogen and sulfur, where the ring system may optionally be mono- or polysubstituted by F, Cl, Br, I, OH, CF$_3$, NO$_2$, CN, OCHF$_2$, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, (C$_2$-C$_6$)-alkenyl, (C$_3$-C$_8$)-cycloalkyl, O—(C$_3$-C$_8$)-cycloalkyl, (C$_2$-C$_6$)-alkynyl, N(R66)(R67), SO$_2$—CH$_3$, SF$_5$, COOH, COO—(C$_1$-C$_6$)-alkyl, CON(R68)(R69), (C), N(R70)CO(R71), N(R72)SO$_2$(R73), CO(R74), (CR75R76)$_{x''''}$-O(R77R75R76)$_{x''''}$-CO-O(R77), O—(CR75R76)$_{x''''}$-CO—O(R77), (CR75R76)$_{x''''}$-N(R78)(R79), O—(CR75R76)$_{x''''}$-N(R78)(R79), (CR75R76)$_{x''''}$-CON(R78)(R79), O—(CR75R76)$_{x''''}$-CON(R78)(R79), O—CO—N(R78)(R79), O—CO—(C$_1$-C$_6$)-alkylene-CO—O—(C$_1$-C$_6$)-alkyl, O—CO—(C$_1$-C$_6$)-alkylene-CO—OH, or O—CO—(C$_1$-C$_6$)-alkylene-CO—N(R80)(R81);

x'''' is independently 1, 2, 3, 4, 5, or 6;

R48, R49, R50, R51, R52, R53, R54, R55, R56, R57, R58, R59, R60, R61, R62, R63, R64, R65, R66, R67, R68, R69, R70, R71, R72, R73, R74, R75, R76, R77, R78, R79, R80, and R81 are each independently hydrogen or (C$_1$-C$_6$)-alkyl;

or

R48 and R49, R50 and R51, R52 and R53, R62 and R63, R64 and R65, R66 and R67, R68 and R69, R78 and R79, R80 and R81 each independently form, optionally together with the nitrogen atom to which they are bonded, a 5-6-membered ring which, apart from the nitrogen atom, may optionally include 0-1 further heteroatom from the group of NH, N—$(C_1-C_6)$-alkyl, oxygen and sulfur;
a radical of the formula Ic

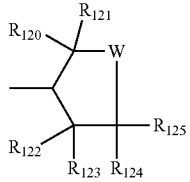

in which

W is —C(R126)(R127)-, —C(R126)(R127)-C(R128)(R129)-, or —C(R126)(R127)-O—;

R120, R121, R123, R125, R126, R127, R128, and R129 are the same or different and are each hydrogen, F, Cl, Br, I, OH, $CF_3$, $NO_2$, CN, $OCHF_2$, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkenyl, $(C_2-C_6)$-alkynyl, N(R90)(R91), $SO_2$—$CH_3$, COOH, COO—$(C_1-C_6)$-alkyl, CON(R92)(R93), N(R94)CO(R95), N(R96)$SO_2$(R97), CO(R98), $(CR99R102)_z$-O(R103), $(CR99R76)_z$CO—O(R103), O—$(CR99R102)_z$-CO—O(R103), $(CR99R102)_z$-N(R104)(R105), O—$(CR99R102)_z$-N(R104)(R105), $(CR99R102)_z$-CON(R104)(R105), O—$(CR99R102)_z$-CON(R104)(R105), O—CO—N(R104)(R105), O—CO—$(C_1-C_6)$-alkylene-CO—O—$(C_1-C_6)$-alkyl, O—CO—$(C_1-C_6)$-alkylene-CO—OH, or O—CO—$(C_1-C_6)$-alkylene-CO—N(R106)(R107);

z is independently 1, 2, 3, 4, 5, or 6;

R90, R91, R92, R93, R94, R95, R96, R97, R98, R99, R102, R103, R104, R105, R106, and R107 are the same or different and are each hydrogen or $(C_1-C_6)$-alkyl;

R122 and R124, together with the carbon atom which bears them form a monocyclic, 5- or 6-membered saturated, partly unsaturated or aromatic ring system whose individual members may be optionally substituted by —CHR130-, —CR131R132-, or =(C—R133)-;

R130, R131, R132, and R133 are the same or different and are each F, Cl, Br, I, OH, $CF_3$, $NO_2$, CN, $OCHF_2$, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R160)(R161), $SO_2$—$CH_3$, COOH, COO—$(C_1-C_6)$-alkyl, CON(R162)(R163), N(R164)CO(R165), N(R166)$SO_2$(R167), CO(R168), $(CR169R170)_z$-O(R171), $(CR169R170)_z$-CO—O(R77), O—$(CR169R170)_z$-CO—O(R171), $(CR169R170)_z$-N(R172)(R173), O—$(CR169R170)_z$-N(R172)(R173), $(CR169R170)_z$-CON(R172)(R173), O—$(CR169R170)_z$-CON(R172)(R173), O—CO—N(R172)(R173), O—CO—$(C_1-C_6)$-alkylene-CO—O—$(C_1-C_6)$-alkyl, O—CO—$(C_1-C_6)$-alkylene-CO—OH, or O—CO—$(C_1-C_6)$-alkylene-CO—N(R172)(R173);

z' is independently 1, 2, 3, 4, 5, or 6;

R160, R161, R162, R163, R164, R165, R166, R167, R168, R169, R170, R171, R172, and R173 are the same or different and are each hydrogen or $(C_1-C_6)$-alkyl;

or

R160 and R161, R162 and R163, R172 and R173 each independently form, optionally together with the nitrogen atom to which they are bonded, a 5-6-membered ring which, apart from the nitrogen atom, may optionally include 0-1 further heteroatom from the group of NH, N—$(C_1-C_6)$-alkyl, oxygen and sulfur;

R2, R3, and R4 are the same or different and are each hydrogen, F, Cl, Br, I, OH, $CF_3$, $NO_2$, CN, $OCHF_2$, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_3-C_8)$-cycloalkenyl, aryl, $(C_2-C_6)$-alkynyl, N(R200)(R201), $SO_2$—$CH_3$, COOH, COO—$(C_1-C_6)$-alkyl, CON(R202)(R203), N(R204)CO(R205), N(R206)$SO_2$(R207), CO(R208), $(CR209R210)_{z''}$-O(R211), $(CR209R210)_{z''}$-CO—O(R211), O—$(CR209R210)_{z''}$-CO—O(R211), $(CR209R210)_{z''}$-N(R212)(R213), O—$(CR209R210)_{z''}$-N(R212)(R213), $(CR209R210)_{z''}$-CON(R212)(R213), O—$(CR209R210)_{z''}$-CON(R212)(R213), O—CO—N(R212)(R213), O—CO—$(C_1-C_6)$-alkylene-CO—O—$(C_1-C_6)$-alkyl, O—CO—$(C_1-C_6)$-alkylene-CO—OH, or O—CO—$(C_1-C_6)$-alkylene-CO—N(R212)(R213);

z" is independently 1, 2, 3, 4, 5, or 6;

R200, R201, R202, R203, R204 R205, R206, R207, R208, R209, R210, R211, R212, and R213 are the same or different and are each hydrogen or $(C_1-C_6)$-alkyl;

or

R200 and R201, R202 and R203, R212 and R213 each independently form, optionally together with the nitrogen atom to which they are bonded, a 5-6-membered ring which, apart from the nitrogen atom, may optionally include 0-1 further heteroatom from the group of NH, N—$(C_1-C_6)$-alkyl, oxygen and sulfur;

the tautomeric forms of the compound and the physiologically compatible salts and N-oxides thereof.

2. A compound of the formula I as claimed in claim 1, in which R1 is a radical of the formula Ia

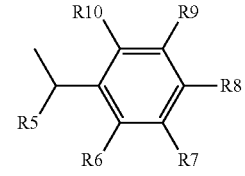

in which

R5 is hydrogen or $CH_3$;

R6, R7, R8, R9, and R10 are each independently hydrogen, $OCF_3$, $SCF_3$, $OCHF_2$, O—$(C_1-C_6)$-alkyl, O—$(C_1-C_4)$-alkoxy-$(C_1-C_4)$-alkyl, S—$(C_1-C_6)$-alkyl, $SO_2$—$CH_3$, $SO_2$—N(R13)(R14), COOH, COO—$(C_1-C_6)$-alkyl, $(CR22R23)_x$-O(R24), $(CR22R23)_x$-CO—O(R24), O—$(CR22R23)_x$-CO—O(R24), $(CR22R23)_x$-N(R25)(R26), O—$(CR22R23)_x$-N(R25)(R26), or $(CR22R23)_x$-CON(R25)(R26);

with the proviso that at least one R6, R7, R8, R9, or R10 radical is not hydrogen;

x is independently 0, 1, 2, 3, or 4;

or

R7 or R8 is

R100, —CH$_2$—R100, —OCH$_2$—R100, —CH$_2$—O—R100, —CH$_2$—O—CH$_2$—R100 or —O—CH$_2$CH$_2$—R100;

R100 is a 4- to 7-membered monocyclic saturated, partly unsaturated or aromatic ring which contains 1 to 3 heteroatoms selected from the group of oxygen, nitrogen and sulfur, where the ring system may additionally be mono- or polysubstituted by F, Cl, Br, OH, CF$_3$, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, SO$_2$—CH$_3$, COOH, COO—(C$_1$-C$_6$)-alkyl, N(R35)SO$_2$(R36), CO(R37), (CR38R39)$_{x'}$-O(R40), (CR38R39)$_{x'}$-CO—O(R40), O—(CR22R23)$_{x'}$-CO—O(R40), (CR22R23)$_{x'}$-N(R41)(R42), O—(CR38R39)$_{x'}$-N(R41)(R42), (CR38R39)$_{x'}$-CON(R41)(R42), or O—(CR38R39)$_{x'}$-CON(R41)(R42);

x' is independently 1, 2, 3, or 4;

or

R7 and R8, or R8 and R9, or R9 and R10 together with the carbon atom which bears them form —O—CH$_2$—O—, —O—CH$_2$—CH$_2$—O—, —O—CH$_2$—CH$_2$—CH$_2$—O—, —O—CF$_2$—O—, or —N(CH$_3$)—N=N—;

R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, and R42 are each independently hydrogen or (C$_1$-C$_6$)-alkyl;

or

R11 and R12, R13 and R14, R15 and R16, R25 and 26, R27 and R28, R29 and R30, R31 and R32, R41 and 42, R43 and 44 each independently form, optionally together with the nitrogen atom to which they are bonded, a 5-6-membered ring which, apart from the nitrogen atom, may optionally include 0-1 further heteroatom from the group of NH, N—(C$_1$-C$_6$)-alkyl, oxygen and sulfur.

3. A compound of the formula I as claimed in claim 1, in which R1 is a radical of the formula Ib

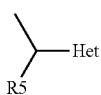

in which:

R5 is hydrogen or CH$_3$;

Het is selected from the group of pyridine, pyrazole, imidazole, oxazole, oxadiazole, benzothiophene, and imidazo[2,1-b]thiazole, where Het may optionally be mono- or polysubstituted independently by F, Cl, Br, CF$_3$, OCF$_3$, OCHF$_2$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, SO$_2$—CH$_3$, SO$_2$—N(R50)(R51), COOH, COO—(C$_1$-C$_6$)-alkyl, N(R56)SO$_2$(R57), CO(R58), (CR59R60)$_{x'''}$-O(R61), (CR59R60)$_{x'''}$-CO—O(R61), O—(CR59R60)$_{x'''}$-CO—O(R61), (CR59R60)$_{x'''}$-N(R62)(R63), O—(CR59R60)$_{x'''}$-N(R62)(R63), (CR59R60)$_{x'''}$-CON(R62)(R63), O—(CR59R60)$_{x'''}$-CON(R62)(R63), O—CO—N(R62)(R63), O—CO—(C$_1$-C$_6$)-alkylene-CO—(C$_1$-C$_6$)-alkyl, O—CO—(C$_1$-C$_6$)-alkylene-CO—OH, or O—CO—(C$_1$-C$_6$)-alkylene-CO—N(R64)(R65);

or (O)$_y$—(CH$_2$-)$_{y'}$-(O)$_{y''}$—(CH$_2$)$_{y'''}$—R101, x''' is independently 1, 2, 3, or 4;

y and y'' are each independently 0, or 1;

y' and y''' are each independently 0, 1, or 2;

R101 is a 4- to 10-membered mono- or bicyclic saturated, partly unsaturated or aromatic ring which may contain 1 to 4 heteroatoms selected from the group of oxygen, nitrogen and sulfur, where the ring system may optionally be mono- or polysubstituted by F, Cl, Br, I, OH, CF$_3$, NO$_2$, CN, OCHF$_2$, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, (C$_2$-C$_6$)-alkenyl, (C$_3$-C$_8$)-cycloalkyl, O—(C$_3$-C$_8$)-cycloalkyl, (C$_2$-C$_6$)-alkynyl, N(R66)(R67), SO$_2$—CH$_3$, SF$_5$, COOH, CO—(C$_1$-C$_6$)-alkyl, CON(R68)(R69), (C), N(R70)CO(R71), N(R72)SO$_2$(R73), CO(R74), (CR75R76)$_{x''''}$-O(R77R75R76)$_{x''''}$-CO—O(R77), O—(CR75R76)$_{x''''}$—CO—O(R77), (CR75R76)$_{x''''}$-N(R78)(R79), O—(CR75R76)$_{x''''}$-N(R78)(R79), (CR75R76)$_{x''''}$-CON(R78)(R79), O—(CR75R76)$_{x''''}$-CON(R78)(R79), O—CO—N(R78)(R79), O—CO—(C$_1$-C$_6$)-alkylene-CO—O—(C$_1$-C$_6$)-alkyl, O—CO—(C$_1$-C$_6$)-alkylene-CO—OH, or O—CO—(C$_1$-C$_6$)-alkylene-CO—N(R80)(R81);

x'''' is independently 1, 2, 3, 4, 5, or 6;

R48, R49, R50, R51, R52, R53, R54, R55, R56, R57, R58, R59, R60, R61, R62, R63, R64, R65, R66, R67, R68, R69, R70, R71, R72, R73, R74, R75, R76, R77, R78, R79, R80, and R81 are each independently hydrogen or (C$_1$-C$_6$)-alkyl;

or

R48 and R49, R50 and R51, R52 and R53, R62 and R63, R64 and R65, R66 and R67, R68 and R69, R78 and R79, R80 and R81 each independently form, optionally together with the nitrogen atom to which they are bonded, a 5-6-membered ring which, apart from the nitrogen atom, may optionally include 0-1 further heteroatom from the group of NH, N—(C$_1$-C$_6$)-alkyl, oxygen and sulfur.

4. A compound of the formula I as claimed in claim 1, in which R1 is a radical of the formula Ic:

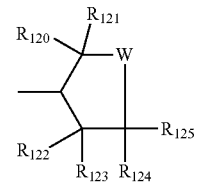

in which

W is —C(R126)(R127)-, —C(R126)(R127)-C(R128)(R129)-, or —C(R126)(R127)-O—;

R120, R121, R123, R125, R126, R127, R128, and R129 are the same or different and are each hydrogen, (C$_1$-C$_6$)-alkyl, oxo, or COO—(C$_1$-C$_6$)-alkyl;

R122 and R124 together with the carbon atom which bears them form a monocyclic, 6-membered aromatic ring system whose individual members may be optionally substituted by =(C—R133)-;

R133 is the same or different and is F, Cl, Br, I, OH, CF$_3$, NO$_2$, CN, OCHF$_2$, OCF$_3$, SF$_5$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, O—(C$_2$-C$_4$)-haloalkyl, $(C_2-C_6)$-alkenyl, $(C_2-C_6)$-alkynyl, N(R160)(R161), $SO_2$—$CH_3$, COOH, COO—$(C_1-C_6)$-alkyl, CON(R162)(R163), N(R164)CO(R165), N(R166)$SO_2$(R167), CO(R168), $(CR169R170)_{z'}$-O(R171), $(CR169R170)_{z'}$, —CO—O(R77), 0-$(CR169R170)_{z'}$-CO—O(R171), $(CR169R170)_{z'}$-N(R172)(R173), O—$(CR169R170)_{z'}$-N(R172)(R173), $(CR169R170)_{z'}$-CON(R172)(R173), O—$(CR169R170)_{z'}$-CON(R172)(R173), O—CO—N(R172)(R173), O—CO—$(C_1-C_6)$-alkylene-CO—O—$(C_1-C_6)$-alkyl, O—CO—$(C_1-C_6)$-alkylene-CO—OH, or O—CO—$(C_1-C_6)$-alkylene-CO—N(R172)(R173);

z' is independently 1, 2, 3, 4, 5, or 6;

R160, R161, R162, R163, R164, R165, R166, R167, R168, R169, R170, R171, R172, and R173 are the same or different and are each hydrogen or $(C_1-C_6)$-alkyl;

or

R160 and R161, R162 and R163, R172 and R173 each independently form, optionally together with the nitrogen atom to which they are bonded, a 5-6-membered ring which, apart from the nitrogen atom, may optionally include 0-1 further heteroatom from the group of NH, N—$(C_1-C_6)$-alkyl, oxygen and sulfur.

5. A compound of the formula I as claimed in claim 1, in which

R2 is hydrogen, —$(C_1-C_6)$-alkyl, $(C_3-C_8)$-cycloalkyl or phenyl;

R3 is hydrogen;

R4 is hydrogen or —$(C_1-C_6)$-alkyl.

6. A pharmaceutical composition comprising one or more of the compounds of the formula I as claimed in claim 1 together with a pharmaceutically acceptable carrier.

7. The pharmaceutical composition as claimed in claim 6, which comprises, as a further active ingredient, metformin, arcabose, glibenclamide, glimepiride, gliclazide, gliquidone, pioglitazone, rosiglitazone, exenatide, miglitol, vildagliptin, sitagliptin, repaglinide, nateglinide or mitiglinide.

8. The pharmaceutical composition as claimed in claim 6, which comprises, as a further active ingredient, one or more of the following: an antidiabetic, an active hypoglycemic ingredient, an HMG-CoA reductase inhibitor, a cholesterol absorption inhibitor, a PPAR gamma agonist, a PPAR alpha agonist, a PPAR alpha/gamma agonist, a fibrate, an MTP inhibitor, a bile acid absorption inhibitor, a CETP inhibitor, a polymeric bile acid adsorber, an LDL receptor inducer, an ACAT inhibitor, an antioxidant, a lipoprotein lipase inhibitor, an ATP citrate lyase inhibitor, a squalene synthetase inhibitor, a lipoprotein (a) antagonist, a lipase inhibitor, an insulin, a sulfonylurea, a biguanide, a meglitinide, a thiazolidinedione, a α-glucosidase inhibitor, an active ingredient which acts on the ATP-dependent potassium channel of the beta cells, a CART agonist, an NPY agonist, an MC4 agonist, an orexin antagonist, an H3 agonist, a TNF agonist, a CRF antagonist, a CRF BP antagonist, a urocortin agonist, a β3 agonist, a MSH (melanocyte-stimulating hormone) agonist, a CCK agonist, a serotonin reuptake inhibitor, a mixed serotoninergic and noradrenergic compound, a 5HT agonist, a bombesin agonist, a galanin antagonist, a growth hormone, a growth hormone-releasing compound, a TRH agonist, a decoupling protein 2 or 3 modulator, a leptin agonist, a DA agonist, alipase/amylase inhibitor, a PPAR modulator, a RXR modulator, a TR β agonist, or an amphetamine.

9. The pharmaceutical composition as claimed in claim 8 wherein the DA agonist is bromocriptine or Doprexin.

10. A method of treating a disorder of fatty acid metabolism or glucose utilization wherein said disorder involves insulin resistance, in a patient in need thereof comprising administering to said patient a therapeutically-effective amount of the pharmaceutical composition of claim 6.

11. A method of treating a dyslipidemia or a sequalae thereof in a patient in need thereof comprising administering to said patient a therapeutically-effective amount of the pharmaceutical composition of claim 6.

12. A method of treating a condition associated with metabolic syndrome, diabetes mellitus, or the associated sequalae wherein said condition involves insulin resistance, in a patient in need thereof comprising administering to said patient a therapeutically-effective amount of the pharmaceutical composition of claim 6.

13. A method of treating a state associated with a lowered HDL level in a patient in need thereof comprising administering to said patient a therapeutically-effective amount of the pharmaceutical composition of claim 6.

14. A method of treating an atherosclerotic disorder in a patient in need thereof comprising administering to said patient a therapeutically-effective amount of the pharmaceutical composition of claim 6.

15. A method of treating a disorder involving insulin resistance in a patient in need thereof comprising administering to said patient a therapeutically-effective amount of the pharmaceutical composition of claim 6 with at least one further active ingredient.

16. A process for preparing a pharmaceutical composition comprising one or more of the compounds of the formula I as claimed in claim 1, comprising mixing said one or more compounds with a pharmaceutically suitable carrier and converting said mixture to a form suitable for administration.

* * * * *

UNITED STATES PATENT AND TRADEMARK OFFICE
CERTIFICATE OF CORRECTION

PATENT NO. : 8,933,024 B2
APPLICATION NO. : 13/805289
DATED : January 13, 2015
INVENTOR(S) : Stefan Petry et al.

It is certified that error appears in the above-identified patent and that said Letters Patent is hereby corrected as shown below:

In the Claims:

At column 143, claim number 1, line 9, please replace "$(CR38R39)_x$-O(R40)" with --$(CR38R39)_{x'}$-O(R40)--;

At column 144, claim number 1, lines 22-23: please replace "$(CR59R60)_{x''''}$-O-(R61)" with --$(CR59R60)_{x''''}$-O(R61)--;

At column 145, claim number 1, line 29: please replace "$(CR99R76)_z$CO-O(R103)" with --$(CR99R76)_z$-CO-O(R103)--;

At column 146, claim number 1, line 30: please replace "R204R205" with --R204, R205--;

At column 148, claim number 3, lines 15-16: please replace "CO-$(C_1$-$C_6)$-alkyl" with --COO-$(C_1$-$C_6)$-alkyl--;

At column 149, claim number 4, line 5: please replace "(CR169R170), -CO-O(R77)" with --$(CR169R170)_{z'}$-CO-O(R77)--;

At column 149, claim number 4, lines 5-6: please replace "0-$(CR169R170)_{z'}$-CO-O(R171)" with --O-$(CR169R170)_{z'}$-CO-O(R171)--; and At column 150, claim number 8, line 12: please replace "alipase/" with --a lipase/--.

Signed and Sealed this
Seventh Day of July, 2015

Michelle K. Lee
*Director of the United States Patent and Trademark Office*